United States Patent
Tarrand et al.

(10) Patent No.: US 10,646,574 B2
(45) Date of Patent: May 12, 2020

(54) FORMULATIONS OF INTRAARTICULAR PHARMACEUTICAL AGENTS AND METHODS FOR PREPARING AND USING THE SAME

(71) Applicant: Board of Regents, The University of Texas System, Austin, TX (US)

(72) Inventors: Jeffrey J. Tarrand, Houston, TX (US); Borje S. Andersson, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/327,689

(22) PCT Filed: Jul. 20, 2015

(86) PCT No.: PCT/US2015/041132
§ 371 (c)(1),
(2) Date: Jan. 20, 2017

(87) PCT Pub. No.: WO2016/014408
PCT Pub. Date: Jan. 28, 2016

(65) Prior Publication Data
US 2017/0209587 A1    Jul. 27, 2017

Related U.S. Application Data

(60) Provisional application No. 62/026,966, filed on Jul. 21, 2014.

(51) Int. Cl.
| | | |
|---|---|---|
| *A61K 47/32* | (2006.01) | |
| *A61K 45/06* | (2006.01) | |
| *A61K 9/00* | (2006.01) | |
| *A61K 31/137* | (2006.01) | |
| *A61K 47/06* | (2006.01) | |
| *A61K 47/20* | (2006.01) | |
| *A61K 47/36* | (2006.01) | |
| *A61K 47/38* | (2006.01) | |
| *A61K 47/24* | (2006.01) | |
| *A61K 47/40* | (2006.01) | |
| *A61K 31/75* | (2006.01) | |
| *A61K 31/722* | (2006.01) | |
| *A61K 47/44* | (2017.01) | |
| *A61K 47/60* | (2017.01) | |

(52) U.S. Cl.
CPC ............ *A61K 47/38* (2013.01); *A61K 9/0019* (2013.01); *A61K 31/137* (2013.01); *A61K 31/722* (2013.01); *A61K 31/75* (2013.01); *A61K 45/06* (2013.01); *A61K 47/06* (2013.01); *A61K 47/20* (2013.01); *A61K 47/24* (2013.01); *A61K 47/32* (2013.01); *A61K 47/36* (2013.01); *A61K 47/44* (2013.01); *A61K 47/60* (2017.08)

(58) Field of Classification Search
CPC .............. A61K 47/38; A61K 9/0019
USPC ......................................................... 514/653
See application file for complete search history.

(56) References Cited

U.S. PATENT DOCUMENTS

| | | | |
|---|---|---|---|
| 2,834,748 A | 5/1958 | Bailey et al. | |
| 3,480,583 A | 11/1969 | Bailey et al. | |
| 3,600,418 A | 8/1971 | Bailey et al. | |
| 4,983,585 A * | 1/1991 | Pennell ................... | A61F 9/007 514/57 |
| 5,068,225 A | 11/1991 | Pennell et al. | |
| 5,156,839 A | 10/1992 | Pennell et al. | |
| 5,177,167 A | 1/1993 | Tone et al. | |
| 5,971,809 A | 10/1999 | Ho | |
| 6,133,249 A | 10/2000 | Hills | |
| 6,699,908 B2 * | 3/2004 | Sackler ................. | A61K 31/167 514/563 |
| 7,186,419 B2 | 3/2007 | Petersen | |
| 7,812,098 B2 | 10/2010 | Ernsberger et al. | |
| 7,867,985 B2 | 1/2011 | Burdick et al. | |
| 8,287,594 B2 | 10/2012 | Cragg et al. | |
| 2005/0164980 A1 | 7/2005 | Shimoboji | |
| 2005/0175665 A1 * | 8/2005 | Hunter .................... | A61K 45/06 424/423 |
| 2008/0044476 A1 | 2/2008 | Lyons et al. | |
| 2010/0098749 A1 | 4/2010 | Barenholz et al. | |
| 2012/0020932 A1 | 1/2012 | Yao et al. | |
| 2012/0100103 A1 * | 4/2012 | Park ........................ | A61L 27/52 424/85.2 |
| 2012/0251615 A1 | 10/2012 | Kief | |
| 2012/0277307 A1 | 11/2012 | Waddell | |
| 2012/0308510 A1 | 12/2012 | Laico | |
| 2013/0005681 A1 | 1/2013 | Su et al. | |
| 2013/0035362 A1 * | 2/2013 | Demopulos ........ | A61K 31/4174 514/400 |

(Continued)

FOREIGN PATENT DOCUMENTS

WO    WO 2001/012245    2/2001

OTHER PUBLICATIONS

Honda et al., 11th IEEE Int Conference on Bioinformatics and Bioengineering, (2011), p. 121-124.*

(Continued)

*Primary Examiner* — Yong L Chu
(74) *Attorney, Agent, or Firm* — Parker Highlander PLLC

(57) ABSTRACT

Provided herein are compositions and methods for preparing intraarticular formulations comprising biocompatible pharmaceutical agents and use thereof in the treatment of diseases, such as degenerative bone diseases, including osteoarthritis of the knee, hip, or other joints, and similar chronic or acute destructive arthropathies resulting from autoimmune disorders or infectious disease.

17 Claims, 10 Drawing Sheets

(56) References Cited

U.S. PATENT DOCUMENTS

| | | |
|---|---|---|
| 2013/0084268 A1 | 4/2013 | Bastianelli et al. |
| 2013/0138209 A1 | 5/2013 | Cragg et al. |
| 2013/0189344 A1 | 7/2013 | Drapeau et al. |

OTHER PUBLICATIONS

Miao et al., J of Applied Polymer Science (2011) V122, p. 2139-45.*

Ma et al., J of Applied Polymer Science, (2010), V116, p. 1985-93.*

"Lubricant," Wikipedia, located at https://en.wikipedia.org/wiki/Lubricant, retrieved Nov. 13, 2017.

"NIH Consensus Development Conference on Total Knee Replacement," NIH Consensus Development Conference Statement, Dec. 8-12, 2003.

"Peg problems," Modern Day Music, 2011.

"Total hip replacement," American Academy of Orthopedic Surgeons, located at orthoinfo.aaos.org/topic.cfm?topic=a00377, retrieved Nov. 13, 2017.

Ackland et al., "Low-molecular-weight polyethylene glycol improves survival in experimental sepsis," Crit Car Med., 38:629-636, 2010.

Borgens and Bohnert, "Rapid recovery from spinal cord injury after subcutaneously administered polyethylene glycol," Journal of Neuroscience Research, 66:1179-1186, 2001.

Borgens and Shi, "Immediate recovery from spinal cord injury through molecular repair of nerve membranes with polyethylene glycol," FASEB J., 14:27-35, 2000.

Bove et al., "Weight bearing as a measure of disease progression and efficacy of anti-inflammatory compounds in a model of monosodium iodoacetate-induced osteoarthritis," Osteoarthritis and Cartilage, 11:821-830, 2003.

Britt et al., "Polyethylene Glycol Rapidly Restores Axonal Integrity and Improves the Rate of Motor Behavior Recovery after Sciatic Nerve Crush Injury," J. Neurophysiol., 104:695-703, 2010.

Conforti et al., "Anti-inflammatory activity of monomethoxypolyethylene glycol superoxide dismutase on adjuvant arthritis in rats," Pharmacological Research, 23:51-56, 1991.

Das et al., "Effects of individual control of pH and hypoxia in chondrocyte culture," J. Orthop. Res., 28(4):537-545, 2010.

Delgado, "Analytical Partitioning of poly(ethylene glycol)-modified proteins," J Chromatography B: Biomedical Sci. and Applications, 692:263-272, 1997.

Fee and Van Alstine, "PEG-Proteins: Reaction Engineering and Separation Issues," Biomol. Engineering, 61:924-939, 2006.

Gale, "Biotribological assessment for artificial synovial joints: the role of boundary lubrication," Institute of Health and Biomedical Innovation, Queensland University of Technology, Brisbane, 2007.

Harris (ed.), Polyethylene Glycol Chemistry, Biotechnical and Biomedical Applications. Plenum Press, New York and London, p. 7, 1992.

Henning, "Polyethylene glycols (PEGs) and the pharmaceutical industry," Fine, Specialty & Performance Chemicals, 2002.

Herold et al., "Oxidation of polyethylene glycols by alcohol dehydrogenase," Biochem. Pharmacol., 38:73-76, 1989.

Hlaváček, "The thixotropic effect of the synovial fluid in squeeze-film lubrication of the human hip joint," Biorheology, 38(4):319-334, 2001.

Honda et al., "Development of Artificial Intra-articular Polyethylene Glycol (PEG) Lubricant for Survival of Total Knee Joint Patient (Preliminary Study for Clinical Application)," 2011 IEEE 11th International Conference on Bioinformatics and Bioengineering (BIBE), 2011.

Hutchings, "Friction, lubrication and wear of artificial joints," Professional Engineering Publishing, Bury St Edmunds and London, UK, 2003.

Koob et al., "Intravenous polyethylene glycol inhibits the loss of cerebral cells after brain injury," J. Neurotrauma, 22:1092-1111, 2005.

Krause and Bittner, "Rapid morphological fusion of severed myelinated axons by polyethylene glycol," Proc. Natl. Acad. Sci. USA, 87(4):1471-1475, 1990.

Liberles and Buck, "A second class of chemosensory receptor in the olfactory epithelium," Nature, 442:645-650, 2006.

Lockard et al., "Efficacy and toxicity of the solvent polyethylene glycol 400 in monkey model," Epilepsia, 20(1):77-84, 1979.

McCarty, "Enhanced synovial production of hyaluronic acid may explain rapid clinical response to high-dose glucosamine in osteoarthritis," Medical Hypotheses, 50:507-510, 1998.

McClatchey, Clinical laboratory medicine. Lippincott Williams & Wilkins. p. 512, 2002.

Miller, "Review of Orthopaedics," Sixth Edition, 2012.

Moreland, "Intra-articular hyaluronan (hyaluronic acid) and hylans for the treatment of osteoarthritis: mechanisms of action," Arthritis Research & Therapy, 5(2):54-67, 2003.

Nalam et al., "Macrotribological Studies of Poly(L-lysine)-graft-Poly(ethylene glycol) in Aqueous Glycerol Mixtures," Tribol Lett, 37:541-552, 2010.

Nayak and Jain, "In vitro and in vivo Study of Poly(ethylene glycol) Conjugated Ibuprofen to Extend the Duration of Action," Sci. Pharm., 79:359-373, 2011.

Necas et al., "Hyaluronic acid (hyaluronan): a review," Veterinarni Medicina, 53:397-411, 2008.

Pasut and Veronese, "PEGylation for improving the effectiveness of therapeutic biomolecules," Drugs of Today, 45:687-695, 2009.

PCT International Preliminary Report on Patentability issued in International Application No. PCT/US2015/041132, dated Feb. 2, 2017.

PCT International Search Report and Written Opinion issued in International Application No. PCT/US2015/041132, dated Oct. 23, 2015.

Peng et al., "Hyaluronic acid inhibits nitric oxide-induced apoptosis and dedifferentiation of articular chondrocytes in vitro," Inflamm. Res., 59:519-530, 2010.

Rosenthale and Capetola, "Adjuvant arthritis; immunopathological and hyperalgesic features," Federation Proceedings, 41:2577-2582, 1982.

Shi and Borgens, "Acute repair of crushed guinea pig spinal cord by polyethylene glycol," J. Neurophysiol., 81:2406-2414, 1999.

Stavisky et al., "Melatonin enhances the in vitro and in vivo repair of severed rat sciatic axons," Neuroscience Letters, 376(2):98-101, 2005.

Stern, "Hyaluronan catabolism: a new metabolic pathway," Eur J Cell Biol., 83:317-325, 2004.

Tang et al., "Modulation of collagen-induced arthritis by adenovirus-mediated intra-articular expression of modified collagen type II," Arthritis Research & Therapy, 12:R136, 2010.

Uebelhart et al., "Protective effects of exogenous chondroitin 4,6-sulfate in the acute degradation of articular cartilage in the rabbit" Osteoarthritis and Cartilage, 6:(Suppl. A):6-13, 1998.

Walter et al., "Disposition of [$^{14}$C]Nonoxynol-9 after intravenous or vaginal administration to Female Sprague-Dawley Rats," Tox. Ap. Pharm., 96:258-268, 1988.

Wathier et al., "A Large-Molecular-Weight Polyanion, Synthesized via Ring-Opening Metathesis Polymerization, as a Lubricant for Human Articular Cartilage," J. Am. Chem. Soc., 135(13):4930-4933, 2013.

Xiao et al., "Investigation on three-dimensional temperature field of human knee considering anatomical structure," International J of Heat and Mass Transfer, 54:1851-1860, 2011.

Yudoh et al., "Water-soluble C60 fullerene prevents degeneration of articular cartilage in osteoarthritis via down-regulation of chondrocyte catabolic activity and inhibition of cartilage degeneration during disease development," Arthritis & Rheumatism, 56(10):3307-3318, 2007.

"General notices and requirements," United States Pharmacopeia, 35:3-15, 2012.

"Pharmaceutical calculations in prescription compounding," United States Pharmacopeia, 35(1160):784-795, 2012.

* cited by examiner

FORMULATIONS OF INTRAARTICULAR PHARMACEUTICAL AGENTS AND METHODS FOR PREPARING AND USING THE SAME

The present application is a national phase application under 35 U.S.C. § 371 of International Application No. PCT/US2015/041132, filed Jul. 20, 2015, which claims the priority benefit of U.S. Provisional Application No. 62/026,966, filed Jul. 21, 2014, the entire contents of each of which are incorporated herein by reference.

BACKGROUND OF THE INVENTION

1. Field of the Invention

The present invention relates generally to the field of orthopedics. More particularly, it concerns compositions and methods for preparing intraarticular formulations comprising biocompatible pharmaceutical agents and use thereof in treatment of diseases, such as degenerative bone diseases, including osteoarthritis of the knee, hip, or other joints, and similar chronic or acute destructive arthropathies resulting from (auto-)immune disorders or infectious disease.

2. Description of Related Art

Destructive arthropathies of the large joints resulting from inflammatory processes, such as rheumatoid arthritis or sepsis, have various effective medical treatments, such as methotrexate, corticosteroids, non-steroidal anti-inflammatory agents, or in the case of sepsis, antimicrobial therapies. However, in osteoarthritis or similar chronic joint diseases, even when inflammatory damage has been adequately treated, mechanical dysfunction persists. In osteoarthritis, a non-inflammatory chronic disease, available medical treatments are relatively limited and are generally restricted to pain control, corticosteroid injection, hyaluronic acid injection, and ultimately joint replacement surgery. In these settings analgesics and corticosteroids provide palliation of symptoms, but disease activity and joint destruction invariably progress due to continued mechanical stress. Indeed, mechanical stress provides one experimental means of creating osteoarthritis in animal models (Langenskiold et al., 1979; Cledes et al., 2006; Pape and Madry, 2013). In patients with significant large joint dysfunction, surgical intervention has become the dominant treatment (Losina et al., 2009). Surgery provides excellent relief but with significant rates of both near-term and long-term complications. For example, total knee replacement (TKR) and total hip replacement (THR) surgeries have a major complication rate of approximately 2%, consisting mostly of infection but including heart attack, stroke, and pulmonary embolism (NIH Consensus Development Conference on Total Knee Replacement, 2003; Minnesota Community Measurement, 2010). Further, there is a need for revision surgery in 1% of TKR cases each year post initial surgery. The rate of revision for THR is 14% (NIH Consensus Development Conference on Total Knee Replacement, 2003). Since osteoarthritis progresses with age, older patients typically have the highest morbidity and are also the least likely to be considered suitable surgical candidates. Furthermore, the cost of TKR is approximately $30,000. Similarly, hyaluronic acid (HA) products (SYNVISC®, HYALGEN®, ORTHOVISC®, and others) have proven efficacy; however, they have disadvantages in that they are rapidly metabolized, and thus lose efficacy over the course of several months. Furthermore, they cost about $3,000 per injection. In addition, physicians generally recommend TKR or THR only for significantly debilitating joint disease. Yet, even with strong physician recommendations the acceptance rate among patients for TKR is only about 13% of eligible patients per year (NIH Consensus Development Conference on Total Knee Replacement, 2003; American Academy of Orthopedic Surgeons; Christensson et al., 2004; Beringer et al., 2007; Lalani et al., 2008; Hsu et al., 2012; Maradit Kremers et al., 2013). Thus, there is a need for methods to treat the significant untreated population that includes patients who refuse surgery or who are not surgical candidates due to age or for other medical reasons, such as comorbid conditions.

SUMMARY OF THE INVENTION

Provided herein are compositions and methods for preparing intraarticular formulations comprising biocompatible pharmaceutical agents and use thereof in the treatment of diseases, such as degenerative bone diseases, including osteoarthritis of the knee, hip, or other joints, and similar chronic or acute destructive arthropathies resulting from autoimmune disorders or infectious disease.

In one embodiment, intraarticular formulations are provided that comprise an effective concentration of polyethylene glycol (PEG) of at least 600,000 molecular weight (Mwt). In some aspects, the composition comprises a concentration of PEG of at least 600,000; 700,000; 800,000; 900,000; 1,000,000; 1,500,000; 2,000,000; 2,500,000; 3,000,000; 3,500,000; 4,000,000; 4,500,000; 5,000,000; 5,500,000; 6,000,000; 6,500,000; 7,000,000; 7,500,000; 8,000,000; 8,500,000; 9,000,000; 9,500,000; or 10,000,000 Mwt. For example, in some aspects, a formulation comprises a PEG having a Mwt of between about 500 k and 10M; 500 k and 8M; or 600 k and 5M. In some aspects, the composition further comprises hydroxyethyl cellulose (HEC). In one aspect, the composition comprises 1.4% PEG 600K or at least 1.4% PEG 600K. In one aspect, the composition comprises 4.5% PEG 600K or at least 4.5% PEG 600K. In one aspect, the composition comprises 6% PEG 600K or at least 6% PEG 600K. In one aspect, the composition comprises 9% PEG 600K or at least 9% PEG 600K. In one aspect, the composition comprises 0.9% PEG 3.6M or at least 0.9% PEG 3.6M.

In a further aspect, the composition comprises 0.9% PEG 4M or at least 0.9% PEG 4M. In one embodiment, intraarticular formulations are provided herein comprising a high molecular weight polyethylene glycol (PEG) and hydroxyethyl cellulose (HEC). In some aspects, the formulation may further comprise PEG-tyramine and/or HEC-tyramine. In one aspect, the formulation may further comprise polyvinyl alcohol (PVA), polyvinylpyrrolidone (PVP), and/or carboxymethyl cellulose (CMC). In still further aspects, a composition of the embodiments may comprise a silicone oil and PEG.

In certain aspects, the formulation may comprise PEG 2M, HEC 1.3M, PEG 600K, CMC 1.7M, and PVP 360K. In certain aspects, the composition may comprise PEG-tyramine 2M, HEC 1.3M, PEG 600K, CMC 1.7M, and PVP 360K. In still further aspects, a composition may comprise a silicone oil, a PEG, such as PEG 600K to 8M, and phosphatidylcholine. For example, a composition may comprise a silicone oil, 0.6-6% PEG 600K to 8M, and 0.1-1.0% phosphatidylcholine.

In some aspects, the formulation may provide lubricity, be nontoxic, be retained in the joint of a mammal, and/or be metabolically stable. In some aspects, the formulation may be a buffer.

In one embodiment, methods are provided for lubricating a joint of a mammal comprising administered into a cavity of the joint an effective amount of a composition of the present embodiments, wherein the composition is a liquid at the temperature of the joint and the oncotic pressure of the composition is not greater than the serum oncotic pressure of the mammal.

In one embodiment, methods are provided for lubricating a joint of a mammal comprising administered into a cavity of the joint an effective amount of a composition comprising at least 0.5, 0.6, 0.7, 0.8, 0.9, 1.0, 1.1, 1.2, 1.3, 1.4, 1.5, 1.6, 1.7, 1.8, 1.9 or 2.0% polyethylene glycol (PEG), wherein the composition is a liquid at the temperature of the joint and the oncotic pressure of the composition is not greater than the serum oncotic pressure of the mammal. For example, in some aspects, a composition comprises at least 0.6% or 1.5% PEG (e.g., about 0.6% to about 6% PEG). In some aspects, administering may comprise injecting the composition into an intra-articular cavity of the joint. In some aspects, administering may comprise warming the composition to the temperature of the joint prior to administration. In some aspects, the mammal may have joint dysfunction, which may be caused by a degenerative bone disease including, but not limited to, osteoarthritis, rheumatoid arthritis, an infectious disease, an immune disease, an autoimmune disease, or sepsis.

In some aspects, the composition may further comprise polyvinyl pyrrolidone (PVP) or polyvinyl alcohol (PVA). In some aspects, the composition may further comprise hydroxyethyl cellulose (HEC), methylcellulose, hydroxypropyl cellulose (HPC), or a combination thereof. In some aspects, the composition may further comprise chondroitin, dextran, polyglucosamine (chitosan), agarose, xanthan gum, alginate, carrageenan, guar gum, locust bean gum, or a combination thereof. In some aspects, the composition may further comprise DMSO, mineral oil, paraffin jelly, silicone oil, or a combination thereof. In some aspects, the composition may further comprise ethanol, steryl alcohol, phosphatidylcholine, oleic acid, oleyl alcohol, hydroxyl stearate, cetyl alcohol, myristyl lactate, isopropyl myristate, or a combination thereof. In one aspect, the composition may comprise PEG-tyramine.

In various aspects, the composition may comprise up to about 1%, 2%, 3%, 4%, 5%, or 6% PEG 600K-10M. In certain aspects, the composition may comprise up to about 6% PEG 600K-10M. In various aspects, the composition may comprise up to about 0.5%, 1%, 1.5%, or 2% PEG 1-2M. In certain aspects, the composition may comprise up to about 2% PEG 1-2M. In various aspects, the composition may comprise up to about 1%, 2%, 3%, 4%, 5%, 6%, 7%, 8%, 9%, 10%, 11%, or 12% PEG 100-600K. In certain aspects, the composition may comprise up to about 12% PEG 100-600K. In certain aspects, the composition may comprise up to about 2% PEG 100-600K.

In various aspects, the composition may comprise up to about 1%, 2%, 3%, 4%, 5%, 6%, 7%, 8%, 9%, 10%, 11%, or 12% HEC. In certain aspects, the composition may comprise up to about 12% HEC. In various aspects, the composition may comprise up to about 1%, 2%, 3%, 4%, 5%, 6%, 7%, 8%, 9%, 10%, 11%, or 12% PVP. In certain aspects, the composition may comprise up to about 12% PVP.

In some aspects, at least a portion of the PEG may be conjugated to an antimicrobial agent, antifungal agent, and/or antiviral agent. In some aspects, at least a portion of the PEG may be comprised in a block polymer. In some aspects, the composition may have a pH from about 7.5 to about 7.8. In some aspects, the composition may be hydrophobic. In some aspects, the composition may be hydrophilic.

In one embodiment, methods are provided for lubricating a joint of a mammal comprising administered an effective amount of a composition comprising at least 10% polyethylene glycol 400 (PEG 400). In various aspects, administering may comprise intravenous injection, slow bolus infusion, subcutaneous injection, intraperitoneal injection, or oral administration.

In one embodiment, methods are provided for lubricating a joint of a mammal comprising administered into a cavity of the joint an effective amount of a composition comprising petroleum jelly and phosphatidylcholine, wherein the composition is a liquid at the temperature of the joint and the oncotic pressure of the composition is not greater than the serum oncotic pressure of the mammal. In one aspect, the composition may comprise 99% petroleum jelly and 0.1% phosphatidylcholine. In one aspect, the method may be a method of treating bone-on-bone osteoarthritis.

In one embodiment, methods are provided for lubricating a joint of a mammal comprising administered into a cavity of the joint an effective amount of a composition comprising hydroxyethyl cellulose, wherein the composition is a liquid at the temperature of the joint and the oncotic pressure of the composition is not greater than the serum oncotic pressure of the mammal.

In one embodiment, methods are provided for lubricating a joint of a mammal comprising administered into a cavity of the joint an effective amount of a composition comprising hydroxyethyl cellulose and polyethylene glycol, wherein the composition is a liquid at the temperature of the joint and the oncotic pressure of the composition is not greater than the serum oncotic pressure of the mammal.

In one embodiment, methods are provided for lubricating a joint of a mammal comprising administered into a cavity of the joint an effective amount of a composition comprising hydroxyethyl cellulose, polyethylene glycol, carboxymethyl cellulose, and polyvinylpyrrolidone, wherein the composition is a liquid at the temperature of the joint and the oncotic pressure of the composition is not greater than the serum oncotic pressure of the mammal.

In one embodiment, methods are provided for lubricating a joint of a mammal comprising administered into a cavity of the joint an effective amount of a composition comprising hydroxyethyl cellulose, polyethylene glycol, and polyvinyl alcohol, wherein the composition is a liquid at the temperature of the joint and the oncotic pressure of the composition is not greater than the serum oncotic pressure of the mammal.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
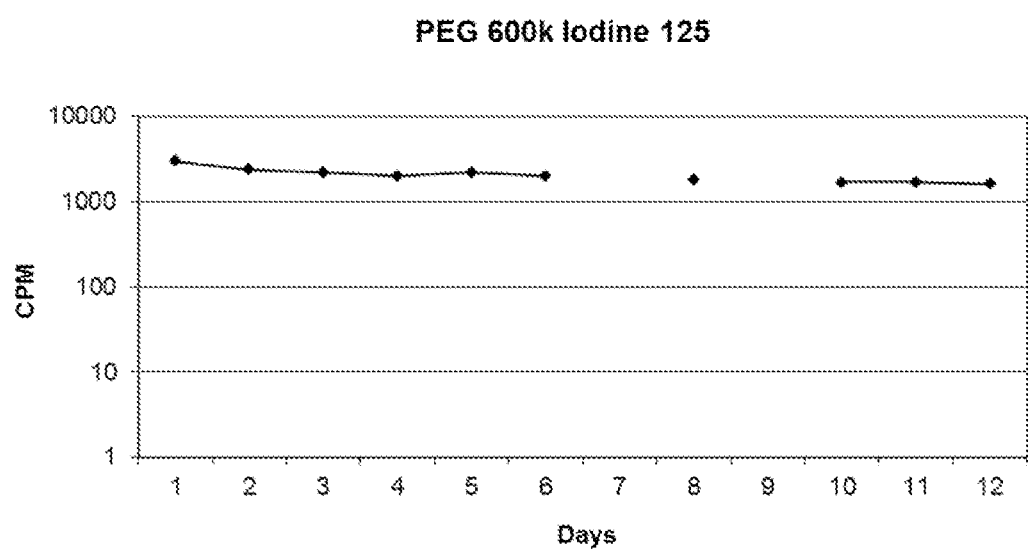
FIG. 1 shows the half-life of high molecular weight PEG in the rat knee in vivo.

The present invention is primarily intended to provide a composition that can be directly injected into a diseased joint space. However, a composition of the present invention may be useful as a lubricant for artificial joints also. These compositions are intended to supplement joint lubrication function in order to reduce mechanical damage to chondrocytes and reduce irritation, and thereby reduce inflammation and pain. The composition is preferably not resorbable from the joint space and is not metabolized to any significant degree. Thus, a PEG-based material, given its prolonged half-life in the joint, will provide sustained lubricating function. In addition, preferred compositions have direct anti-inflammatory properties and are well tolerated biologically (Rosenthale et al., 1982; Conforti et al., 1991; Uebelhart et al., 1998; Borgens and Bohnert, 2001; McClatchey, 2002; Bove et al., 2003; Bittner et al., 2005; Ackland et al., 2010; Tang et al., 2010). A preferred composition may also include agents that provide nutritional support to the joint as an adjunct to other properties of the composition. The product may be part of a kit for use in a specific new sterile procedure requiring pump-assisted injection, may replace surgery, may find use in the non-surgical-candidate population of arthritis patients, and/or may find use as an adjuvant treatment in patients with a prosthetic joint. The composition will preferably be composed is such a way that it will be a liquid at the temperature of the targeted joint (e.g., the human knee is typically 34° C., the human hip typically 37° C.), and may be suitable for an outpatient surgery setting. The material may also be useful in the treatment of disease in small joints. For example, PEG 400 may be useful systemically (taken orally) and enter the joint by diffusion.

Thus, the present invention provides injectable compositions containing at least one high molecular weight synthetic or semi-synthetic biocompatible polymer, with or without the addition of natural polymers. In addition, these compositions, including solutions, suspensions, colloids, or gels, have no, or limited, metabolism in the joint and are non-toxic and non-immunogenic. There are several biophysical properties that compositions of the present invention embody. First, the polymers have a high molecular weight such that at an optimum concentration the composition does not have an excessive oncotic pressure resulting in swelling of the joint. Second, the polymers have a prolonged half-life in the joint relative to hyaluronic acid. Third, the polymers are soluble at the temperature of the joint (~34° C.) (Xiao et al., 2011). Fourth, the compositions are optimized such that they have sufficient oncotic pressure and or hydration and such that they are not overly concentrated in the joint resulting in an insoluble precipitate at the temperature of the joint. Further, there are physiologic properties of the normal joint fluid that are embodied in the present compositions. First, at the optimized concentration(s) the composition(s) provide(s) significant lubricity. Second, the composition(s) provide(s) a slight alkaline buffering potential, mimicking the normal joint fluid pH of 7.5 to 7.8. Third, the compositions mimic the gel effect and non-Newtonian flow (rheologic properties) of the native joint hyaluronic/lubricin gel system thus distributing shock load at rest while providing low viscosity and high lubricity when in motion. These requirements restrict the compositions to a unique range of acceptable molecules and mixed compositions with low toxicity, prolonged half live, low metabolism, low oncotic pressure at the concentrations needed to provide high lubricity, acceptable fluid function in the aqueous environment of the joint, and optimally provide a functional rheologically shear sensitive gel, that does not concentrate into a solid in the joint, remains liquid at joint temperature, and can be injectable at room temperature or after mild heating either by hand or with the assistance of a mechanical assisting pump syringe. Many of the compositions presented below are highly hydrated, aqueous, soluble polymers, such as polyethylene glycol (very high molecular weight polyethylene glycols are sometimes referred to as polyethylene oxide, PEO, or POE). However, the compositions are not necessarily all water soluble. Compositions based on alkanes, such as mineral oil and the oxygen-carrying fluorinated hydrocarbons (FLUORINERT®) and a high molecular weight PEO, and/or steryl alcohol, and/or phosphatidylcholine, and/or detergents, such as CHAPS, TWEEN® 80, sodium cholate, or NP40, form an emulsion that is not water soluble. These detergents are known to be biocompatible and have systemic levels that are tolerable (Walter et al., 1988; McPherson et al., 1996; Barditch-Crovo et al., 1997; Witter et al., 1999). For example, phosphatidylcholine+ steryl alcohol+mineral oil and phosphatidylcholine+steryl alcohol+PEG 400K can be formed into emulsions of interest and are examples of biocompatible hydrophobic lubricants.

In some embodiments, compositions may include solitary or mixed polymers of opposing charge, such as ionizing aqueous acid and basic molecules or molecules containing significant displacement of charge (but non-ionizing, such as polyvinyl alcohol) such that the composition forms a strong gel that breaks under shear stress but instantly reforms at rest and retains excellent lubricity. In the case of non-ionizing molecules, both positive Δ charge and negative delta Δ charge would be needed to mimic the effect of acidic and basic polymer interaction. Here, displaced charge resulting in polar interactions such as hydrogen bonding, or polymers internal positive and negative charge displacement, or a mixture of two or more polymers one with positive charge displacement and the companion (cognate pair) molecule with a negative charge displacement such that a mixed composition forms, which facilitates gel formation. Also contemplated are multi-component heteropolymers or mixed bi-component synthetic or natural linear polymers with complementary opposing charge displacement, with or without facilitating agents, such that they facilitate gel formation. These compositions have certain rheological properties (principally gel formation) that distribute impact force and assist in preventing, or minimizing, mechanical damage to the joint. Further, these polymers are highly hydrated, are resilient to compression, and distribute load in the joint space, thus mimicking the rheological behavior of the HA+lubricin gel system found in normal synovial fluid.

I. JOINT BIOLOGY

Synovial fluid is a biological fluid that is found in the synovial cavity of the joints (e.g., knee, hip, shoulder) of the body between the cartilage and synovium of facing articulating surfaces. Synovial fluid provides nourishment to the cartilage and also serves as a lubricant for the joints. The cells of the cartilage and synovium secrete fluid and the fluid lubricates and reduces friction between the articulating surfaces.

Human synovial fluid is comprised of approximately 85% water. It is derived from the dialysate of blood plasma, which itself is made up of water, dissolved proteins, glucose, clotting factors, mineral ions, hormones, etc. The proteins, albumin and globulins, are present in synovial fluid and are believed to play an important role in the lubrication of the joint area. Other proteins are also found in human synovial fluid, including the glycoproteins such as AGP, A1AT and lubricin.

Another compound that is present in human synovial fluid is hyaluronic acid. Hyaluronic acid is also believed to play a role in lubrication. Human synovial fluid further includes other compounds, such as polysaccharides and phospholipids. The phospholipid, dipalmitoylphosphatidylcholine (DPPC), is also present in human synovial fluid. DPPC is generally regarded as surfactant and is also believed to play a role in the lubrication of the joint.

Hyaluronic acid (HA) is a non-immunogenic linear glycosaminoglycan polymer of repeating disaccharide units composed of d-glucuronic acid and d-N-acetylglucosamine, usually derived from animal or microbial sources. Hyaluronic acid (also known as hyaluronan) typically has a molecular weight in the millions. It is a major component of cartilage and is found as part of the extracellular ground substance and in high concentrations in synovial fluid where it provides significant lubrication to the joint. The half-life of HA is approximately 1-2 days (Stern, 2004). In normal individuals an equal amount of HA is synthesized each day to replace the loss due to rapid turnover; however, in diseased joints HA is rapidly depleted and not replaced (Moreland, 2003; Gale, 2007). HA is predominantly synthesized by the synovium of the joint (McCarty, 1998) and has a primary lubricating role as well as an important nutritional role supporting chondrocyte survival (Peng et al., 2010). In osteoarthritis, diseased joints are deprived of the lubrication functions of HA resulting in further mechanical damage, and further nutritional compromise of the joint. In cartilage, the circulation of oxygen, nutritional components, and removal of waste, is accomplished purely by the mechanical movement of cartilage tissue; there are no arterioles, veins, or capillaries in cartilaginous tissue. Thus, as joint pain increases and mobility decreases, the viability of cartilage is further compromised through loss of nutrition. An effective way of inducing osteoarthritis in rabbits is to simply immobilize the joint (Langenskiold et al., 1979; Cledes et al., 2006).

Considerable progress has been made in the development of biocompatible materials used in prosthetic joints and in this setting several biocompatible materials have been developed. Metallic, plastic and hybrid based prosthetic joints, implantable meniscus substitutes based on collagen or bacterial cellulose, and implantable chondrocyte transplants have all been performed or proposed. Currently, injectable compositions for use in the joint space are largely restricted to injectable hyaluronic acid (SYNVISC® [hylan G-F 20], ORTHOVISC®, SYNVISC®, HYALGAN®, VISCOSEAL®). Further, hyaluronic acid has recently been combined with anti-inflammatory agents, analgesics, anesthetics, and specific cytokine mediators (U.S. Pat. Publn. Nos. 20120251615, 20120277307, 20130005681, 20130084268, incorporated herein by reference). The effectiveness of injectable HA is limited by continued rapid destruction of HA in the context of decreased production of HA from diseased synovial and chondrocyte tissues. As an example, when HA is used to treat diseased equine stifle joints the benefit appears to last approximately one week (Genitrix HY50® datasheet). In humans, the benefits may last up to three months and varies with the degree of osteoarthritic disease, mobility, patient weight, and potentially other factors, such as intrinsic metabolic differences in the population and individual pain thresholds. Therefore, provided herein are improved compositions comprising injectable biocompatible materials, for use as injectable lubrication to natural joints as well as adjunct lubrication to prostatic joints, with the one exception, which is a low molecular weight oral formulation (see Example 9).

II. ASPECTS OF THE PRESENT INVENTION

PEG (or mixtures of different molecular weight PEGs) provides an example of a simple, one species composition, with the primary goal being high lubricity. When considered as a sole molecule in the composition PEG offers the following advantages. Toxicity is well known and is low. PEG has some level of anti-inflammatory effect. The molecule is inexpensive and available in the high molecular weight range necessary for low osmotic effects. Mixtures of high molecular weight PEG and low molecular weight PEG can be adjusted to optimize lubricity and simultaneously provide sufficient osmotic activity to prevent the synovial space from over concentrating the PEG and thus producing a waxy mass in situ. While PEG alone is one possible embodiment, other compounds may be of interest alone or combined with PEG. Several other natural or synthetic polymers can meet these requirements as simple, one species compositions. Examples include, but are not limited to, high molecular weight synthetic biocompatible polymers, such as poly(N-isopropylacrylamide-co-butylacrylate), poly(N-isopropylacrylamide-co-methacrylic acid), poly(N-isopropylacrylamide-co-acrylic acid), poly(N-isopropylacrylamide-co-methacrylic acid-co-octadecyl acrylate, poly(2-oxazoline), polyethylenimine, polyethylenimine branched ethylenediamine, poly(acrylic acid), polymethacrylate, poly(2-ethylacrylic acid), poly(2-propylacrylic acid), poly(acrylic acid-co-maleic acid), poly(methacrylic acid), poly[ethyl acrylate-co-methacrylic acid-co-3-(1-isocyanato-1-methylethyl)-α-methylstyrene], poly(N-isopropylacrylamide-co-methacrylic acid), poly(N-isopropylacrylamide-co-methacrylic acid-co-octadecyl acrylate), poly(2-hydroxyethyl methacrylate), poly(2-dimethylamino)ethyl methacrylate) methyl chloride, poly[(2-ethyldimethylammonioethyl methacrylate ethyl sulfate)-co-(1-vinylpyrrolidone)], poly(1-vinylpyrrolidone-co-2-dimethylaminoethyl methacrylate, poly(ethylene glycol) methyl ether-block-poly(D,L lactide), poly(ethylene glycol)-block-polylactide methyl ether, poly(ethylene oxide)-block-polylactide, 4-arm poly(ethylene oxide), poly(ethylene glycol)-block-poly(ε-caprolactone) methyl ether, poly((ethylene oxide)-block-polycaprolactone, 4-arm (polyethylene oxide), poly(styrene)-block-poly(ethylene glycol), polyethylene-block-poly(ethylene glycol), poly(vinyl alcohol) (PVA), poly(vinyl alcohol-co-ethylene), polyvinylpyrrolidone (PVP), poly(1-vinylpyrrolidone-co-styrene), poly(1-vinylpyrrolidone)-graft-(1-triacontene), poly(1-vinylpyrrolidone-co-vinyl acetate), poly(1-vinylpyrrolidone-co-2-dimethylaminoethyl methacrylate), poly(methyl vinyl ether), poly(methyl vinyl ether-alt-maleic acid), and poly(methyl vinyl ether-alt-maleic acid monoethyl ester). These synthetic biocompatible polymers have the advantage that they may not be cleared rapidly since natural metabolic pathways would be absent.

Many of the above synthetic polymers can be formulated as mixtures, of which there are a large number of possible permutations, and these mixtures can have many different ratios of one or more biologically compatible polymers. Examples of compatible mixtures with possible functional advantages include, for example, poly(N-isopropylacrylamide) (PNIPAM) and polyacrylamide (PAM), poly(N-isopropylacrylamide-co-acrylic acid and acrylic acid, poly(N-isopropylacrylamide-co-acrylamide, poly(N-isopropylacrylamide-co-methacrylic acid-co-octadecyl acrylate and acrylic acid, poly(2-oxazoline) and polyethylenimine (PEI), polyvinylpyrrolidone, and polyvinyl alcohol. All of these pairs act as solvents and promote solubilization in aqueous systems. Several show increased viscosity. Polyvinylpyrrolidone/PVA mixtures form weak gels with potential rheological advantages.

Many polymers usually found as rigid solids can be made with limited degrees of polymerization and can, alone or in mixtures with suitable hydrophobic or hydrophilic carriers, provide a biocompatible lubricating fluid formulation with appropriate half-life and osmotic characteristics. Examples include, ethylene vinyl acetate, polyethylene, polypropylene, poly(tetrafluroethylene), PFA-(tetrafluoroethylene-co-perfluoroalkylvinyl ether), FEP-(hexafluropropylene-co-tetrafluoroethylene), polyvinylidenefluorid-co-hexafluroopropylene), CTFE-(Ethylenechlorotrifluoriethylene), polyethylene glycol-co-polyvinyl alcohol, poly(methylmethacralate), ethylene-co-vinylacetate, poly(dimethylsiloxane), polyether urethanes, polyethylene terphthalate, poly sulphone, poly (ethyleneoxide-co-propyleneoxide), polyether ether kentone based polymers, poly(ε-caprolactone)dimethylacrylate-co-n butylacrylate, poly(glycolic acid), polyeurethane, silicones (low toxicity medical polysiloxanes), other polyolefins, or as mixed compositions of the above, or as mixed block polymers of the above. One example combination is the use of silicone to bridge carbon backbone polymers into blocks of any of the above synthetic biocompatible polymers or mixtures or any of the above biocompatible polymers, or mixtures of biocompatible polymers and natural polymers as desired, for example, combining the high lubricity of polytetrafluoroethylene (Teflon) as short chain/low molecular weight blocks within a highly hydrated hydrophilic high molecular weight backbone block like polyethylene glycol or hydroxyethyl cellulose to support hydrophilization. See U.S. Pat. Nos. 2,834,748 and 5,177,167, incorporated herein by reference.

A class of silicone-based highly branched dendritic polymers may provide potentially useful extended hydrophilic shells, lubricity, and rheological properties when prepared as a mixture and suspended in a suitable hydrophilic or hydrophobic base (e.g., polyethylene glycol+hydroxyethylcellulose or stearyl alcohol+dimethylpolysiloxane). Thus, rather than one species compositions, engineered mixtures may offer advantages. In such cases, molecules can then be considered not based on the utility of achievable lubricity at a certain achievable molecular weight for one species, but can be mixed based on advantageous properties. For example, an optimal proportion of poly(tetrafluroethylene), a polymer known for particularly high lubricity, may only be practical as a suspension, colloid, or true solution in an advantageous carrier, for example, a high molecular weight PEG/HEC or a steryl alcohol/dimethylpolysiloxane solvent. An example of this "phase" solubility concept would be the partition (distribution into the more permissive soluble phase) of PEG-modified molecules in aqueous solution into PEG+water over a dextran+water partition system. The PEG-modified molecules migrate into the PEG+water layer. Similarly, dextran-modified polymers preferentially migrate into the dextran+water layer. Thus, dextran is more soluble in dextran solutions and PEGs are more 'soluble' in PEG solution. While both are fully soluble in water and are miscible in each other, they will partition under some conditions of concentration. This small weak-force can be used to better formulate stable compositions. Without being bound by theory, this partitioning effect is not strictly related to solubility but is due to like molecules more efficiently interacting with each other through van der Waals interactions throughout a large macro molecular structure and thus more efficiently structuring (ordering) the molecule (Savage, 1993). Thus, these interactions effectively generate 'supermolecules,' or polymers that associate and establish an equilibrium with very high molecular weight complexes.

In addition to the above synthetic polymers, there are several natural and semisynthetic biological polymers with low immunogenicity and high lubricity that would be expected to have long biological half-lives since there are no specific degrading enzymes for them in humans. Examples include agar (mixed polysaccharides), agarose, alginate or alginic acid, hydroxyethyl agarose, amylopectin, carrageenan, dextrans, branched poly-dextrans, cyclodextrin polymer, polyglucosamine (chitosan), glycol chitosan, Ficoll, gelatin, gum arabic, neruamic acid (sialic acid), polygalactosamine, polylactosamine, chondroitin, heparin, starch, micro-crystalline starch, polyribosyl ribitol phosphate (PRP), hydroxyethyl starch (HES), carboxymethyl cellulose CM, CM-Dextran, methylcellulose, cellulose colloidal, cellulose microcrystalline, cellulose acetate, cellulose acetate butyrate, cellulose acetate propionate, cellulose propionate, ethyl cellulose, 2-hydroxyethyl cellulose, hydroxyethylcellulose ethoxylate, hydroxypropyl cellulose, hydroxypropyl methyl cellulose, methyl 2-hydroxyethyl cellulose, hydroxyethyl starch, phenoxyacetylcellulose, chitin, glycol-chitin, D-galacto-D-mannan, β-1,3-glucan, arabic acid, guar gum, gum accroides, gum rosin, gum storax, xanthan gum, hypromellose, neoagarohexaitol, neocarradodecaose, neocarraoctaose, neocarratetraose, poly(D,L-lactide), poly-D-lysine hydrobromide, poly-D-glutamic, polygalacturonic acid, micro-crystalline starch, or natural (complex) mixtures, such as tragacanth, tragacanthin, bassorin, or pullulan. Other monomers with the general formula $CH_2O$, or $CH_2ONH_3$ liked through an amide, ketone, or ether bridge into polymers may be useful. Clearly various molecular weights may be useful but would need to be individually optimized to allow high lubricity with the correct oncotic pressure. In addition, various proportions and mixtures of biopolymers may be useful and/or mixtures of biopolymers and synthetic biocompatible polymers may be usefully combined and optimized for lubricity, solubility, oncotic pressure, and injectability. In addition, there are complex carbohydrate products or extracts, such as aloe vera extract, extract of quillaia, and other vegetable gums, and other mucins, such as sialic acid, or mucilaginous plant extracts, that may be useful.

Biocompatible beads (polyacrylamide solid beads, styrene-divinylbenzene copolymer beads, latex, glass nanospheres, carbon nanospheres, fluorinated graphite polymer, finely divided graphite, fuller's earth/lignosulfonate mix, or colloidal silica suspensions may also have utility, either alone or in combination with other polymers.

Several considerations support compositions containing mixtures of compounds. As noted above, high molecular weight PEG has high lubricity and very low oncotic pressure. Thus, to obtain optimal lubricity and optimal osmotic pressure, a low amount (e.g., 0.1% w/v) of PEG 8000 may be included in a formulation. Although polyvinyl pyrrolidone-coated colloidal silica (PERCOLL®) has virtually no intrinsic lubricity, it can form a strong gel with sufficient lubricity in the presence of high molecular weight polyvinyl pyrrolidone (390,000 molecular weight), carboxymethyl cellulose (700,000 molecular weight), or chondroitin (~70,000 molecular weight). Further, the addition of 0.1% PEG 8000 results in a stabilizing effect on osmotic pressure results. These gels have rheological advantages in addition to pure lubricity and are an attempt to mimic the rheological behavior of the endogenous hyaluronic acid+lubricin gel system found in the healthy joint. In addition, PVP and PVA form a weak gel in many different proportional mixtures and various molecular weights. Carboxymethyl cellulose or mixtures of carboxymethyl cellulose and hydroxylmethyl cellulose (400K) or hydroxy ethyl cellulose (1.3M) have excellent lubricity and can be made into a gel. With the addition of minimal amounts of glycol-chitosan, this gel can be made very strong. Chondroitin is mildly anticoagulating and anti-inflammatory but is not typically available in high molecular weights. It may be a useful supplement to highly lubricating high molecular weight molecules, such as PEG or other polymers, with the appropriate oncotic pressure and biological half-life characteristics. Further, when part of a gel complex, chondroitin is more likely to be retained in the joint. Also, due to charge considerations, chondroitin can gel hyaluronic acid. Chondroitin also will form a weak gel with carboxymethyl cellulose (CMC), which shows excellent lubricity and is very inexpensive relative to hyaluronic acid.

Various molecular weights may be used to formulate useful mixtures. Further, various molecular weights of polymers can be linked together to allow compositions with mixed block copolymer arrangements of carboxymethyl cellulose, methyl cellulose, glycol-chitosan, Ficoll, PERCOLL®, polyethylene glycol, polyvinyl-pyrrolidone, and/or poly(D,L-lactide-co-glucuronide), for example. Many of the polymers, both synthetic and natural, can be linked together and arranged in composite block polymers. Specifically, block polymers of PEG and PVP or PEG/PVP/PVA can be used to form a useful gel. Silicone organic copolymers are particularly flexible allowing for the optimization of molecular weight, solubility, hydration, and isoelectric point, by optimizing the mixture of blocks to achieve such optimization in almost any combination of the above synthetic, semisynthetic, or natural polymers (see U.S. Pat. Nos. 3,480,583, 3,600,418, and 5,971,809, incorporated herein by reference). A composition containing high molecular weight PEG, HEC, PVP, and PEG-tyramine is proposed to provide a gel with high lubricity and good buffering potential. In addition, many polymers usually found as rigid solids can be made with limited degrees of polymerization and can alone or in mixtures with suitable hydrophobic or hydrophilic carriers provide a biocompatible lubricating fluid formulation with appropriate half-life and osmotic characteristics. In addition, other monomers with the general formula $CH_2O$ or $CH_2ONH_3$ linked through an amide, a ketone, or an ether bridge into high molecular weight biopolymers would be useful.

III. POLYETHYLENE GLYCOL FORMULATIONS

PEG as an agent for intraarticular injection is only practically useful under a restricted range of molecular weight and percent compositions. Low molecular weight PEG will flow out of the fenestrated epithelia of the synovia and be diluted in the body. High molecular weight PEG, similar to other high molecular weight molecules in the synovial fluid, would be retained. For lubricating utility, a restricted range of PEG molecular weights and percent formulations defines a unique range of compositions with a liquid fluid state in the aqueous environment and temperature of the target joint, and which are likely to be retained in the joint.

As a means to define these effective formulations, and since lubricity is proportional to both PEG or PEO concentration and PEG or PEO molecular weight, an "effective concentration" (AU=arbitrary unit) may be calculated by multiplying concentration of PEG or PEO (as a percent) by the molecular weight of the PEG or PEO. As an example, a 6% PEG 600K formulation would have an effective concentration of 3.6M. This unitless effective concentration also allows for comparison of various PEG or PEO products.

In addition, the hydration properties of PEG by itself may not be sufficient to remain a liquid at the concentrations given and at the temperature of the joint and thus mixed compositions may be needed (see Examples 8 and 9). Further, under highly specialized conditions, low molecular weight compositions may be useful formulations independently or as adjuncts to intraarticular injection (see Example 9).

A. Colligative Properties of PEG Vs. Albumin

Albumin is the major osmolite in serum and is normally 4% to 6% of serum by weight. The molecular weight of albumin (66K) prevents it from crossing capillary epithelia, glomerular epithelia, synovial epithelia, etc. Thus, as fluid under pressure carries salts through capillary epithelia, albumin is retained and concentrated in the capillary lumen (terminal vessel of the circulatory system). Concentrated albumin induces an oncotic pressure that opposes the effect of blood pressure, thus pulling water back into the lumen. The joint space has similar dynamics. Mechanical weight bearing generates considerable hydrodynamic pressure (analogous to blood pressure) expelling fluid and low molecular weight molecules from the joint. Thus, the osmotic pressure of the joint retains a fluid phase in the joint. Therefore, any PEG-based product of the present invention must match or be below the serum albumin oncotic pressure to prevent joint swelling.

As such, the colligative properties of various molecular weight PEGs were compared with 2.5% albumin and the effects were observed in a dialysis model. Since neither the PEG nor the albumin can move through the 3 k membrane, water must enter (or leave) the bag until equal oncotic pressure is achieved. Thus, if the oncotic pressure of the PEG solution was lower than the oncotic pressure of 2.5% albumin, then the dialysis bag would shrink. If higher, then it would swell.

Both the 5K and 17.5K PEG with 3% and 4% "albumin equivalents" showed shrinkage (loss of weight) of the dialysis bag when immersed in a 2.5% albumin solution. For both molecular weights of PEG, the 1% and 2% "albumin equivalents" solutions showed swelling (increase in weight) of the bag. The long extended super-hydrated PEG molecule has humectant properties and yet can also precipitate proteins by excluding water; however, these properties did not interfere with the predicted colligative properties of PEG. PEG demonstrated colligative properties inversely proportional to molecular weight. Thus, high molecular weight PEG allowed for a higher percentage of PEG to be used by weight to achieve the same oncotic pressure. Thus, for a fixed target oncotic pressure, higher molecular weight PEG would allow for a higher percentage of PEG to be used. In addition, higher molecular weight PEGs have intrinsically higher lubricity per unit weight.

B. Freezing Point Depression

Mixtures of PEG and co-solvents were studied to optimize lubricity while still producing a liquid at 34° C. with the expectation that the solubility (freezing) at 34° C. would follow a similar pattern based on co-solvent effects or colligative properties, regardless of temperature. The solutions containing 32% PEG 17.5K were prepared that also contained 0.18% Fuller's earth in order to prevent possible supersaturated solutions.

The experimental freezing replicates were significantly different from the 32% PEG 17.5K+PBS control as determined by Wilcoxon non-parametric matched pairs test: 1% PEG 5K, $P<0.01$; 1% ethanol (EtOH), $P<0.01$; and 1% DMSO, $P<0.01$. The addition of 1% PEG 5K, 1% ethanol, and 1% DMSO all depressed the freezing temperature (Example 3).

C. Lubricity

The lubricating ability of synovial fluid is important and can be studied in ways similar to other lubricants. The lubricity of various PEG solutions was tested using the break angle lubricity test by measuring the angle where movement of a pre-weighed stainless steel nut first occurred. Higher molecular weight PEGs provided greater lubricity when between 17K and 400K. It was found that the lubricity of PEG is proportional to molecular weight until viscosity dominates the break angle method at about 400K. Molecular weights above 400K had significant viscosity effects that affected the interpretation of the break angle test method.

Next, the scar test method was used to determine lubricity of high molecular weight PEG. This method was modified from the EU ISO ref: EN 590 Diesel Fuel Standard Generally Applicable Requirements and Test Methods (Scar test=EN ISO 12156-1). A 'Dremel' tool was used to apply weight and rotational force to a fixed aluminum test platform with 250 µL of each test lubricant applied in a 2 cm×2 cm patch directly under the tool. A medium setting and a brass brush were applied to the aluminum target surface for 5 sec. The progression of scar sizes were as follows: 1% PEG 200K>9% PEG 200K>5% PEG 600K>4% PEG 600K. In the scar test the smaller the scar the better the lubrication.

Lubricity was found to be proportional to molecular weight and concentration. The inclusion of 7.5% PEG 200K in the 4% PEG 600K solution visibly lowered the viscosity and also demonstrated the best lubricity by the scar test.

In addition, the inclusion of a small amount of PEG 100K lowered the viscosity of 6% PEG 600K. Without this addition, 6% PEG 600K is very stiff. When 6% PEG 600K+1% PEG 100K was compared to 6% PEG 600K alone, the 6+1 mixture showed superior flow (lower viscosity) at room temperature. Furthermore, a mixture containing 6% PEG 600K+1% PEG 100K showed improved lubricity as measured by the scar test when compared to 7% PEG 600K. Thus, compositions containing mixed PEG/PEG can provide enhanced lubricity and allow the use of higher molecular weight PEGs.

D. Survival Time in the Knee Joint

In order to characterize the half-life of high molecular weight PEG in the rat knee in vivo, a radioactive iodine ($I^{125}$)-labeled PEG 600K was prepared and injected into the left knee of a 250 g female Wistar rat. A decay curve was developed over a period of 12 days using a Geiger-counter. The rat was held still each day and radioactive activity, measured as counts per minute, was measured at the surface of the knee.

The log scale plot fits a liner decay model showing approximately a 5% decrease per day. Therefore, the half-life of $I^{125}$ PEG in vivo was approximately 12 days. As there is no known metabolic pathway for the destruction of PEG, gradual diffusion out of the joint with passive elimination through the kidney seemed most likely. Regardless of the mechanism of removal, the half-live is equal to or greater than 12 days. This long half-life exceeds the half-life of hyaluronic acid, which is generally taken to be 24-48 h (Stern, 2004; Genitrix HY50® Datasheet).

E. Rat Model of Osteoarthritis

Six percent PEG 600K with 1% PEG 100K provided good lubricity, low toxicity, prolonged half-life in the joint, and acceptable oncotic and physical parameters. Therefore, this composition was tested in vivo using an established rat model of osteoarthritis based on the well-described activity of mono-sodium iodoacetate (MIA) (Rosenthale and Capetola, 1982; Conforti et al., 1991; Clarke et al., 1997; Guingamp et al., 1997; Uebelhart et al., 1998; Bove et al., 2003; Neugebauer et al., 2007; Al-Saffar et al., 2009; Tang et al., 2010).

Briefly, MIA is known to interfere with glucose metabolism. Specifically, it interferers with mitochondrial function to the extent that the mitochondrial-dependent variant of the apoptotic cascade is activated. This is particularly important for chondrocytes. In the joint, MIA induces metabolic arrest of the chondrocytes and death proceeds with pyknotic nuclei appearing over the course of 3-7 days. There is little inflammation and the loss of HA and other glycoprotein components of the cartilaginous matrix results in continued and progressive mechanical damage. Histologic changes are best demonstrated after 14 or more days. In these experiments, all animals, both controls and treatment groups, received MIA to cause equal damage to the joints. Treatments injections were typically given after 10-14 days.

Figure 3:
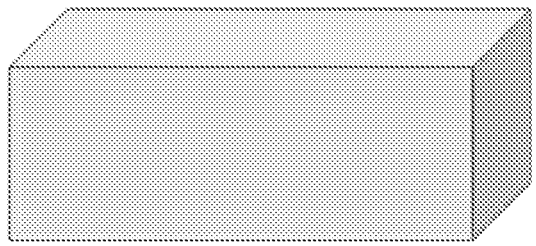
FIG. 3 shows the mobility assessment tool.
Figure 3:
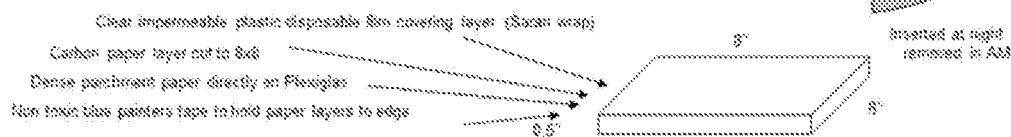

The monitoring tool diagramed in FIG. 3 was used as a quantitative measure of rat mobility with the following modifications. A dense polypropylene sheet was glued on to an aluminum frame to provide a rigid waterproof top layer. The second layer consisted of 60 grit sandpaper with the points facing down. The third layer consisted of photo quality matte printer paper. The fourth layer consisted of carbon paper with the carbon facing up. The fifth layer is a smooth ceramic tile surface cut into an 8"×8" square to provide a stable platform for foot print monitoring. The monitors were collected each day after overnight unrestricted spontaneous movement (18-24 h). The "dots" on the monitor paper were counted using image analysis software (AlphaView SA, Informer Technologies, Inc.) with the 'colony count' tool, using fixed contrast and threshold settings, to provide consistent colony counting for all days throughout the study period.

Figure 4:
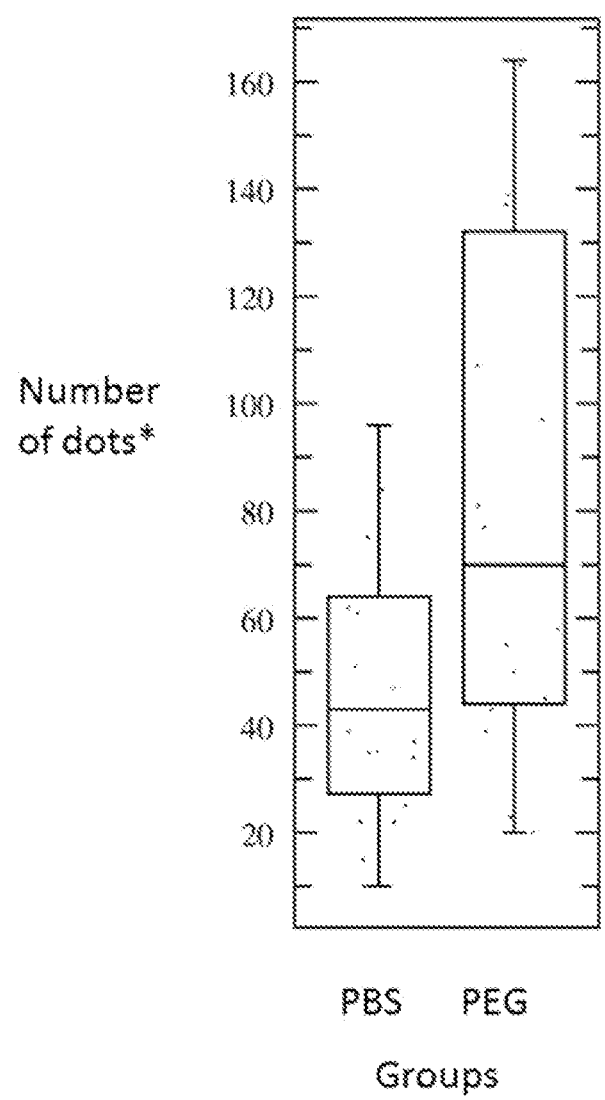
FIG. 4 shows mobility of MIA-treated rats that were treated with PBS alone or 6% PEG 600K+1% PEG 100K in PBS. Each box plot shows 50% within the box and 25% in each wing. The median is within the box. *=number of dots counted on individual days. Two rats (each monitored independently) in each group.

The first comparison was phosphate buffered saline (PBS) as the negative control vs. 6% PEG 600K+1% PEG 100K as the test agent. One hundred microliters of PBS or the PEG mixture were given to each group. The goal of the negative control was to see if the test material was better than the baseline negative control. The PEG group showed significantly higher (P=0.006) counts when compared to the control (FIG. 4; Table 6). This indicates higher spontaneous mobility in the PEG group. MIA-induced chondrocyte death is irreversible and MIA was given here starting 15 days prior to PBS or PEG treatment. Thus, joint pain is likely the major determinant of the differences in counts between the groups. Without being bound by any theory, PEG in not known to directly affect pain or sensation and therefore superior lubrication is the likely explanation for the reduction in pain. This short-term rat model is only capable of detecting behavioral (pain) responses. Superior long-term lubrication has the potential to modify the course of osteoarthritis by preventing ongoing mechanical damage. Since chronic low grade mechanical damage is known to be sufficient to induce osteoarthritis, decreasing mechanical damage would decrease the progression of osteoarthritis over time.

F. PEG Mixtures

A mixture of different molecular weight PEGs offers potential advantages. For example, 6% PEG 600K+1% PEG 100K demonstrated superior lubricity when compared to 7% PEG 600K. Similarly, 4% PEG 600K in 7.5% PEG 200K demonstrated superior lubricity when compared to 6% PEG 600K. High molecular weight PEG in a lower molecular weight PEG base is an example of the co-solvent effect. High molecular weight PEG, a long linear polymer, becomes more soluble in PEG of a lower molecular weight due to weak force PEG-PEG associations which favor an open linear form of the high molecular weight PEG vs. the high molecular weight PEG by itself, excluding water, and remaining in a ball. An example of this is when a PEG-modified protein partitions into a 4.5% PEG 5K/PBS solution vs. a matched molecular weight 4.5% Dextran 5K/PBS solution, allowing the measurement of the degree of PEG coupling (Scott et al., 1988; Herold et al., 1989; Tarrand et al., 1989; Scott et al., 1989; Harris, 1992; Delgado, 1993; Delgado, 1997; Fee and Van Alstine, 2006; Pasut and Veronese, 2009). This enhanced solubility allows a higher fraction of PEG to be incorporated into a formulation without increased viscosity. Similarly, higher molecular weight PEGs become more practical when using this co-solvent approach. A preferred embodiment may include PEG 600K-10M in a mixture of PEG 100K-600K. If the bulk consists of a medium and a low molecular weight, then this should optimize the lubricity of the high molecular weight material while maintaining the necessary fluidity suitable for injection. For example, PEG 1.8M would provide superior lubricity than PEG 600K; however, the solubility of PEG 1.8M would typically limit its practical utility in an aqueous environment. Useful compositions based on the above experimental observations are promising. An example would be 0.5% PEG 1.8M dissolved in 4% PEG 600K+1% PEG 100K. These high molecular weight PEG mixtures, containing a component of >600K) can be dissolved in PEG 400K+PEG 100K in water with the addition of DMSO. Subsequently, the DMSO can be removed by dialysis vs. water and then changed into an iso-oncotic PEG 400K or PBS, sorbitol, glucose, ringers lactate, or another iso-oncotic aqueous base solution. Compositions of PEG 600K-10M at between 0.01% to 6% in an environment comprising substantial amounts of PEG 100K-600K to more than one million molecular weight at between 0.1% and 5% and in a solvent system based on low molecular weight PEG from 260-100K at between 0.1% and 10% will provide a highly lubricating biocompatible and injectable composition with a long biological half-life. A preferable example would be 0.5%-2% PEG 1-2M, 0.5%-2% PEG 600K, and 1%-4% PEG 100K. More preferable still would be 1% PEG 2M wetted with DMSO and slowly added (1 to 3 days), with constant mixing, to an aqueous solution of 2% PEG 600K and 2% PEG 100K. Subsequently, DMSO is removed by dialysis into PBS. The material requires gentle heating prior to injection. All percentages represent weight/volume in PBS, pH 7.4. Also provided is a room temperature formulation comprising 2% HEC (1.3M molecular weight), 1% PEG 100K, 2% PEG 600K, and 2% PEG 2M. This was made by first dissolving HEC in water, on wet ice overnight, then adding PEG 100K for 3 h, PEG 600K for 3 h, and finally 2% PEG 2M overnight at room temp with slow tumbling. Finally, 0.6% NaCl was added, and the mixture was sterilized by three cycles of Tyndallization at 80° C.

G. PEG Mixtures with Other Highly Hydrated Molecules

PEG provides excellent lubricity, good retention in the joint, and a well-known low toxicity. Other highly hydrated molecules may also offer advantages in the joint space. The amount of PEG that can be put into the joint is limited to some extent by its stiffness. However, the inclusion of other highly hydrated molecules may ameliorate this limitation. The inclusion of hydroxyethyl cellulose (HEC) or hydroxypropyl cellulose (HPC), and/or polyvinyl alcohol (PVA), and/or polyvinylpyrrolidone (PVP) would maintain or improve solubility and lubricity and also provide better flow characteristics. When a small amount of PVP (1.3%) was included in mixtures with high molecular weight HEC (1.3 million, 2%), the viscosity of the material was markedly reduced. The inclusion of 1.3% PVP (360K) added to 2% HEC mixtures, plus 9% PEG improved the flow characteristics of these mixtures. Thus, improved injectable composition with high flow, low toxicity, prolonged half-life, and improved lubrication would be feasible since the inclusion of the highly hydrating molecules also allows the solubilization of higher molecular weight PEG. Hydroxyethyl cellulose, methylcellulose, and hydroxypropyl cellulose are used with cosmetic and hydrophobic drug formulations to improve the drugs' dissolution. This process is known as "hydrophilization." These high molecular weight compounds have low toxicity and due to the lack of a metabolic pathway would be retained in the joint space (NIH, Specialized Information Services). Better hydration properties appear to allow increased concentrations of PEG to be incorporated. Further, better hydration of these PEG-based compositions should allow for better oxygenation and nutritional flow to the joint. Various fractional mixtures of high molecular weight PEG 1-10M (0.001% to 1%), in a substantial amount of PEG 600K (0.5% to 12%) and HEC (0.5% to 12%), and containing PVA or PVP (0.1% to 12%) will allow improved solubilization of the high molecular weight PEG and provide superior injectable lubricating biocompatible non-toxic compositions with good flow and a long biological half-life. Nine percent PEG 600K+2% HEC 1.3M+1.3% PVP 360K has been composed as an example. Clearly, there are several classes of well-hydrated, biologically tolerated, molecules that may be considered as adjuncts to PEG. These include synthetic, semisynthetic, and natural polymers. PEG-PVP is a good example of a synthetic mixture having the unique advantage of a gel property. PEG-HEC-PVP as discussed above would be a synthetic and semisynthetic mixture. Molecules such as dextran, polyglucosamine (chitosan), agarose, pullulan, and xanthan gum, mixed with PEG would be examples of synthetic—natural polymer mixtures. These high molecular weight natural polymers can be very stiff but have usable flow/viscosity in the 0.1%-5% range. These molecules would be chosen to promote hydration and solubility of high molecular weight PEG. They would not be metabolized, would be of a high molecular weight making them unlikely to be cleared from the joint, would have low oncotic pressure, and would remain liquid at joint temperatures. A preferred example would be 1% PEG 1-2M, 0.1%-4% HEC 1.3M, 0.1%-4% PVP 360K. More preferable still would be 1% PEG 2M wetted with DMSO and slowly added, with mixing, to an aqueous solution of 1.5% HEC 1.3M and 1% PVP 360K. Subsequently, DMSO is removed by dialysis into PBS. The examples proposed here have PEG levels well below the 10 mg/kg/day safe level for this GRAS compound (Harris, 1992; Herold et al., 1989). HEC is similarly non-toxic and classified as GRAS (Anon, 1986; GRAS food ingredients). Also PVP is a GRAS compound and has been used as a volume expander (NIH hazardous substances database; Cayton and Clayton, 1993).

H. Very Low Molecular Weight PEG

It is posited that the very low molecular weight PEGs (170-400 MW and up to 200K MW) would not be injected directly into the joint but instead be administered systemically, e.g., used in an intravenous infusion, intravenous bolus, subcutaneous or IM deposition, or by an intarperitoneal bolus injection, or be given orally. PEG 400 is a liquid at room temperature and has been used as a solvent in pharmaceutical mixtures. Further, PEG 400 has low toxicity. Monkeys given 7 g/kg/day of PEG 400 for 3-4 weeks developed a reversible hepatitis in 50% of animals (Lockard et al., 1979). This dosing level used in monkeys equates to 490 g/day in a 70 kg man. Clearly, this is a massive dose. In contrast, 700 mg/kg I.V. in rats (49 g/70 kg man) blocked loss of function in a brain trauma model with no toxicity (Koob et al., 2005). PEG 400 is incorporated in many injectable pharmaceuticals and is generally well tolerated. PEG given IP has been documented to promote neural regrowth by reducing inflammation (Shi and Borgens, 1999; WHO publication found on the world wide web at inchem.org/documents/jecfa/jecmono/v14je19.htm). Thus, direct dosing of low molecular weight PEG would allow diffusion into small joints with potential benefits of lubrication and reduced inflammation and is a feasible osteoarthritis treatment. Low molecular weight polyethylene glycols between 238 and ~100K would pass through the epithelia and into small joints. As an example, a 140 mL intraperitoneal bolus of 50% PEG 400 (700 mg/kg) would diffuse only slowly out of the IP compartment and would be well below any documented toxic range for PEGs between about 238 MW to about 8000 MW. PEG 400 will have minimal osmotic impact since it distributes in total body water, and indeed is used as a tracer of body water (van Wijck et al., 2012). Thus, one familiar with the art can reasonably expect that PEG between 238 (pentaethylene glycol) and about 100K molecular weight would have utility in osteoarthritis in the small joints by a lubricating and/or anti-inflammatory mechanism. These compositions could be administered in aqueous biocompatible solutions. For example, iso-osmotic PEG in water or saline or PBS by infusion of up to 60% (w/v) PEG 400 in saline, PBS, ringers lactate, glucose or other common half-strength or quarter-strength salt solution to be given intravenously by infusion or slow bolus or as an intarperitoneal bolus. Further, formulations involving low molecular weight PEG (about 400 to about 24K MW) with the inclusion of intermediate weight PEG (about 50K to about 300K) should have advantages. The intermediate molecular weight PEG should be able to diffuse into large joints since large molecules like immunoglobulin get into normal healthy joints to some degree by diffusion through the fenestrated epithelia. This should provide utility as a treatment for small joints and as an adjunct treatment to the simultaneous intraarticular injection of high molecular weight PEG mixtures into the large joint proposed above. The inclusion of a small amount of higher molecular weight PEG in a large IP bolus would tend to slow the osmotic swelling of the bolus site and thus slow diffusion out of the bolus to provide more sustained delivery. Alternatively to the intermediate PEG 50K to 300K outlined above, a variety of other pharmaceutically acceptable materials such as dextran, hydroxylethyl starch, branched or multi-arm PEGs, or very high molecular weight PEG (1-12M), and a variety of well tolerated natural polymers such as, polyglucosamine, polysaccharides, and other carbohydrates, carboxymethyl cellulose, hydroxyethyl cellulose and other semi-synthetic polymers could serve this same function of facilitating prolonged release of low molecular weight PEG.

In summary, low molecular weight compositions that provide lubrication, have anti-inflammatory characteristics, are biocompatible, and can be given IV, by slow bolus infusion, by periodic subcutaneous injection, by IM or intra-peritoneal injection/deposition, or even administered orally, may provide sustained treatment of small joints. For example, 10%-60% PEG 400 (w/v) in half-strength saline administered by IP or IV bolus, with a preferred embodiment being 20%-60% PEG 400, plus 1%-30% PEG 8K in half-strength saline given IV. Another embodiment may be 50% PEG 400, plus 5% PEG 8K, plus 8% PEG 100K molecular weight in half-strength saline given by IV bolus. The most preferred embodiment is a simple oral formulation of one or more PEGs of low molecular weight (e.g., PEG 400) and given at an appropriate dose and dose schedule of ~1 to 300 gram per day, with or without an osmotic stabilizer to ensure slow release, for example, 10-30 grams PEG 400 taken orally as a 5% solution in juice 1-2 h before meals, once or twice per day.

I. PEG in Mineral Oil

Compositions based on alkanes, such as mineral oil and the oxygen-carrying fluorinated hydrocarbons (FLUORINERT®), and a high molecular weight PEG, and emulsifying agents such as, steryl alcohol, phosphatidylcholine, oleic acid, oleyl alcohol, hydroxyl stearate, cetyl alcohol, myristyl lactate, isopropyl myristate, and/or biocompatible natural polymers, such as agarose, alginate, carrageenan, guar gum, locust bean gum, xanthan gum, or synthetic polymers, such as PEG or hydroyethyl cellulose, and/or detergents, such as CHAPS, TWEEN® 80, NP40, or sodium cholate, or silicone oils, would assist in forming dispersed emulsion composition(s) that are water insoluble. These mixtures offer high lubricity and would not diffuse out of the joint due to their hydrophobic nature and thus provide biocompatible hydrophobic lubricants. Compositions of mineral oil+phosphatidylcholine in PEG; or mineral oil+phosphatidylcholine in ethyl acetate; mineral oil+phosphatidylcholine+hydroxyethyl cellulose in PEG 400 are of particular interest since the inclusion of phosphatidylcholine as an emulsifying agent seems to significantly enhance lubricity. More preferably steryl alcohol can be used as the bulk solvent: steryl alcohol+PEG+phosphatidylcholine+polyvinylpyrrolidone+ polyvinyl alcohol+polysorbate 80. More preferably still, high molecular weight PEG+steryl alcohol+phosphatidylcholine+polyvinylpyrrolidone+polyvinyl alcohol+polysorbate 80+petroleum jelly in a silicone oil based solvent. Several preferred hydrophobic compositions are as follows: A [3 mL mineral oil; 7 mL PEG 400; 0.25 g PEG 200K; 0.75 g PEG 600K; 0.1 g TERGITOL® NP40] or B [3.5 g lecithin; 6 mL mineral oil; 0.5 mL FLUORINERT® 70; 0.1 g NP40] or C [10 mL PEG 400; 1 g phosphatidylcholine; 0.1 g petroleum jelly] or D [10 mL PEG 400; 1 g phosphatidylcholine; 0.56 g polyvinylpyrrolidone; 0.1 g petroleum jelly] or E [1 mL steryl alcohol; 0.5 g PEG 600K; 0.01 g PEG 2M; 0.5 g phosphatidylcholine; 0.1 g polyvinylpyrrolidone; 0.1 g polyvinyl alcohol; 0.01 g plysorbate 80; 0.9 mL high molecular weight silicone oil].

The breaking lubricity of material D [10 mL PEG 400; 1 g phosphatidylcholine; 0.56 g polyvinylpyrrolidone; 0.1 g petroleum jelly] was tested in an identical manner to the above studies, and showed a break angle of 7.5 degrees (average of 12 measurements). Furthermore, material D is non-miscible in water. The composition requires heat (in an 80° C. bath with mixing until fully dissolved) and then a quick cool (in an ethanol-dry ice bath) for stable storage at −70° C.

Clearly various ratios of phosphatidylcholine (PC) to Petrolatum with the addition of the emulsifiers, oleic acid, hydroxyl-stearate, natural or synthetic or semisynthetic polymers, and or biological detergents can achieve, a stable emulsion that is biocompatible and highly lubricating. Similar emulsifiers are found in some cosmetic applications. A preferred composition is 10 mL PEG 400+1 g phosphatidylcholine+0.56 g PVP 360K+0.1 g petrolatum. The composition is formed by slow mixing at 80° C. and then snap freezing at −70° C. By quick reheating in an 80° C. water bath, an opalescent yellow viscous fluid is again quickly regenerated. This material must be kept at 35° C. prior to injection. Surprisingly, this material had one of the highest lubricities measured of any composition tested so far. This formulation, when exposed to water, forms a hydrophobic/hydrophilic boundary layer similar to the behavior of normal articular cartilage and has high lubricity. It is noteworthy that natural cartilage is not particularly strong. Cartilage avoids ware and degeneration, at least in part through the exceptional lubricity of the phospholipid-dependent hydrophobic/hydrophilic boundary layer found in the normal joint. The boundary layer has been measured and functions with about 1000-fold less friction compared with that of the best ball bearing systems (Bove et al., 2003; Gale, 2007; Necas et al., 2008). Simple compositions of mineral oil and various mixtures of PEG (Composition A) have good lubricity and form a strong gel that may distribute impact in the joint. Similar compositions but with the addition of phosphatidylcholine showed improved lubricity (Compositions B and C). A preferred composition includes polyvinylpyrrolidone: 10 mL PEG 400+1 g phosphatidylcholine+0.56 g polyvinylpyrrolidone+0.1 g petrolatum, which forms a stable dispersed solution as opposed to an emulsion, can be stored indefinitely (after being snap frozen), and has high lubricity as measured using the break angle test. A further more preferred embodiment replaces petroleum jelly or mineral oil with steryl alcohol and lubricity is enhanced with the addition of PEG (high molecular weight), steric acid, phosphatidylcholine, polyvinylpyrrolidone, and polyvinyl alcohol, and stability is enhanced with steric acid and TWEEN® 80 as emulsifiers. Similar, compositions but using a mixture of silicone oil (molecular weight >17K, e.g., 17K to 2M) with the addition of phosphatidylcholine, HEC, and emulsifiers should have good stability, lubricity, and biocompatibility. These silicone-based compositions also form an exceptionally high lubricity boundary layer with water. Similar compositions based on steryl alcohol and or silicone, with PEG, phosphatidylcholine, and gelation based on PVP/PVA, chondroitin/gelatin, chitosan/CMC, or (CMC, or HA, or PVP or PVA or agarose) or one or more of these polymers and the synthetic PEG-tyramine (see Example 15) can be used to form a gel. These charged compositions have the advantage of forming a strong polar/non-polar boundary layer at the cartilage surface. The inclusion of specialty water soluble silicones, i.e., LK-Aquaseal-40, with transient water miscibility until $CO_2$ exposure, should further enhance the formation of high lubricity silicone-based water/oil boundary layers. Emulsions of phosphatidylcholine in petroleum jelly or pure 100% petroleum jelly may be the simplest and most effective hydrophobic compositions. For example, a 10% solution of phosphatidylcholine may be made in DMSO with heating and then diluted 1:100 in petroleum jelly to yield a stable 0.1% phosphatidylcholine solution in petroleum jelly. These emulsions may require the use of specialized pre-warming and mixing procedures. They would have low toxicity, high lubricity, and persist in the joint due to hydrophobicity. This would be a practical embodiment for those individuals with advanced disease, referred to as 'bone on bone' osteoarthritis, where most or all of the cartilage has been lost. In this setting preservation and nourishment of cartilage is no longer the goal and a pure lubricant would be desirable. Thus, a simple mixture of silicon oil and 0.6 to 6% PEG (600K to 8M) with 0.1 to 1% phosphatidylcholine would be advantageous by providing lubricity and yet would not affect nutrition of the 'bone on bone' joint.

J. PEG-coupled Antimicrobials

Rare cases of arthritis mimicking osteoarthritis have been linked to chronic subclinical *chlamydia* infection. These usually follow a sexually transmitted disease; however, many species of *Chlamydia, Chlamydophila, "Chlamydia-like organisms"* and Legionellaceae are completely dependent on amoeba for their survival in the environment and are not currently cultivatable. Thus, a formulation with both lubricating properties and the ability to deliver antimicrobials is envisioned. Antimicrobial delivery can be accomplished by an adsorbent, such as nano-carbon or nano-silica, by the use of an ionic interaction-based complex, or by antimicrobial coupling to a polymer so as to slowly release antimicrobials into the joint (Nayak and Jain, 2011). These antimicrobial releasing adsorbents, complexes, or covalently-linked antimicrobial and polymers can be formulated as part of a mixture containing a lubricating component and an antimicrobial component suitable for intraarticular injection or can be composed of the covalently coupled antimicrobial—polymer as a sole agent. PEG-based materials provide useful examples.

Clarithromycin and Moxifloxacin are antimicrobials with high activity against *Chlamydia* and *Legionella*. The susceptibility of *Chlamydia* to Clarithromycin or Moxifloxacin is in the 5-50 ng/mL range (Cross et al., 1999; Rihl et al., 2006). As shown below, both antimicrobials are nucleophiles and would not be ionized at the alkaline pH of the joint but would be reversibly bound to a weak poly-acid, such as carboxymethyl cellulose. A mixed composition can be formulated to include about 0.1%-1% high molecular weight PEG and 1%-4% HEC with the addition of 0.01%-1% CMC and the inclusion of about 1 μg to about 1 g of an antimicrobial. This material is a strong gel and the vast excess of CMC favors ionic association between the nucleophilic antibiotics and CMC. This material would provide a high molecular weight CMC acting as a Lewis acid in the joint, which would reversibly bind significant amounts (1-100 mg) of Clarithromycin or Moxifloxacin resulting in a slow-release formulation. CMC is also highly hydrophilic, acts as a good dispersing agent for PEG, is non-toxic, and is itself highly lubricating. In a second example, PEG can be activated with CNBr in alkaline conditions followed by nucleophilic attack by the nitrogen of Clarithromycin. The resultant iso-urea bonds will slowly decay, thus regenerating the Clarithromycin, which will be slowly delivered to the joint. These formulations can be used to provide lubrication, retention in the joint, low toxicity, and a slowly-released form of Clarithromycin, Moxifloxacin or other nucleophillic antimicrobials to treat Chlymidiaceae, Legionellaceae, *Mycoplasma* and other mollicutes, other "*Chlamydia*-like organisms" and septic arthritis due to other bacteria. All organisms producing septic arthritis elicit an inflammatory response, lower the pH of the joint, and thus promote apoptosis of cartilage, and once lost, adult cartilage has no regenerative potential. Thus, the anti-inflammatory activity of PEG should have a role in acute septic arthritis as well as in chronic septic arthritis do to rare, unusual or opportunistic organisms.

K. Gelation and Rheological Behavior

As outlined above, an optimized composition will mimic the gel effect of the native joint hyaluronan/lubricin gel system. The optimal gel distributes the shock load at rest, but provides a low viscosity and high lubricity fluid flow when in motion. These requirement restrict the compositions to a unique range of acceptable molecules with low toxicity, prolonged half-life, low metabolism, low oncotic pressure at the concentrations needed to provide high lubricity, acceptable function in the aqueous environment of the joint, and most critically to those few compositions that provide functional lubricity, and yet additionally provide a rheologically shear-sensitive gel. Rheologic properties describe non-Newtonian fluid flow. Compositions identified herein form a strong gel at rest yet flow rapidly under pressure-induced shear-stress.

Many of the compositions presented herein are highly hydrated polymers that are readily soluble in aqueous solvents, and include semisynthetic polymers, such as methylcellulose, carboxymethyl cellulose, hydroxyethyl cellulose, or synthetic polymers, such as polyethylene glycol, polyvinylpyrrolidone, and similar molecules, and include natural polymers, such as dextran, polyglucosamine, gelatin, xanthan gum, pullulan, and similar molecules. These compounds are generally well tolerated biologically. Certain polymer pairs were identified that yield compositions capable of forming a gel with the desired rheologic behavior.

Many combinations were studied but only restricted subsets that form gels were identified: 1% CMC 700K in water modified with 0.3% chitosan ~100K, 0.1% chitosan ~100K, 0.5% PVP 360K, 3% PVP 360K, 0.5% HEC 250K, 0.5% alginate ~100K, 0.5% chondroitin 30K, 0.1% phosphatidylcholine, 0.1% gelatin, 0.1% agarose, or 0.25% 600K PEG-tyramine; 1.5% HA 1.5M in PBS modified with 0.6% chondroitin ~30K or 0.1% heparin sulfate. 40K; 2% HEC 1.3M in PBS modified with 1% PVP 360K, 0.3% alginate ~100K, 0.3% CMC 700K, 0.1% heparin sulf. 40K, 5% PERCOLL® (1% w/w), or 1% phosphatidylcholine; 2% HEC 1.3M in water modified with 0.1% chondroitin 30K; 1% HEC 1.3M in water modified with 0.33% PVA 195K or 6% PVP 360K; 6% PEG 600K in water modified with PBS; 2% PEG 600K in water modified with 1% chondroitin, 1% HEC 1.7M, 0.5% chitosan, 0.5% agarose, 0.5% CMC 700K, or 6% PVP 360K; 4.5% PEG 600K in water modified with 1% PVA 195K; 0.5% PVA 195K in PBS modified with 0.01% NaBorate500; 5% PVA 195K in water modified with 6% PVP 360K; 6% PVP 360K in PBS modified with 5% PERCOLL® (1% w/w).

Many of the polymers listed above will form highly viscous solutions at high concentrations. Therefore, gelation was assessed at a low concentration and by comparing the base polymer at a percentage composition giving moderate viscosity with the addition of a second polymer at a lower percent concentration such that it had an equal or lower viscosity when compared to the base polymer. If the composition is obviously stiff when the two fluids are mixed, then it is said to have formed a strong gel, which was arbitrarily taken to mean that neither parent solution could support its weight under gravity when inverted but the mixture could support its own weight.

In addition, many combinations were tested that did not gel. In general, both ionic and non-ionic gels were identified. For example, CMC is a poly-acid, usually sold as a sodium salt. When CMC was combined with a poly-base, such as polyglucosamine chloride (chitosan), a strong gel with a neutral pH formed. Presumably gelation was due to ionic interactions favoring larger (non-covalent) interactions. Usually a gel is thought of as made up of a fluid component and solid phase. In this case the solid phase is not a crystalline solid but amorphous solid with equilibria favoring intermolecular association.

In addition, several non-ionic gel combinations were identified, such as HEC/PVP, HEC/heparin, HEC/chondroitin, HEC/CMC, HEC/HA, PEG/PBS, PEG/CMC, PVA/PVP, and HEC/PEG-tyramine. Although polyvinylpyrrolidone has an internal quaternary amine, it is non-ionized under normal conditions (Oster, 1952; McDonald and Spitzer, 1953), although it will decompose in strong acid (Grass et al., 2008). Thus, the mechanism of gelation likely involves small displacement of charge since HEC, PVP, and PEG are non-ionizing. PVP has low toxicity and has previously been used as a plasma volume expander (Trimpin et al., 2001).

Furthermore, and in addition to the identified gel systems, a restricted set of these gels demonstrated favorable rheological properties, meaning a significantly increased flow rate under shear force. Rheology is the study of non-Newtonian fluid behavior in soft solids, such as gels. Newtonian fluids can be characterized by a single viscosity (resistance to flow under pressure) for a specific temperature regardless of changes in the pressure gradient. Non-Newtonian fluids show changing viscosity induced by shear under a force; frequently termed shear stress, or strain, of the fluid. Here, rheological measurements were made by comparing the flow rate (mL/min) under gravity from a vertical 10 mL pipette, using a 23.7 cm (10 mL line) head pressure, to the flow rate under shear stress conditions. Shear stress was obtained by measuring the inflow rate when the material was drawn into the same size pipette using a constant vacuum (100 mmHg).

The results shown in Table 8 are given as a ratio: (flow rate gravity condition)/(flow rate under shear stress condition). This provides a simple way to contrast flow of a gel mixture at low shear stress to the same gel mixture under high shear stress.

Interestingly, a small amount of PERCOLL® (5% v/v) induced a strong gel with HEC that had desirable rheological properties. One-hundred percent commercial PERCOLL® is 23% colloidal silica coated with PVP in water. Thus, a mixture containing 5% PERCOLL® contains ~1% colloidal silica/PVP by weight. However, neither the addition of PVP alone nor micrometer size silica slurry alone resulted in any detectable change in rheological properties of the HEC base material. Further, it should be noted that 100% PERCOLL® demonstrates no detectable lubricity or viscosity above that of water.

To further explore synthetic polymers with high lubricity and low toxicity and to further explore the benefits of in situ gelation, the monosodium iodoacetate (MIA) osteoarthritis animal model described above was again used. All rats received equal exposure to MIA and a post-MIA baseline was measured. One hundred microliter intraarticular injections of PBS vs. 9% polyvinylpyrrolidone (PVP) 380K in PBS vs. 9% PVP in PBS with the addition of 5% (v/v) PERCOLL®. PVP plus PERCOLL® had been previously determined to give a strong gel effect.

After nine days of monitoring, both the PVP and PVP/PERCOLL® groups showed higher post treatment counts when compared with PBS (see Example 12). PVP has less lubricity and less viscosity at the 9% level than 6% PEG. Furthermore, PERCOLL® has no intrinsic lubricity and is not detectably different from water even at the 100% level. Therefore, the improved result with the addition of PERCOLL® demonstrates the advantages of the gel effect alone, in isolation from other factors. A 56% increase in average counts was seen in the PVP/PERCOLL® group.

L. Synthetic and Natural Polymer Mixtures

In Example 8 it was noted that a large number of potential mixtures of synthetic, semisynthetic, and natural polymers are of interest. Retention in the joint due to high molecular weight, low toxicity, and lack of human metabolic clearance are expected for many possible combinations. Here, it was demonstrates that some unusual mixtures in this class also exert unexpected, but highly desirable gelation and rheological behavior in the joint of a living animal.

A hyaluronic acid (HA) preparation was compared to the present mixtures. Hyaluronic acid serves as a standard comparator. The PEG group showed higher counts when compared to the hyaluronic acid control indicating higher spontaneous mobility in the PEG group. Furthermore, the mixed formulation showed better results. Without being bound by any theory, there are several possible explanations: 1) a nutritional effect for HA; however, HA survival in the joint was short as predicted; 2) the 9% PEG concentration may be so high that it is thick (overly viscous) and simply performed better when diluted to 4.5%; 3) the mixed HA and chondroitin showed a strong gel effect; furthermore, this gel does flow readily under pressure and is highly lubricating. PEG+HA does not gel; however, the dilution of thick PEG may play a role. Again, this result also suggests that the gel effect may in itself be beneficial. The gel may mimic the rheological behavior of the natural HA+lubricin gel in the joint.

Hyaluronic acid (HA) was also compared to a complex mixture of high and low molecular weight PEG suspended in HEC and phosphatidylcholine. This complex PEG composition was chosen based on its low brake angle lubricity score. The mixture showed a brake angle of 7°, the lowest of any composition measured herein. Osteoarthritis was induced as in prior demonstrations. The PEG/HEC/PC group showed higher counts when compared to the hyaluronic acid control indicating higher spontaneous mobility in the PEG/HEC/PC group. Thus, the animal model showed superior behavior relative to HA in this demonstration. Without being bound by any theory, the superior performance is likely based entirely on superior lubricity of the composition.

PEG could likely be advantageously mixed with gels based on gelatin/chitosan, gelatin/chondroitin, CMC/chondroitin, CMC/chitosan, CMC/agarose, HEC/gelatin, HEC/chitosan, HEC/PVP, HEC/agarose, HEC/CMC, and others. Furthermore, multiple synthetic polymers could be usefully mixed with natural polymers. For example, PEG/chitosan, PEG/xanthan gum, PEG/gelatin, PEG/pullulan, and PEG/agarose would form useful gels with high lubrication ability.

M. Semisynthetic Polymers

Several semisynthetic polymer pairs were identified with excellent gelation. These polymers are of low toxicity and have low clearance and good retention in the joint due to high molecular weights and limited or no metabolism. CMC (a poly-acid) and polyglucosamine (a poly-base) form a strong gel, presumably based on lattice formation. Strong gel formation was also found with a variety of non-ionizing compositions, including, but not limited to, HEC/PVP, HEC/PERCOLL®, PVP/PERCOLL®, PEG/PVP, PEG/PBS, PEG/PERCOLL®, PEG/PVA, or PEG 2M/HEC 1.3M/PEG 600K/PEG 100K/PVA 195K/PVP 360K and these also constitute useful embodiments. In addition, mixtures where one component is charged and one is non-ionizing can show good gel formation and are also potentially useful. Examples include CMC/PVP, CMC/agarose, HEC/agarose, HEC/heparin, HEC/CMC, HEC/chondroitin, HEC/HA, HEC/phosphatidyl choline, PEG/agarose, PEG/CMC, and PEG/PEG-tyramine.

Based on the observation that HA plus chondroitin formed a strong gel that was free flowing under minimal pressure when injected, it was hypothesized that the rheological behavior of the HA—lubricin system could be mimicked in synthetic and semi-synthetic compositions. Furthermore, it was speculated that this rheological behavior could account for the apparent improved result with the HA/PEG/chondroitin group vs. HA or PEG groups. Note that the HA chondroitin mix had half the HA concentration of the HA alone mix and half the PEG concentration of the PEG alone mix. Thus, many synthetic and semi-synthetic polymers with high lubricity and low toxicity were mixed with various agents to promote gelation. Hydroxyethyl cellulose (HEC) plus PERCOLL® gave a strong gelation effect. Furthermore, the HEC+PERCOLL® had strong rheological properties, in this case showing increased flow under shear force. Finally, HEC-based mixtures in the rat osteoarthritis model were tested to further demonstrate the effects of in situ gelation. Both the 3% HEC group and the 3% HEC+5% PERCOLL® group showed higher counts when compared to the PBS control. The HEC+PERCOLL® formulation showed better results than HEC alone. Attribution of this enhancement to the superior rheological effect of the gel is based on two observations: a) the fact that PERCOLL® contributes no intrinsic lubrication effect (on a molar basis these nanoparticles in a 5% solution are about $2 \times 10^{-9}$ M in water: silica 2.6 g/mL, PERCOLL® particle 23 nm in diameter) and thus PERCOLL® is not contributing to lubricity and the gel effect can be considered in isolation from lubricity; and b) a nutritional effect of PERCOLL® seems highly unlikely since PERCOLL® is composed only of silica and PVP. Finally all three formulations are buffered as they have been in all of the above animal experiments, by dissolving all components in phosphate buffered saline. It was noted above that the HEC+5% PERCOLL® solution shows a rheological change under shear stress. Therefore, in this simple system, the findings confirm that the gel and/or rheological effects in and of themselves are functionally beneficial in the joint. These rheological gels are rare and HEC/PERCOLL® would be one useful embodiment, more preferably HEC/PVP mixtures, more preferably still PEG/HEC/PVP mixtures. Furthermore, a low amount (0.1% to 1%) of PEG 1-10M, plus 0.1% to 5% HEC (1.3M, for example), with the inclusion of a gelation-inducing agent(s) such as 0.1% to 5% CMC and/or 0.1% to 6% PVP, and/or 0.1% to 1% PVA, and/or 0.1% to 1% agarose, and/or 0.01% to 0.1% heparin sulfate, and/or 0.01% to 0.1% phosphatidylcholine would be advantageous.

N. Modified Polymers

Carboxymethyl cellulose (CMC), a poly-acid, and polyglucosamine, a poly-base, can form a strong gel presumably based on ionic lattice formation. Here, PEG has been chemically coupled to tyramine. In addition, direct coupling can be performed using tresyl chloride chemistry to prepare PEG with linkages to -chitosan, -chondroitin, and -HA as examples (Herold et al., 1989; Harris, 1992; Nayak and Jain, 2011). A strong gel forms in 0.75% CMV 700K and 2.5% PEG 600K-tyramine. The gelation occurs at pH 7.0 to pH 8.0 and is thus compatible with normal joint pH. Tyramine has no chiral rigidity and would not be expected to be antigenic or toxic (Joung et al., 2012). Indeed tyramine is formed spontaneously at several points in human metabolism. The amide linkage to PEG would introduce no new atoms to either parent molecule. Both CMC and PEG have good lubricity. Both agents would have long retention in the joint due to their high molecular weight and absence of metabolism, is a precursor of dopamine, and is found at low levels in human serum and brain tissue (Liberles and Buck, 2006). Furthermore, CMC/PEG-tyramine is a strongly buffering complex that buffers around pH 7.4 to pH 7.8, the normal physiologic pH of the joint. Without being bound by any theory, this buffering effect is probably important to long term joint health. In addition, PEG-tyramine is more soluble than PEG, facilitating production of formulations containing very high molecular weight PEG. Thus, one useful example composition would be PEG-tyramine using PEG 600K. More preferably PEG-tyramine of very high molecular weight (0.1% to 3% of 1-10M molecular weight) mixed with PEG in the 100-900K molecular weight range and/or PEG-tyramine in the 100-900K molecular weight range and/or HEC and/or CMC would yield a useful composition with improved solubility at room temperature. Note also that tyramine is attached at the site of vicinal alcohols of PEG (the only alcohol group available) giving one per molecule. Thus, the high molecular weight PEG would couple relatively few tyramines, and the lower molecular weight PEG would couple more providing more buffering. By mixing PEG/PEG-tyramine of various molecular weights, optimal control of the buffering capacity of the system can be established. One percent CMC formed a strong gel when mixed with 0.25% PEG-tyramine. Thus, a second useful embodiment would be PEG-tyramine in mixed compositions with high molecular weight CMC. Obviously, various molecular weights of PEG, PEG-tyramine, and/or CMC and/or HEC could be employed to optimize lubricity, solubility, buffering capacity, and buffering pH. PEG-tyramine is emphasized here because of its chemical simplicity (one vicinal alcohol per molecule) but the chemical process above could also be used to couple tyramine to various sugar polymers including HEC, HPC, polyglucomannan (pullulan), carboxy methyl cellulose, etc. In addition, the same chemical process could be used to couple tyramine to PVA or other synthetic polymers with exposed alcohol groups.

Based on the observations above, where the rheological behavior of HEC/PERCOLL® was of clear benefit, a further rat osteoarthritis model study was performed with a rheological gel containing PEG-tyramine. A comparison was made between phosphate buffered saline ("PBS"=commercial PBS without Mg or Ca salts from Gibco, 50 µL delivered by direct intraarticular injection) vs. hyaluronic acid ("HA"=ORTHOVISC® pharmaceutical grade at 15 mg/mL, 50 µL delivered by intraarticular injection) vs. a PEG-tyramine containing composition ("PEG-Tyr"=50 µL of 3.5% HEC 1.7M, 3.5% PVP 360K, 1.4% PEG600K-covalently linked to tyramine manufactured as above in PBS, final PH 7.5). Even when made in water, PEG-tyramine was strongly buffering at pH 7.5, with or without the other components of the mixture. All prior studies used an injection volume of 100 µL. However, 100 µL of ORTHOVISC® delivers about 8 times the recommended human dose to the rat joint on an Orthovisk dose/kg weight basis. (The normal human dose is 2 mL of 15 mg/mL; thus, a 70 kg human vs. 400 g rat is 175 times larger. A 100 µL intraarticular dose would equal a 17 mL dose for a human.) Thus, the 50 µL dosing was chosen for this experiment to more closely model the standard amount of HA delivered to the human joint.

The PEG-tyramine composition, containing 3.5% HEC 1.7M, 3.5% PVP 360K, and 1.4% PEG 600K-tyramine, showed significantly higher mobility vs. the PBS control animals while at the same time HA did not. All animal groups were closely matched for weight and baseline activity. Hyaluronic acid was not significantly different from the PBS control, probably due to the short half-life of hyaluronic acid.

Many of the highly charged, high molecular weight natural polymers (such as chitosan) have very limited solubility at physiologic pH. Further, chitosan (polyglucosamine), like hyaluronic acid, is rapidly metabolized. Others natural polymers have poor lubricity (Dextran or Ficoll) or have potential immunogenic reactivity (galactosaminoglycans, etc.). Moderate weight PEG (e.g., 600K) could be coupled directly to CMC or chondroitin or gelatin or agarose, again using CNBr or tresyl chloride chemistry. These could be usefully mixed with PEG-tyramine to form a gel. These molecules could reversibly associate into higher molecular complexes in the joint, thus preserving solubility, gelation effect, buffering conditions optimal for the joint, and potentially desirable rheological behavior mimicking the normal hyaluronic acid—lubricin system. Alternatively, PEG-CMC, PEG-gelatin, or PEG-chondroitin could be constructed and a gel could be achieved when one or more of them are composed in the correct ratio with HEC and the gelling agents demonstrated above, such as PVA, PVP, and PEG-tyramine. This would allow great flexibility in optimizing solubility, molecular weight, buffering, and rheological properties. PEG/HEC would be expected to have superior lubricity and solubility compared with PEG alone per unit of molecular weight. PEG-tyramine could be usefully mixed with HEC to form a gel or PEG coupled to HEC (PEG-HEC) could be made and would preserve the 'hydrophilization' property of HEC and would allow non-ionic gels to be formed with PVP and a gel with one ionic component with PEG-tyramine. Two percent PEG 600K+0.5% chitosan showed no gelation, and 2% PEG 600K+1% HEC showed no gelation, but 2% PEG 600K+0.5% CMC showed strong gelation. Furthermore, 2% PEG 600K+6% PVP 360K and 4.5% PEG 600K+1% PVA 195K also showed strong gelation. Although PEG-tyramine was not produced in large quantities to test the rheological behavior of the present mixtures, when preparing for the latest animal model study it was noted that the HEC/PVP component was only weakly gelled and yet the addition of PEG-tyramine resulted in a very strong gel. A further example would be using tresylchloride to activate HEC (at a low molar ratio) and then reacting HEC-tresylate with low molecular weight polyglucosamine to form a molecule with high solubility, high lubricity, and good buffering potential. When combined with CMC this would yield a strong CMC/HEC-polyglucosamine gel. A similar reaction could be carried out using CNBr chemistry to activate CMC or HEC or HPC to achieve molecules with high solubility, high lubricity, and good buffering potential.

PEG-tyramine could be added to these gels to form a buffering and gelling mixture. PEG has good lubricity. The addition of HEC to PEG gives greater solubility and allows a higher fractional composition of PEG to be used. PEG/PVP and HEC/PVP show some gelation alone; therefore, PEG plus HEC plus PVP will also gel to some extent. PEG/HEC/PVP plus PEG-tyramine is reasonably inferred to form a well hydrated gel with buffering potential. Likewise, PEG/CMC/PVA/PEG-tyramine is likely to be useful. Unlike many naturally-occurring molecules, these synthetic compounds are not metabolized. Furthermore, except for PEG-tyramine, they are all GRAS compounds. PEG 1-10M (0.1% to 5%)+HEC 500K-10 M (0.1% to 5%)+PVP 100K-5M (0.1% to 6%)+PEG-tyramine should be useful. More preferably, PEG 1-4 M (0.1% to 4%), plus HEC 1-3M (0.1% to 4%), plus PVP 1-4M (0.1% to 6%), plus PEG 600K-4M-tyramine (0.1% to 4%) would yield a practical, gel forming, buffering embodiment based on the above demonstrations. More preferably still, PEG 2-4M (0.1% to 4%), plus HEC 2-4M (0.1% to 4%), plus PVA 2-4M (0.1% to 1%), plus PEG 2-4M-tyramine (0.1% to 4%) would yield a practical, gel forming, buffering embodiment based on the above demonstrations, and further would have long term retention in the joint space. More preferred still, a composition of PEG 2-4M-tyramine at 1% to 3%+PEG 600K at 1% to 3%+HEC 2-4M at 2% to 3%+PVP 2-4M at 0.6% to 6% in PBS should be highly useful for intraarticular therapy. It would not be toxic, would be gel forming, would be highly buffered at the physiologic pH of the joint, would be non-metabolizable, would be retained in the joint, and would have desirable rheological characteristics.

IV. KITS

Certain aspects of the present invention may provide kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and a heated mechanical assisting pump syringe for accomplishing direct intra-articular injection of the composition into a joint. In other embodiments, a subject kit may comprise pre-filled ampoules of a composition, optionally formulated as a pharmaceutical, or lyophilized, for use with a delivery device.

Kits may comprise a container with a label. Suitable containers include, for example, bottles, vials, and test tubes. The containers may be formed from a variety of materials, such as glass or plastic. The container may hold a composition of the present invention that is effective for therapeutic or non-therapeutic applications, such as described herein. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Polyethylene Glycol Formulations

PEG as an agent for intraarticular injection is only practically useful under a restricted range of molecular weight and percent compositions. Low molecular weight PEG will flow out of the fenestrated epithelia of the synovia and be diluted in the body. High molecular weight PEG, similar to other high molecular weight molecules in the synovial fluid, would be retained. The desired solubility characteristics restrict the utility of PEG from about 100K to about 10M molecular weight. As the molecular weight of PEG increases, the percentage used in the composition would need to be decreased to avoid an unusably stiff or waxy composition. Thus, for lubricating utility, a restricted range of PEG molecular weights and percent formulations defines a unique range of compositions with a liquid fluid state in the aqueous environment and temperature of the target joint, and which are likely to be retained in the joint. In addition, the hydration properties of PEG by itself may not be sufficient to remain a liquid at the concentrations desired and at the temperature of the joint and thus mixed compositions may be needed (see Example 8 and 9). Further, under highly specialized conditions, low molecular weight compositions may be useful formulation independently or as adjuncts to intraarticular injection (see Example 9).

Thus, the concentration of PEG that is soluble at room temperature, has the greatest lubricity, and has the highest retention in the joint was determined. First, the solubility of 1% aqueous solutions of PEG of various molecular weights (600K, 400K, 200K, 100K, 17K, 5K) was tested. High molecular weight material took longer to dissolve. At higher concentrations (e.g., 12%), PEG 600K prepared in water was difficult to dissolve and was very stiff. The stiffness further increased when prepared in PBS. PEG 600K is near its limit of solubility at 12% and thus yields a waxy, cloudy, gel-like appearance in PBS. Gels have both solid and liquid phase components, which together provide rigidity. In contrast, low molecular weight 35% PEG 17.5K and 100% PEG 400K both remained liquid at room temperature. Thus, solubility was inversely proportional to molecular weight.

Example 2—Colligative Properties of PEG vs. Albumin

Albumin is the major osmolite in serum and is normally 4% to 6% of serum by weight. The molecular weight of albumin (66K) prevents it from crossing capillary epithelia, glomerular epithelia, synovial epithelia, etc. Thus, as fluid under pressure carries salts through capillary epithelia, albumin is retained and concentrated in the capillary lumen (terminal vessel of the circulatory system). Concentrated albumin induces an oncotic pressure that opposes the effect of blood pressure, thus pulling salts back into the lumen. The joint space has similar dynamics. Mechanical weight bearing generates considerable hydrodynamic pressure (analogous to blood pressure) expelling fluid and low molecular weight molecules from the joint. Thus, the osmotic pressure of the joint retains a fluid phase in the joint. Therefore, any PEG-based product of the present invention must match or be below the serum albumin oncotic pressure to prevent joint swelling. As such, the colligative properties of various molecular weight PEGs were compared with 2.5% albumin and the effects were observed in a dialysis model.

The following solutions were made (Table 1) and precisely 1 mL of fluid was added into each of eight dialysis bags using SPECTRA/POR® cellulose acetate 3K cut off (18 mm diameter) membrane. If the oncotic pressure of the PEG solution was lower than the oncotic pressure of 2.5% albumin, then the dialysis bag would shrink. If higher, then it would swell. This was measured by an increase or decrease of the weight of the fluid after four days of dialysis at 4° C. vs. 2.5% albumin in PBS.

After four days, the outside of the bag was gently patted dry and the top dialysis clip removed. The contents of the bag were weighed using a tared weigh boat on an electronic balance with 0.00 g precision. Since neither the PEG nor the albumin can move through the 3 k membrane, water must enter (or leave) the bag until equal oncotic pressure is achieved. Both the 5K and 17.5K PEG with 3% and 4% "albumin equivalents" showed shrinkage (loss of weight) of the dialysis bag when immersed in a 2.5% albumin solution (Table 1). For both molecular weights of PEG, the 1% and 2% "albumin equivalents" solutions showed swelling (increase in weight) of the bag. The long extended superhydrated PEG molecule has humectant properties and yet can also precipitate proteins by excluding water; however, these properties did not interfere with the predicted colligative properties of PEG. PEG demonstrated colligative properties inversely proportional to molecular weight. Thus, high molecular weight PEG allowed for a higher percentage of PEG to be used by weight to achieve the same oncotic pressure. Thus, for a fixed target oncotic pressure, higher molecular weight PEG would allow for a higher percentage of PEG to be used. In addition, higher molecular weight PEGs have intrinsically higher lubricity per unit weight.

TABLE 1

PEG solutions and results for oncotic pressure analysis.

| Albumin Equivalence | Weight (mg) of PEG 5K or 17.5K in 1 mL 1 × PBS | Weight after dialysis vs. 2.5% Albumin (g) |
|---|---|---|
| PEG 5K | | |
| 1% | 7.575 | 0.90 |
| 2% | 15.15 | 0.91 |
| 3% | 22.7 | 1.13 |
| 4% | 30.3 | 1.10 |
| PEG 17.5K | | |
| 1% | 26.51 | 0.94 |
| 2% | 53 | 0.95 |
| 3% | 78.5 | 1.04 |
| 4% | 106 | 1.09 |

Example 3—Freezing Point Depression

Mixtures of PEG and co-solvents were studied to optimize lubricity while still producing a liquid at 34° C. with the expectation is that the solubility (freezing) at 34° C. would follow a similar pattern based on co-solvent effect or colligative properties, regardless of temperature.

Solutions were prepared as shown in Table 2. The percent of the solution in the solid state was determined at 1 h.

TABLE 2

Mixtures of PEG and co-solvents and solid state results.

| Solution | Percent Solid at 1 h at −10° C. (±1° C.) |
|---|---|
| 29% PEG 17.5K | 100% |
| 29% PEG 17.5K + 1% PEG 5K | 100% |
| 29% PEG 17.5K + 1% EtOH | 90% |
| 29% PEG 17.5K + 1% DMSO | 0% (free flowing) |

The solutions containing 32% PEG 17.5K were prepared that also contained 0.18% Fuller's earth in order to prevent possible supersaturated solutions. The solutions were subjected to 10 repeated cycles of controlled freezing. The solutions were mixed thoroughly before each cycle.

TABLE 3

Mixtures of PEG and co-solvents with Fuller's earth and solid state results.

| | Freezing Replicate | | | | | | | | | |
|---|---|---|---|---|---|---|---|---|---|---|
| | 1 | 2 | 3 | 4 | 5 | 6 | 7 | 8 | 9 | 10 |
| Temp Read-out ° C. | −4 | −6 | −4 | −6 | −4 | −5 | 0 | −1 | −3 | −2 |
| Percent Solid by Visual Inspection | | | | | | | | | | |
| 32% PEG 17.5K | 50 | 90 | 10 | 100 | 20 | 50 | 10 | 20 | 50 | 50 |
| 32% PEG 17.5K + 1% PEG 5K | 10 | 75 | 0 | 50 | 10 | 50 | 0 | 5 | 10 | 0 |
| 32% PEG 17.5K + 1% EtOH | 10 | 75 | 0 | 25 | 10 | 10 | 0 | 5 | 0 | 0 |
| 32% PEG 17.5K + 1% DMSO | 10 | 50 | 1 | 10 | 0 | 25 | 0 | 0 | 1 | 0 |

The experimental freezing replicates were significantly different from the 32%+PBS control as determined by Wilcoxon non-parametric matched pairs test: 1% PEG, $P<0.01$; 1% ethanol (EtOH), $P<0.01$; and 1% DMSO, P<0.01. The addition of 1% PEG 5K, 1% ethanol, and 1% DMSO all depressed the freezing temperature (Tables 2 and 3).

Example 4—Lubricity Testing

The lubricating ability of synovial fluid is important and can be studied in ways similar to other lubricants. The lubricity of various PEG solutions was tested using the break angle lubricity test. Twelve stainless steel nuts were purchased. Two were closely matched in weight: Nut 1=7.06 g, and Nut 2=7.08 g. Lubricity was tested by placing these nuts in a 200 μL pool of various PEG solutions on a glass plate and measuring the angle where movement first occurred.

TABLE 4

Lubricity testing.

| Solution in PBS | Break Angle Nut 1 | Nut 2 | Appearance | Observations |
|---|---|---|---|---|
| 1% 17K | 15 | 15 | Clear | Non-viscous |
| 1% 100K | 13 | 14 | Slightly cloudy | Non-viscous |
| 1% 200K | 12 | 12 | Very slightly cloudy | Non-viscous |
| 1% 400K | 11 | 12 | Clear | Very slightly viscous |
| 1% 600K | 17 | 18 | Clear | Slightly viscous (slippery to touch) |
| 9% 200K | 18 | 19 | Cloudy | Visibly viscous (1-3 s to flow) |
| 5% 600K | 17 | 20 | Cloudy | Visibly viscous (30 s to flow) |

Higher molecular weight PEGs provided greater lubricity when between 17K and 400K (Table 4). Molecular weights above 400K had significant viscosity effects that affected the interpretation of the break angle test method.

The experiment was repeated with smaller size weights (Nut 1=4.98 g, Nut 2=4.97 f, Nut 3=4.98 g). It was found that the lubricity of PEG is proportional to molecular weight until viscosity dominates the break angle method at about 400K (Table 5).

TABLE 5

Lubricity testing.

| Solution in PBS | Break Angle Nut 1 | Nut 2 | Nut 3 | Appearance |
|---|---|---|---|---|
| 1% 5K | 20 | 20 | 20 | Clear |
| 1% 17K | 14 | 16 | 16 | Clear |
| 1% 100K | 13 | 16 | 16 | Slightly cloudy |
| 1% 200K | 12 | 12 | 16 | Very slightly cloudy |
| 1% 400K | 15 | 14 | 17 | Clear |
| 1% 600K | 18 | 20 | 25 | Cloudy |

Figure 9:
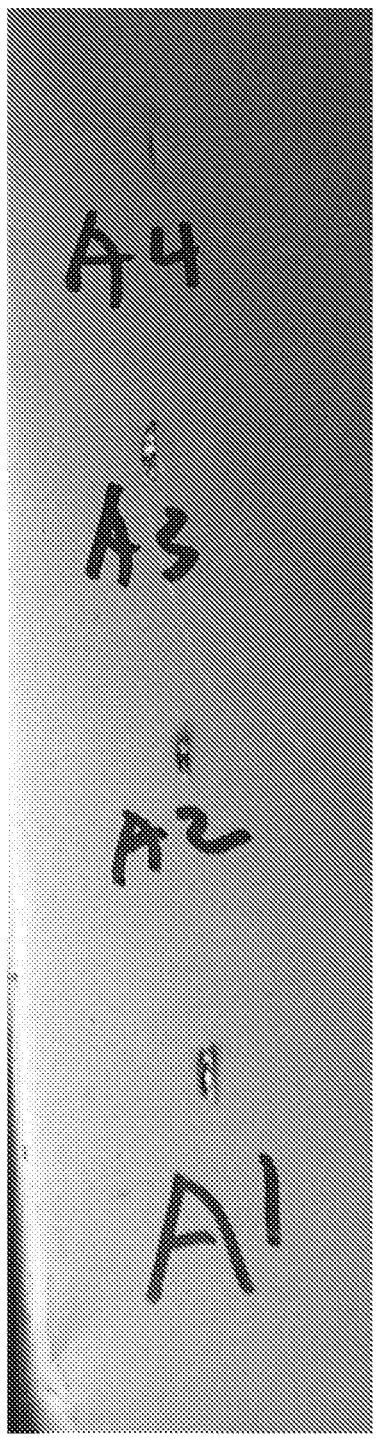
FIG. 9 shows a photograph of the scar test method used to determine lubricity of high molecular weight PEG. A1=1% PEG 200K; A2=9% PEG 200K; A3=5% PEG 600K; A4=4% PEG 600K in 7.5% PEG 200K.

Next, the scar test method was used to determine lubricity of high molecular weight PEG. This method was modified from the EU ISO ref: EN 590 Diesel Fuel Standard Generally Applicable Requirements and Test Methods (Scar test=EN ISO 12156-1). A 'Dremel' tool was used to apply weight and rotational force to a fixed aluminum test platform with 250 μL of each test lubricant applied in a 2 cm×2 cm patch directly under the tool. A medium setting and a brass brush were applied to the aluminum target surface for 5 sec. The compositions tested were as follows: A1=1% PEG 200K; A2=9% PEG 200K; A3=5% PEG 600K; A4=4% PEG 600K in 7.5% PEG 200K. A4 has the smallest scar and A1 had the largest scar with the progression of sizes as follows: A1>A2>A3>A4 (FIG. 9). In the scar test the smaller the scar the better the lubrication.

Lubricity was found to be proportional to molecular weight and concentration. The inclusion of 7.5% PEG 200K in the 4% PEG 600K solution visibly lowered the viscosity and also demonstrated the best lubricity by the scar test.

In addition, the inclusion of a small amount of PEG 100K lowered the viscosity of 6% PEG 600K. Without this addition, 6% PEG 600K is very stiff. When 6% PEG 600K+1% PEG 100K was compared to 6% PEG 600K alone, the 6+1 mixture showed superior flow (lower viscosity) at room temperature. Furthermore, a mixture containing 6% PEG 600K+1% PEG 100K showed improved lubricity as measured by the scar test when compared to 7% PEG 600K. Thus, compositions containing mixed PEG/PEG can provide enhanced lubricity and allow the use of higher molecular weight PEGs.

Example 5—Survival Time in the Knee Joint

In order to characterize the half-life of high molecular weight PEG in the rat knee in vivo, a radioactive iodine ($I^{125}$)-labeled PEG 600K was prepared using a two-step process. First, cyanogen bromide was used to introduce reactive groups (cyanoimide) into PEG under alkaline conditions. Subsequently, PEG-cyanoimide, stabilized at pH 8.5, was reacted with tyramine. Finally, radioactive iodine was used to displace the tyramine group under reducing conditions. After dialysis in PBS and G25 chromatography, the label was filter sterilized using a 0.2 μm nylon membrane and had 300 cpm/μL of the final volume. Twenty microliters of the label was injected into the left knee of a 250 g female Wistar rat. A decay curve was developed over a period of 12 days using a Geiger-counter. The rat was held still each day and radioactive activity, measured as counts per minute, was measured at the surface of the knee.

Counts decreased from 3000 on the first day to 1600 at day 12 (FIG. 1). The log scale plot fits a liner decay model showing approximately a 5% decrease per day. Therefore, the half-life of $I^{125}$ PEG in vivo was approximately 12 days. As there is no known metabolic pathway for the destruction of PEG, gradual diffusion out of the joint with passive elimination through the kidney seemed most likely. Regardless of the mechanism of removal, the half-live is equal to or greater than 12 days. This long half-life exceeds the half-life of hyaluronic acid, which is generally taken to be 24-48 h (Stern, 2004; Genitrix HY50® Datasheet).

Figure 2:
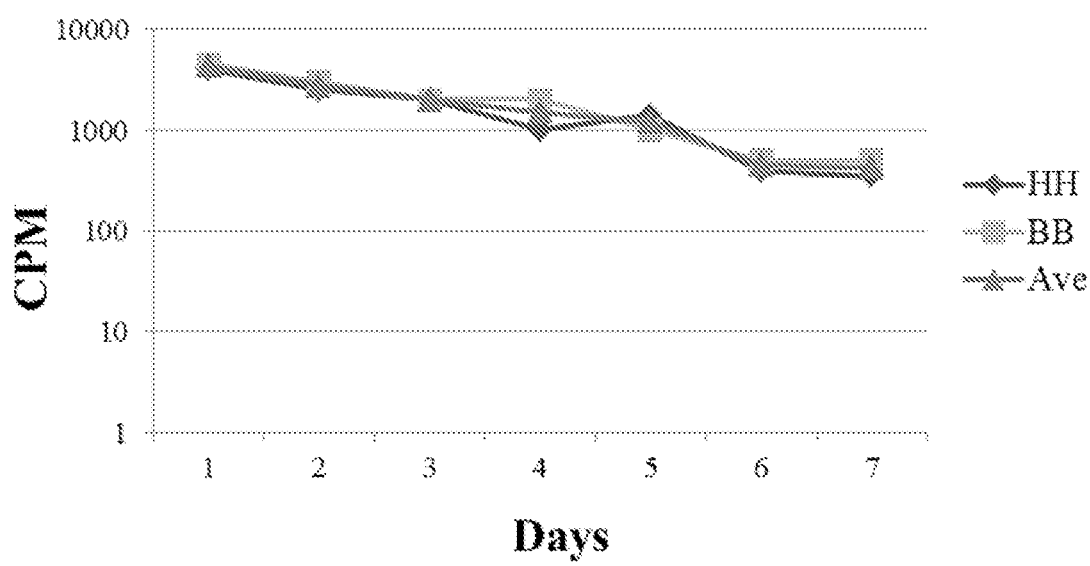
FIG. 2 shows the half-life of hyaluronic acid in the race knee in vivo.

For comparison, hyaluronic acid was also $I^{125}$-labeled and tested in the same way. After dialysis, G25 chromatography, and filter sterilization about 60K counts were injected into the knee joint. Hyaluronic acid was lost from the joint at a rate of ~30% per day. The $T_{1/2}$ therefore approximates 2 days (FIG. 2). The $T_{1/2}$ for hyaluronic acid (ORTHOVISC®, 15 mg/mL), as demonstrated here, agrees with prior literature findings of a 24-48 h half-life. This is shorter than the 12 day half-life of PEG 600K.

Example 6—Rat Model of Osteoarthritis

Six percent PEG 600K with 1% PEG 100K provided good lubricity, low toxicity, prolonged half-life in the joint, and acceptable oncotic and physical parameters. Therefore, this composition was tested in vivo using an established rat model of osteoarthritis based on the well-described activity of mono-sodium iodoacetate (MIA) (Rosenthale and Capetola, 1982; Conforti et al., 1991; Clarke et al., 1997;

Guingamp et al., 1997; Uebelhart et al., 1998; Bove et al., 2003; Neugebauer et al., 2007; Al-Saffar et al., 2009; Tang et al., 2010).

Briefly, MIA is known to interfere with glucose metabolism. Specifically, it interferers with mitochondrial function to the extent that the mitochondrial-dependent variant of the apoptotic cascade is activated. This is particularly important for chondrocytes. In the joint, MIA induces metabolic arrest of the chondrocytes and death proceeds with pyknotic nuclei appearing over the course of 3-7 days. There is little inflammation and the loss of HA and other glycoprotein components of the cartilaginous matrix results in continued and progressive mechanical damage. Histologic changes are best demonstrated after 14 or more days. In these experiments, all animals, both controls and treatment groups, received MIA to cause equal damage to the joints. Treatments injections were typically given after 10-14 days.

The monitoring tool diagramed in FIG. 3 was used as a quantitative measure of rat mobility with the following modifications. A dense polypropylene sheet was glued on to an aluminum frame to provide a rigid waterproof top layer. The second layer consisted of 60 grit sandpaper with the points facing down. The third layer consisted of photo quality matte printer paper. The fourth layer consisted of carbon paper with the carbon facing up. The fifth layer is a smooth ceramic tile surface cut into an 8"×8" square to provide a stable platform for foot print monitoring. The monitors were collected each day after overnight unrestricted spontaneous movement (18-24 h). The "dots" on the monitor paper were counted using image analysis software (AlphaView SA, Informer Technologies, Inc.) with the 'colony count' tool, using fixed contrast and threshold settings, to provide consistent colony counting for all days throughout the study period.

The first comparison was phosphate buffered saline (PBS) as the negative control vs. 6% PEG 600K+1% PEG 100K as the test agent. One hundred microliters of PBS or the PEG mixture were given to each group. The goal of the negative control was to see if the test material was better than the baseline negative control. The PEG group showed significantly higher (P=0.006) counts when compared to the control (FIG. 4; Table 6). This indicates higher spontaneous mobility in the PEG group. MIA-induced chondrocyte death is irreversible and MIA was given here starting 15 days prior to PBS or PEG treatment. Thus, joint pain is likely the major determinant of the differences in counts between the groups. PEG in not known to directly affect pain or sensation and therefore superior lubrication is the likely explanation for the reduction in pain. This short-term rat model is only capable of detecting behavioral (pain) responses. Superior long-term lubrication has the potential to modify the course of osteoarthritis by preventing ongoing mechanical damage. Since chronic low grade mechanical damage is known to be sufficient to induce osteoarthritis, decreasing mechanical damage would decrease the progression of osteoarthritis over time.

TABLE 6

Osteoarthritis model of PBS vs. 6% PEG600K + 1% PEG100K in PBS

| Agent Tested | No. of Measurements | Average No. of Measurements | Standard Deviation |
| --- | --- | --- | --- |
| PBS Group | 20 | 47.1 | 23.6 |
| PEG Group | 19 | 81.3 | 46.5 |

Example 7—PEG Mixtures

Clearly a mixture of different molecular weight PEGs offers potential advantages. For example, 6% PEG 600K+1% PEG 100K demonstrated superior lubricity when compared to 7% PEG 600K. Similarly, 4% PEG 600K in 7.5% PEG 200K demonstrated superior lubricity when compared to 6% PEG 600K. High molecular weight PEG in a lower molecular weight PEG base is an example of the co-solvent effect. High molecular weight PEG, a long linear polymer, becomes more soluble in PEG of a lower molecular weight due to weak force PEG-PEG associations which favor an open linear form of the high molecular weight PEG vs. the high molecular weight PEG by itself, excluding water, and remaining in a ball. An example of this is when a PEG-modified protein partitions into a 4.5% PEG 5K/PBS solution vs. a matched molecular weight 4.5% Dextran 5K/PBS solution, allowing the measurement of the degree of PEG coupling (Scott et al., 1988; Herold et al., 1989; Tarrand et al., 1989; Scott et al., 1989; Harris, 1992; Delgado, 1993; Delgado, 1997; Fee and Van Alstine, 2006; Pasut and Veronese, 2009). This enhanced solubility allows a higher fraction of PEG to be incorporated into a formulation without increased viscosity. Similarly, higher molecular weight PEGs become more practical when using this co-solvent approach. A preferred embodiment may include PEG 600K-10M in a mixture of PEG 100K-600K. If the bulk consists of a medium and a low molecular weight, then this should optimize the lubricity of the high molecular weight material while maintaining the necessary fluidity suitable for injection. For example, PEG 1.8M would provide superior lubricity than PEG 600K; however, the solubility of PEG 1.8M would typically limit its practical utility in an aqueous environment. Useful compositions based on the above experimental observations are promising. An example would be 0.5% PEG 1.8M dissolved in 4% PEG 600K+1% PEG 100K. These high molecular weight PEG mixtures, containing a component of >600K) can be dissolved in PEG 400K+PEG 100K in water with the addition of DMSO. Subsequently, the DMSO can be removed by dialysis vs. water and then changed into an iso-oncotic PEG 400K or PBS, sorbitol, glucose, ringers lactate, or another iso-oncotic aqueous base solution. Compositions of PEG 600K-10M at between 0.01% to 6% in an environment comprising substantial amounts of PEG 100K-600K to more than one million molecular weight at between 0.1% and 5% and in a solvent system based on low molecular weight PEG from 260-100K at between 0.1% and 10% will provide a highly lubricating biocompatible and injectable composition with a long biological half-life. A preferable example would be 0.5%-2% PEG 1-2M, 0.5%-2% PEG 600K, and 1%-4% PEG 100K. More preferable still would be 1% PEG 2M wetted with DMSO and slowly added (1 to 3 days), with constant mixing, to an aqueous solution of 2% PEG 600K and 2% PEG 100K. Subsequently, DMSO is removed by dialysis into PBS. The material requires gentle heating prior to injection. All percentages represent weight/volume in PBS, pH 7.4. Also provided is a room temperature formulation comprising 2% HEC (1.3M molecular weight), 1% PEG 100K, 2% PEG 600K, and 2% PEG 2M. This was made by first dissolving HEC in water, on wet ice overnight, then adding PEG 100K for 3 h, PEG 600K for 3 h, and finally 2% PEG 2M overnight at room temp with slow tumbling. Finally, 0.6% NaCl was added, and the mixture was sterilized by three cycles of Tyndallization at 80° C.

Example 8—PEG Mixtures with Other Highly Hydrated Molecules

PEG provides excellent lubricity, good retention in the joint, and a well-known low toxicity. Other highly hydrated molecules may also offer advantages in the joint space. The amount of PEG that can be put into the joint is limited to some extent by its stiffness. However, the inclusion of other highly hydrated molecules will ameliorate this limitation. The inclusion of hydroxyethyl cellulose (HEC) or hydroxypropyl cellulose (HPC), and/or polyvinyl alcohol (PVA), and/or polyvinylpyrrolidone (PVP) would maintain or improve solubility and lubricity and also provide better flow characteristics. When a small amount of PVP (1.3%) was included in mixtures with high molecular weight HEC (1.3 million, 2%), the viscosity of the material was markedly reduced. The inclusion of 1.3% PVP (360K) added to 2% HEC mixtures, plus 9% PEG improved the flow characteristics of these mixtures. Thus, improved injectable composition with high flow, low toxicity, prolonged half-life, and improved lubrication would be feasible since the inclusion of the highly hydrating molecules also allows the solubilization of higher molecular weight PEG. Hydroxyethyl cellulose, methylcellulose, and hydroxypropyl cellulose are used with cosmetic and hydrophobic drug formulations to improve the drugs' dissolution. This process is known as "hydrophilization." These high molecular weight compounds have low toxicity and due to the lack of a metabolic pathway would be retained in the joint space (NIH, Specialized Information Services). Better hydration properties appear to allow increased concentrations of PEG to be incorporated. Further, better hydration of these PEG-based compositions should allow for better oxygenation and nutritional flow to the joint. Various fractional mixtures of high molecular weight PEG 1-10M (0.001% to 1%), in a substantial amount of PEG 600K (0.5% to 12%) and HEC (0.5% to 12%), and containing PVA or PVP (0.1% to 12%) will allow improved solubilization of the high molecular weight PEG and provide superior injectable lubricating biocompatible non-toxic compositions with good flow and a long biological half-life. Nine percent PEG 600K+2% HEC 1.3M+1.3% PVP 360K has been composed as an example. Clearly, there are several classes of well-hydrated, biologically tolerated, molecules that may be considered as adjuncts to PEG. These include synthetic, semisynthetic, and natural polymers. PEG-PVP is a good example of a synthetic mixture having the unique advantage of a gel property. PEG-HEC-PVP as discussed above would be a synthetic and semisynthetic mixture. Molecules such as dextran, polyglucosamine (chitosan), agarose, pullulan, and xanthan gum, mixed with PEG would be examples of synthetic—natural polymer mixtures. These high molecular weight natural polymers can be very stiff but have usable flow/viscosity in the 0.1%-5% range. These molecules would be chosen to promote hydration and solubility of high molecular weight PEG. They would not be metabolized, would be of a high molecular weight making them unlikely to be cleared from the joint, would have low oncotic pressure, and would remain liquid at joint temperatures. A preferred example would be 1% PEG 1-2M, 0.1%-4% HEC 1.3M, 0.1%-4% PVP 360K. More preferable still would be 1% PEG 2M wetted with DMSO and slowly added, with mixing, to an aqueous solution of 1.5% HEC 1.3M and 1% PVP 360K. Subsequently, DMSO is removed by dialysis into PBS. The examples proposed here have PEG levels well below the 10 mg/kg/day safe level for this GRAS compound (Harris, 1992; Herold et al., 1989). HEC is similarly non-toxic and classified as GRAS (Anon, 1986; GRAS food ingredients). Also PVP is a GRAS compound and has been used as a volume expander (NIH hazardous substances database; Cayton and Clayton, 1993).

Example 9—PEG 400

Very low molecular weight PEG offers unique potential. It is posited that the very low molecular weight PEGs (170-400 MW and up to 200K MW) would not be injected directly into the joint but instead be administered systemically, e.g., used in an intravenous infusion, intravenous bolus, subcutaneous or IM deposition, or by an intarperitoneal bolus injection, or be given orally. PEG 400 is a liquid at room temperature and has been used as a solvent in pharmaceutical mixtures. Further, PEG 400 has low toxicity. Monkeys given 7 g/kg/day of PEG 400 for 3-4 weeks developed a reversible hepatitis in 50% of animals (Lockard et al., 1979). This dosing level used in monkeys equates to 490 g/day in a 70 kg man. Clearly, this is a massive dose. In contrast, 700 mg/kg I.V. in rats (49 g/70 kg man) blocked loss of function in a brain trauma model with no toxicity (Koob et al., 2005). PEG 400 is incorporated in many injectable pharmaceuticals and is generally well tolerated. PEG given IP has been documented to promote neural regrowth by reducing inflammation (Shi and Borgens, 1999; WHO publication found on the world wide web at inchem.org/documents/jecfa/jecmono/v14je19.htm). Thus, direct dosing of low molecular weight PEG would allow diffusion into small joints with potential benefits of lubrication and reduced inflammation and is a feasible osteoarthritis treatment. Low molecular weight polyethylene glycols between 238 and ~100K would pass through the epithelia and into small joints. As an example, a 140 mL intraperitoneal bolus of 50% PEG 400 (700 mg/kg) would diffuse only slowly out of the IP compartment and would be well below any documented toxic range for PEGs between about 238 MW to about 8000 MW. PEG 400 will have minimal osmotic impact since it distributes in total body water, and indeed is used as a tracer of body water (van Wijck et al., 2012). Thus, one familiar with the art can reasonably expect that PEG between 238 (pentaethylene glycol) and about 100K molecular weight would have utility in osteoarthritis in the small joints by a lubricating and/or anti-inflammatory mechanism. These compositions could be administered in aqueous biocompatible solutions. For example, iso-osmotic peg in water or saline or PBS by infusion of up to 60% (w/v) PEG 400 in saline, PBS, ringers lactate, glucose or other common half-strength or quarter-strength salt solution to be given intravenously by infusion or slow bolus or as an intarperitoneal bolus. Further, formulations involving low molecular weight PEG (about 400 to about 24K MW) with the inclusion of intermediate weight PEG (about 50K to about 300K) should have advantages. The intermediate molecular weight PEG should be able to diffuse into large joints since large molecules like immunoglobulin get into normal healthy joints to some degree by diffusion through the fenestrated epithelia. This should provide utility as a treatment for small joints and as an adjunct treatment to the simultaneous intraarticular injection of high molecular weight PEG mixtures into the large joint proposed above. The inclusion of a small amount of higher molecular weight PEG in a large IP bolus would tend to slow the osmotic swelling of the bolus site and thus slow diffusion out of the bolus to provide more sustained delivery. Alternatively to the intermediate PEG 50K to 300K outlined above, a variety of other pharmaceutically acceptable materials such as dextran, hydroxyethyl starch, branched or multi-arm PEGs, or very high molecular weight PEG (1-12M), and a variety of well tolerated natural polymers such as, polyglucosamine, polysaccharides, and other carbohydrates, carboxymethyl cellulose, hydroxyethyl cellulose and other semi-synthetic polymers could serve this same function of facilitating prolonged release of low molecular weight PEG.

In summary, low molecular weight compositions that provide lubrication, have anti-inflammatory characteristics, are biocompatible, and can be given IV, by slow bolus infusion, by periodic subcutaneous injection, by IM or intra-peritoneal injection/deposition, or even administered orally, may provide sustained treatment of small joints. For example, 10%-60% PEG 400 (w/v) in half-strength saline administered by IP or IV bolus, with a preferred embodiment being 20%-60% PEG 400, plus 1%-30% PEG 8K in half-strength saline given IV. Another embodiment may be 50% PEG 400, plus 5% PEG 8K, plus 8% PEG 100K molecular weight in half-strength saline given by IV bolus. The most preferred embodiment is a simple oral formulation of one or more PEGs of low molecular weight (e.g., PEG 400) and given at an appropriate dose and dose schedule of ~1 to 300 gram per day, with or without an osmotic stabilizer to ensure slow release, for example, 10-30 grams PEG 400 taken orally as a 5% solution in juice 1-2 h before meals, once or twice per day.

Example 10—PEG in Mineral Oil

Compositions based on alkanes, such as mineral oil and the oxygen-carrying fluorinated hydrocarbons (FLUORINERT®), and a high molecular weight PEG, and emulsifying agents such as, steryl alcohol, phosphatidylcholine, oleic acid, oleyl alcohol, hydroxyl stearate, cetyl alcohol, myristyl lactate, isopropyl myristate, and/or biocompatible natural polymers, such as agarose, alginate, carrageenan, guar gum, locust bean gum, xanthan gum, or synthetic polymers, such as PEG or hydroyethyl cellulose, and/or detergents, such as CHAPS, TWEEN® 80, NP40, or sodium cholate, or silicone oils, would assist in forming dispersed emulsion composition(s) that are water insoluble. These mixtures offer high lubricity and would not diffuse out of the joint due to their hydrophobic nature and thus provide biocompatible hydrophobic lubricants. Compositions of mineral oil+phosphatidylcholine in PEG; or mineral oil+phosphatidylcholine in ethyl acetate; mineral oil+phosphatidylcholine+hydroxyethyl cellulose in PEG 400 are of particular interest since the inclusion of phosphatidylcholine as an emulsifying agent seems to significantly enhance lubricity. More preferably steryl alcohol can be used as the bulk solvent: steryl alcohol+PEG+phosphatidylcholine+polyvinylpyrrolidone+polyvinyl alcohol+polysorbate 80. More preferably still, high molecular weight PEG+steryl alcohol+phosphatidylcholine+polyvinylpyrrolidone+polyvinyl alcohol+polysorbate 80+petroleum jelly in a silicone oil based solvent. Several preferred hydrophobic compositions are as follows: A [3 mL mineral oil; 7 mL PEG 400; 0.25 g PEG 200K; 0.75 g PEG 600K; 0.1 g TERGITOL® NP40] or B [3.5 g lecithin; 6 mL mineral oil; 0.5 mL FLUORINERT® 70; 0.1 g NP40] or C [10 mL PEG 400; 1 g phosphatidylcholine; 0.1 g petroleum jelly] or D [10 mL PEG 400; 1 g phosphatidylcholine; 0.56 g polyvinylpyrrolidone; 0.1 g petroleum jelly] or E [1 mL steryl alcohol; 0.5 g PEG 600K; 0.01 g PEG 2M; 0.5 g phosphatidylcholine; 0.1 g polyvinylpyrrolidone; 0.1 g polyvinyl alcohol; 0.01 g plysorbate 80; 0.9 mL high molecular weight silicone oil] or F [97.8 g silicone oil 400K; 1 g PEG 2M; 1 g PEG 600K; 0.2 g phosphatidylcholine].

The breaking lubricity of material D [10 mL PEG 400; 1 g phosphatidylcholine; 0.56 g polyvinylpyrrolidone; 0.1 g petroleum jelly] was tested in an identical manner to the above studies, and showed a break angle of 7.5 degrees (average of 12 measurements). Furthermore, material D is non-miscible in water. The composition requires heat (in an 80° C. bath with mixing until fully dissolved) and then a quick cool (in an ethanol-dry ice bath) for stable storage at −70° C.

Clearly various ratios of phosphatidylcholine (PC) to Petrolatum with the addition of the emulsifiers, oleic acid, hydroxyl-stearate, natural or synthetic or semisynthetic polymers, and or biological detergents can achieve, a stable emulsion that is biocompatible and highly lubricating. Similar emulsifiers are found in some cosmetic applications. A preferred composition is 10 mL PEG 400+1 g phosphatidylcholine+0.56 g PVP 360K+0.1 g petrolatum. The composition is formed by slow mixing at 80° C. and then snap freezing at −70° C. By quick reheating in an 80° C. water bath, an opalescent yellow viscous fluid is again quickly regenerated. This material must be kept at 35° C. prior to injection. Surprisingly, this material had one of the highest lubricities measured of any composition tested so far. This formulation, when exposed to water, forms a hydrophobic/hydrophilic boundary layer similar to the behavior of normal articular cartilage and has high lubricity. It is noteworthy that natural cartilage is not particularly strong. Cartilage avoids ware and degeneration, at least in part through the exceptional lubricity of the phospholipid-dependent hydrophobic/hydrophilic boundary layer found in the normal joint. The boundary layer has been measured and functions with about 1000-fold less friction compared with that of the best ball bearing systems (Bove et al., 2003; Gale, 2007; Necas et al., 2008). Simple compositions of mineral oil and various mixtures of PEG (Composition A) have good lubricity and form a strong gel that may distribute impact in the joint. Similar compositions but with the addition of phosphatidylcholine showed improved lubricity (Compositions B and C). A preferred composition includes polyvinylpyrrolidone: 10 mL PEG 400+1 g phosphatidylcholine+0.56 g polyvinylpyrrolidone+0.1 g petrolatum, which forms a stable dispersed solution as opposed to an emulsion, can be stored indefinitely (after being snap frozen), and has high lubricity as measured using the break angle test. A further more preferred embodiment replaces petroleum jelly or mineral oil with steryl alcohol and lubricity is enhanced with the addition of PEG (high molecular weight), steric acid, phosphatidylcholine, polyvinylpyrrolidone, and polyvinyl alcohol, and stability is enhanced with steric acid and TWEEN® 80 as emulsifiers. Similar, compositions but using a mixture of silicone oil (molecular weight >2M) with the addition of phosphatidylcholine, HEC, and emulsifiers should have good stability, lubricity, and biocompatibility. These silicone-based compositions also form an exceptionally high lubricity boundary layer with water. Similar compositions based on steryl alcohol and or silicone, with PEG, phosphatidylcholine, and gelation based on PVP/PVA, chondroitin/gelatin, chitosan/CMC, or (CMC, or HA, or PVP or PVA or agarose) or one or more of these polymers and the synthetic PEG-tyramine (see Example 15) can be used to form a gel. These charged compositions have the advantage of forming a strong polar/non-polar boundary layer at the cartilage surface. The inclusion of specialty water soluble silicones, i.e., LK-Aquaseal-40, with transient water miscibility until $CO_2$ exposure, should further enhance the formation of high lubricity silicone-based water/oil boundary layers. Emulsions of phosphatidylcholine in petroleum jelly or pure 100% petroleum jelly may be the simplest and most effective hydrophobic compositions. For example, a 10% solution of phosphatidylcholine may be made in DMSO with heating and then diluted 1:100 in petroleum jelly to yield a stable 0.1% phosphatidylcholine solution in petroleum jelly. These emulsions may require the use of specialized pre-warming and mixing procedures. They would have low toxicity, high lubricity, and persist in the joint due to hydrophobicity. This would be a practical embodiment for those individuals with advanced disease, referred to as 'bone on bone' osteoarthritis, where most or all of the cartilage has been lost. In this setting preservation and nourishment of cartilage is no longer the goal and a pure lubricant would be desirable.

Example 11—PEG-coupled Antimicrobials

Rare cases of arthritis mimicking osteoarthritis have been linked to chronic subclinical *chlamydia* infection. These usually follow a sexually transmitted disease; however, many species of *Chlamydia, Chlamydophila*, "*Chlamydia*-like organisms" and Legionellaceae are completely dependent on amoeba for their survival in the environment and are not currently cultivatable. Thus, a formulation with both lubricating properties and the ability to deliver antimicrobials is envisioned. Antimicrobial delivery can be accomplished by an adsorbent, such as nano-carbon or nano-silica, by the use of an ionic interaction-based complex, or by antimicrobial coupling to a polymer so as to slowly release antimicrobials into the joint (Nayak and Jain, 2011). These antimicrobial releasing adsorbents, complexes, or covalently-linked antimicrobial and polymers can be formulated as part of a mixture containing a lubricating component and an antimicrobial component suitable for intraarticular injection or can be composed of the covalently coupled antimicrobial—polymer as a sole agent. PEG-based materials provide useful examples.

Clarithromycin and Moxifloxacin are antimicrobials with high activity against *Chlamydia* and *Legionella*. The susceptibility of *Chlamydia* to Clarithromycin or Moxifloxacin is in the 5-50 ng/mL range (Cross et al., 1999; Rihl et al., 2006). As shown below, both antimicrobials are nucleophiles and would not be ionized at the alkaline pH of the joint but would be reversibly bound to a weak poly-acid, such as carboxymethyl cellulose. A mixed composition can be formulated to include about 0.1%-1% high molecular weight PEG and 1%-4% HEC with the addition of 0.01%-1% CMC and the inclusion of about 1 μg to about 1 g of an antimicrobial. This material is a strong gel and the vast excess of CMC favors ionic association between the nucleophilic antibiotics and CMC. This material would provide a high molecular weight CMC acting as a Lewis acid in the joint, which would reversibly bind significant amounts (1-100 mg) of Clarithromycin or Moxifloxacin resulting in a slow-release formulation. CMC is also highly hydrophilic, acts as a good dispersing agent for PEG, is non-toxic, and is itself highly lubricating. In a second example, PEG can be activated with CNBr in alkaline conditions followed by nucleophilic attack by the nitrogen of Clarithromycin. The resultant iso-urea bonds will slowly decay, thus regenerating the Clarithromycin, which will be slowly delivered to the joint. These formulations can be used to provide lubrication, retention in the joint, low toxicity, and a slowly-released form of Clarithromycin, Moxifloxacin or other nucleophillic antimicrobials to treat Chlymidiaceae, Legionellaceae, *Mycoplasma* and other mollicutes, other "*Chlamydia*-like organisms" and septic arthritis due to other bacteria. All organisms producing septic arthritis elicit an inflammatory response, lower the pH of the joint, and thus promote apoptosis of cartilage, and once lost, adult cartilage has no regenerative potential. Thus, the anti-inflammatory activity of PEG should have a role in acute septic arthritis as well as in chronic septic arthritis do to rare, unusual or opportunistic organisms.

Example 12—Compositions with Improved Properties Due to Gelation and Altered Rheological Behavior As outlined above, an optimized composition will mimic the gel effect of the native joint hyaluronan/lubricin gel system. The optimal gel distributes the shock load at rest, but provides a low viscosity and high lubricity fluid flow when in motion. These requirement restrict the compositions to a unique range of acceptable molecules with low toxicity, prolonged half-life, low metabolism, low oncotic pressure at the concentrations needed to provide high lubricity, acceptable function in the aqueous environment of the joint, and most critically to those few compositions that provide functional lubricity, and yet additionally provide a rheologically shear-sensitive gel. Rheologic properties describe non-Newtonian fluid flow. Compositions identified herein form a strong gel at rest yet flow rapidly under pressure-induced shear-stress.

Many of the compositions presented herein are highly hydrated polymers that are readily soluble in aqueous solvents, and include semisynthetic polymers, such as methylcellulose, carboxymethyl cellulose, hydroxyethyl cellulose, or synthetic polymers, such as polyethylene glycol, polyvinylpyrrolidone, and similar molecules, and include natural polymers, such as dextran, polyglucosamine, gelatin, xanthan gum, pullulan, and similar molecules. These compounds are generally well tolerated biologically. Certain polymer pairs were identified that yield compositions capable of forming a gel with the desired rheologic behavior.

Many combinations were studied but only restricted subsets that form gels were identified (Table 7). Many of the polymers listed above will form highly viscous solutions at high concentrations. Therefore, gelation was assessed at a low concentration and by comparing the base polymer at a percentage composition giving moderate viscosity with the addition of a second polymer at a lower percent concentration such that it had an equal or lower viscosity when compared to the base polymer. If the composition is obviously stiff when the two fluids are mixed, then it is said to have formed a strong gel, which was arbitrarily taken to mean that neither parent solution could support its weight under gravity when inverted but the mixture could support its own weight.

TABLE 7

Gelation data.

| Base Material Composition | Description | Modified Material Composition | Description |
|---|---|---|---|
| 1% CMC 700K in water | clear, viscous | 1% CMC 700K in water, 0.3% chitosan ~100K | cloudy, strong gel |
| 1% CMC 700K in water | clear, viscous | 1% CMC 700K in water, 0.1% chitosan ~100K | cloudy, strong gel |
| 1% CMC 700K in water | clear, viscous | 1% CMC 700K in water, 0.5% PVP 360K | clear, no effect |
| 1% CMC 700K in water | clear, viscous | 1% CMC 700K in water, 3% PVP 360K | clear, strong gel |
| 1% CMC 700K in water | clear, viscous | 1% CMC 700K in water, 0.5% HEC 250K | clear, no effect |
| 1% CMC 700K in water | clear, viscous | 1% CMC 700K in water, 0.5% alginate ~100K | cloudy, no effect |
| 1% CMC 700K in water | clear, viscous | 1% CMC 700K in water, 0.5% chondroitin 30K | cloudy, no effect |
| 1% CMC 700K in water | clear, viscous | 1% CMC 700K in water, 0.1% phosphatidylcholine | cloudy, no effect |
| 1% CMC 700K in water | clear, viscous | 1% CMC 700K in water, 0.1% gelatin | cloudy, strong gel |
| 1% CMC 700K in water | clear, viscous | 1% CMC 700K in water, 0.1% agarose | cloudy, strong gel |
| 1% CMC 700K in water | clear, viscous | 1% CMC 700K in water, 0.25% 600K PEG-tyramine | cloudy, strong gel |
| 1.5% HA 1.5M in PBS | clear, viscous | 1.5% HA 1.5M in PBS, 0.6% chondroitin ~30K | cloudy, strong gel |
| 1.5% HA 1.5M in PBS | clear, viscous | 1.5% HA 1.5M in PBS, 0.1% heparin sulf. 40K | cloudy, strong gel |
| 2% HEC 1.3M in PBS | clear, viscous | 2% HEC 1.3M in PBS, 0.3% alginate ~100K | cloudy, no effect |
| 2% HEC 1.3M in PBS | clear, viscous | 2% HEC 1.3M in water, 0.1 chondroitin 30K | cloudy, strong gel |
| 2% HEC 1.3M in PBS | clear, viscous | 2% HEC 1.3M in PBS, 0.3% CMC 700K | clear, strong gel |
| 2% HEC 1.3M in PBS | clear, viscous | 2% HEC 1.3M in PBS, 0.1% heparin sulf. 40K | slightly cloudy, weak gel |
| 2% HEC 1.3M in PBS | clear, viscous | 2% HEC 1.3M in PBS, 5% PERCOLL ® (1% w/w) | cloudy, strong gel |
| 2% HEC 1.3M in PBS | clear, viscous | 2% HEC 1.3M in PBS, 1% phosphatidylcholine | cloudy, strong gel |
| 1% HEC 1.3M in water | clear, viscous | 0.66% HEC 1.3M in water, 0.33% PVA 195K | clear, weak gel |
| 1% HEC 1.3M in water | clear, viscous | 1% HEC 1.3M in water, 6% PVP 360K | clear, Strong gel |
| 2% HEC 1.3M in PBS | clear, viscous | 2% HEC 1.3M in PBS, 1% PVP 360K | clear, weak gel |
| 6% PEG 600K in water | clear, viscous | 6% PEG 600K in PBS | slightly cloudy, weak gel |
| 2% PEG 600K in water | clear, viscous | 2% PEG 600K in water, 1% chondroitin 30K | clear, no effect |
| 2% PEG 600K in water | clear, viscous | 2% PEG 600K in water, 1% HEC 1.7M | clear, no effect |
| 2% PEG 600K in water | clear, viscous | 2% PEG 600K in water, 0.5% chitosan ~100K | slightly cloudy, no effect |
| 2% PEG 600K in water | clear, viscous | 2% PEG 600K in water, 0.5% agarose | clear, strong gel |
| 2% PEG 600K in water | clear, viscous | 2% PEG 600K in water, 0.5% CMC 700K | clear, strong gel |
| 2% PEG 600K in water | clear, viscous | 2% PEG 600K in water, 6% PVP 360K | slightly cloudy, strong gel |
| 4.5% PEG 600K in water | clear, viscous | 4.5% PEG 600K in water, 1% PVA 195K | cloudy, strong gel |
| 0.5% PVA 195K in PBS | clear, viscous | 0.5% PVA 195K in PBS, 0.01% NaBorate500 | cloudy, weak gel |
| 5% PVA 195K in water | clear, viscous | 5% PVA 195K in water, 6% PVP 360K | clear, weak gel |
| 6% PVP 360K in PBS | clear, low viscosity | 6% PVP 360K in PBS, 5% PERCOLL ® (1% w/w) | cloudy, strong gel |

In addition, many combinations were tested that did not gel. In general, both ionic and non-ionic gels were identified. For example, CMC is a poly-acid, usually sold as a sodium salt. When CMC was combined with a poly-base, such as polyglucosamine chloride (chitosan), a strong gel with a neutral pH formed. Presumably gelation was due to ionic interactions favoring larger (non-covalent) interactions. Usually a gel is thought of as made up of a fluid component and solid phase. In this case the solid phase is not a crystalline solid but amorphous solid with equilibria favoring intermolecular association.

In addition, several non-ionic gel combinations were identified, such as HEC/PVP, HEC/heparin, HEC/chondroitin, HEC/CMC, HEC/HA, PEG/PBS, PEG/CMC, PVA/PVP, and HEC/PEG-tyramine. Although polyvinylpyrrolidone has an internal quaternary amine, it is non-ionized under normal conditions (Oster, 1952; McDonald and Spitzer, 1953), although it will decompose in strong acid (Grass et al., 2008). Thus, the mechanism of gelation likely involves small displacement of charge since HEC, PVP, and PEG are non-ionizing. PVP has low toxicity and has previously been used as a plasma volume expander (Trimpin et al., 2001).

Furthermore, and in addition to the identified gel systems, a restricted set of these gels demonstrated favorable rheological properties, meaning a significantly increased flow rate under shear force. Rheology is the study of non-Newtonian fluid behavior in soft solids, such as gels. Newtonian fluids can be characterized by a single viscosity (resistance to flow under pressure) for a specific temperature regardless of changes in the pressure gradient. Non-Newtonian fluids show changing viscosity induced by shear under a force; frequently termed shear stress, or strain, of the fluid. Here, rheological measurements were made by comparing the flow rate (mL/min) under gravity from a vertical 10 mL pipette, using a 23.7 cm (10 mL line) head pressure, to the flow rate under shear stress conditions. Shear stress was obtained by measuring the inflow rate when the material was drawn into the same size pipette using a constant vacuum (300 mmHg).

The results shown in Table 8 are given as a ratio: (flow rate gravity condition)/(flow rate under shear stress condition). This provides a simple way to contrast flow of a gel mixture at low shear stress to the same gel mixture under high shear stress.

TABLE 8

Rheological properties.

| Composition | Gravity flow (mL/min) | Shear flow (mL/min) | Ratio |
|---|---|---|---|
| 3% HEC in PBS + 5% water | 0.00666 | 14.28 | 2164 |
| 3% HEC in PBS + 5% PERCOLL ® | 0.00606 | 37.5 | 6188 (2.86) |
| 3% HEC in water + 5% water | 0.0161 | 15 | 931 |
| 3% HEC in water + 5% PERCOLL ® | 0.0127 | 35.3 | 2779 (2.98) |
| 3% HEC in PBS + 5% water (v/v) | 0.027 | 50 | 1852 |
| 3% HEC in PBS + 5% PERCOLL ® (v/v) | 0.0076 | 35.3 | 4644 (2.51) |
| 2% HEC in water + 5% water | 0.057 | 120 | 2084 |
| 2% HEC in water + 1% PVP | 0.0453 | 85.7 | 1892 (0.91) |
| 2% HEC in water + 2% PVP | 0.0422 | 85.7 | 2030 (0.97) |
| 2% HEC in water + 4% PVP | 0.0456 | 100 | 2193 (1.05) |
| 2% HEC in water + 10% PERCOLL ® | 0.00595 | 36.3 | 6101 (2.93) |

HEC = Hydroxyethyl cellulose 1.3 million molecular weight;
PERCOLL ® = 23% w/w colloidal silica coated with PVP in water,
PVP = polyvinylpyrrolidone 360,000 molecular weight.

Interestingly, a small amount of PERCOLLR® (5% v/v) induced a strong gel with HEC that had desirable rheological properties. One-hundred percent commercial PERCOLLR® is 23% colloidal silica coated with PVP in water. Thus, a mixture containing 5% PERCOLLR® contains ~1% colloidal silica/PVP by weight. However, neither the addition of PVP alone nor micrometer size silica slurry alone resulted in any detectable change in rheological properties of the HEC base material. Further, it should be noted that 100% PERCOLLR® demonstrates no detectable lubricity or viscosity above that of water.

To further explore synthetic polymers with high lubricity and low toxicity and to further explore the benefits of in situ gelation, the monosodium iodoacetate (MIA) osteoarthritis animal model described above was again used. All rats received equal exposure to MIA and a post-MIA baseline was measured. One hundred microliter intraarticular injections of PBS vs. 9% polyvinylpyrrolidone (PVP) 380K in PBS vs. 9% PVP in PBS with the addition of 5% (v/v) PERCOLL®. PVP plus PERCOLLR® had been previously determined to give a strong gel effect.

Figure 5:
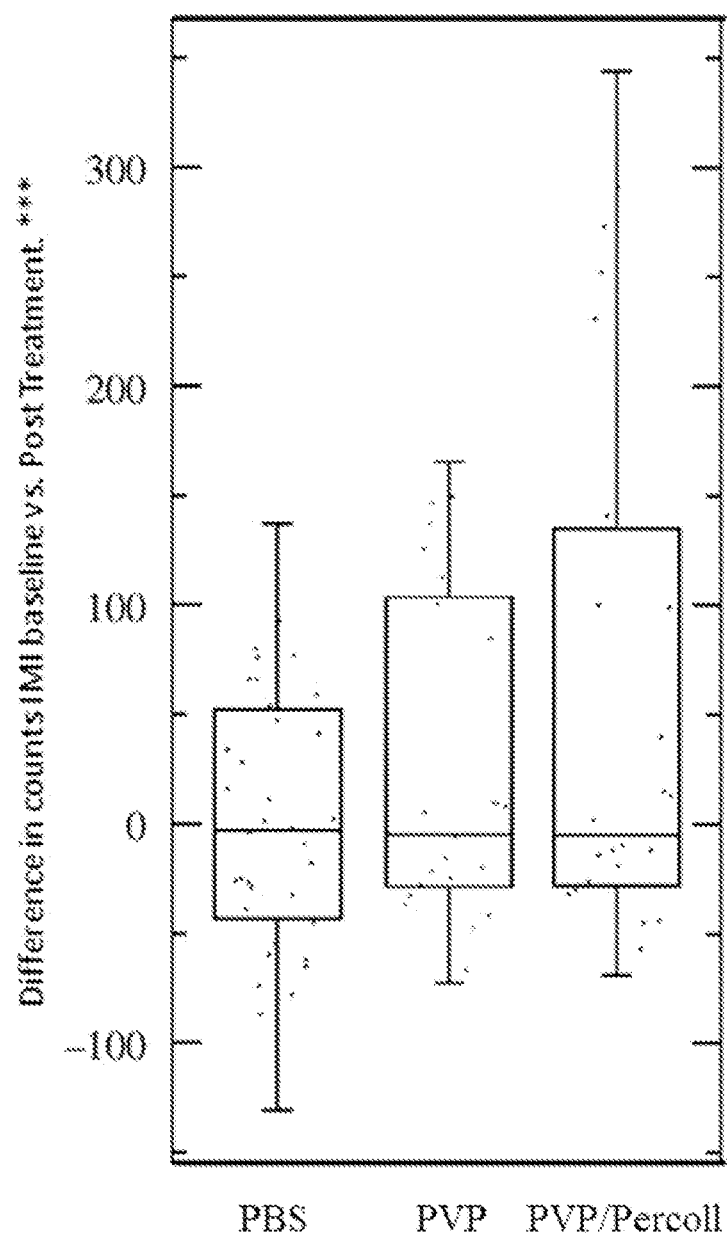
FIG. 5 shows mobility of MIA-treated rats that were treated with PBS alone, 9% PVP (380K molecular weight), or 9% PVP+5% PERCOLL® (v/v). Each box plot shows 50% within the box and 25% in each wing.

After nine days of monitoring, both the PVP and PVP/PERCOLLR® groups showed higher post treatment counts when compared with PBS (P=0.076 for pretreatment IMI baseline vs. PVP; P=0.019 for pretreatment IMI baseline vs. PVP/PERCOLLR®) (FIG. 5; Table 9). PVP has less lubricity and less viscosity at the 9% level than 6% PEG. Furthermore, PERCOLLR® has no intrinsic lubricity and is not detectably different from water even at the 100% level. Therefore, the improved result with the addition of PERCOLLR® demonstrates the advantages of the gel effect alone, in isolation from other factors. A 56% increase in average counts was seen in the PVP/PERCOLLR® group.

TABLE 9

Osteoarthritis model: PBS vs. PVP vs. PVP/PERCOLL ®.

| | PBS | PVP | PVP/PERCOLL ® |
|---|---|---|---|
| N | 36 | 27 | 27 |
| Mean | 0.53 | 31.3 | 56.8 |
| Standard Deviation | 60 | 75 | 121 |

Example 13—Synthetic and Natural Polymer Mixtures with Gel Properties

In Example 8 above it was noted that a large number of potential mixtures of synthetic, semisynthetic, and natural polymers are of interest. Retention in the joint due to high molecular weight, low toxicity, and lack of human metabolic clearance are expected for many possible combinations. Here, it was demonstrates that some unusual mixtures in this class also exert unexpected, but highly desirable gelation and rheological behavior in the joint of a living animal.

A hyaluronic acid (HA) preparation was compared to the present mixtures. Hyaluronic acid serves as a standard comparator. However, the experimental design for this experiment is different than those above. Treatments here were injected 10 days prior to the MIA injection followed by the standard monitoring technique. ORTHOVISC® pharmaceutical grade HA was used at a dose of 15 mg/mL 'neat' injection of 100 μL to deliver 1.5 mg into the rat joint (1.5% by weight per volume; ORTHOVISC® is the highest molecular weight and highest concentration HA currently available on the market, thus this is the maximum HA dose that can be given in 100 μL). This was compared to a 100 L injection containing 9% PEG 600K in PBS, and a 100 μL injection of a mixed composition containing 4.5% PEG 600K, 0.75% ORTHOVISC®, and 0.6% chondroitin.

Figure 6A:
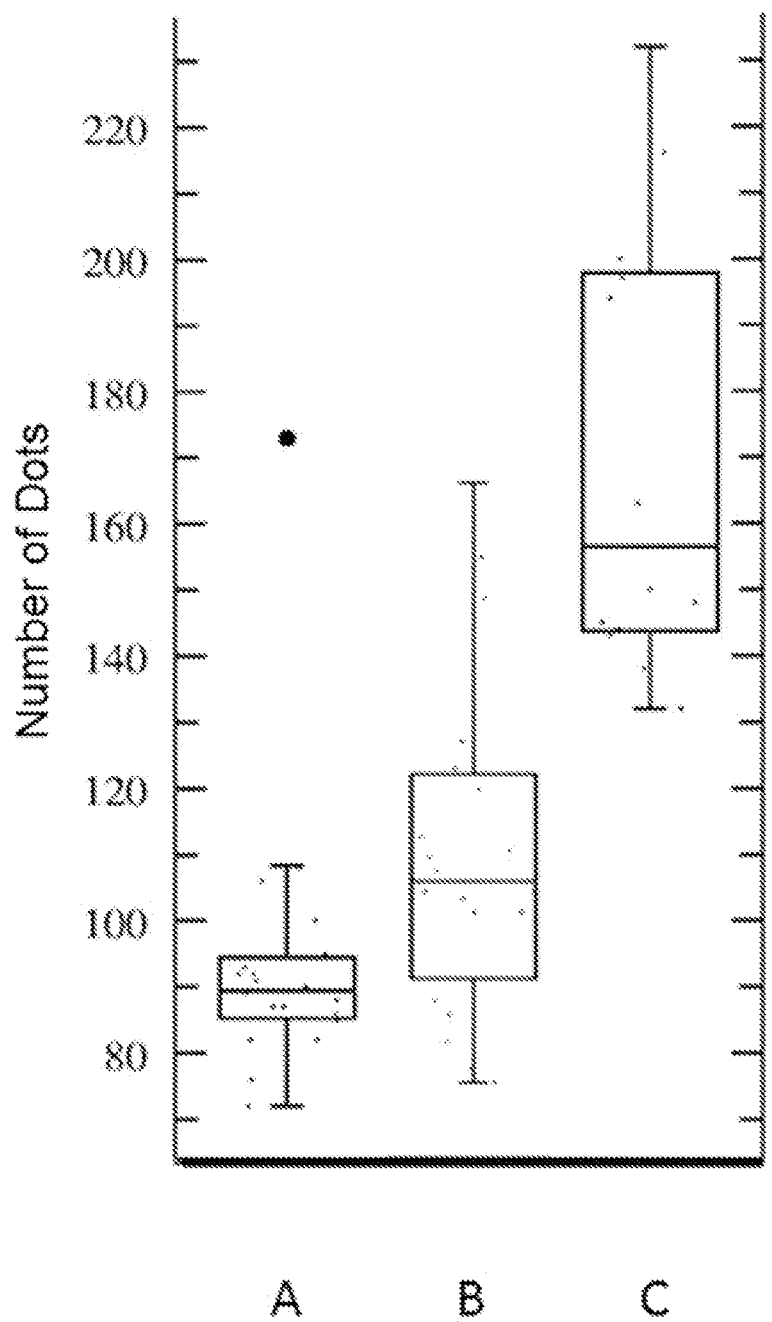
FIG. 6A shows mobility of MIA-treated rats that were treated with ORTHOVISC® (Group A), PEG (Group B), or a combination of PEG, ORTHOVISC®, and Chondroitin (Group C). Each box plot shows 50% within the box and 25% in each wing.

The PEG group showed higher counts when compared to the hyaluronic acid control (P=0.016 for ORTHOVISC® vs. PEG) (FIG. 6; Table 10) indicating higher spontaneous mobility in the PEG group. Furthermore, the mixed formulation showed better results (P=0.0001 for PEG vs. the mixed formulation). There are several possible explanations: 1) a nutritional effect for HA; however, HA survival in the joint was short as predicted; 2) the 9% PEG concentration may be so high that it is thick (overly viscous) and simply performed better when diluted to 4.5%; 3) the mixed HA and chondroitin showed a strong gel effect (see Table 7); furthermore, this gel does flow readily under pressure and is highly lubricating. PEG+HA does not gel; however, the dilution of thick PEG may play a role. Again, this result also suggests that the gel effect may in itself be beneficial. The gel may mimic the rheological behavior of the natural HA+lubricin gel in the joint.

TABLE 10

Osteoarthritis model: ORTHOVISC ® vs. PEG vs. PEG + ORTHOVISC ® + Chondroitin.

|  | ORTHOVISC ® (HA) | PEG | PEG + ORTHOVISC ® + Chondroitin |
|---|---|---|---|
| N | 20 | 20 | 14 |
| Mean | 93.7 | 112 | 169 |
| Standard Deviation | 20.6 | 24 | 32.4 |

Hyaluronic acid (HA) was also compared to a complex mixture of high and low molecular weight PEG suspended in HEC and phosphatidylcholine. This complex PEG composition was chosen based on its low brake angle lubricity score. The mixture showed a brake angle of 7°, the lowest of any composition measured herein. Osteoarthritis was induced as in prior demonstrations. Hyaluronic acid obtained as ORTHOVISCR® pharmaceutical was injected into one group of rats at 100 µl of 15 mg/ml to give 1.5 mg/joint. The second group received 100 µl of 0.9% PEG 4M, 1.8% HEC 1.3M, 0.1% PEG 400, and 0.1% phosphatidylcholine (PEG/HEC/PC group).

Figure 6B:
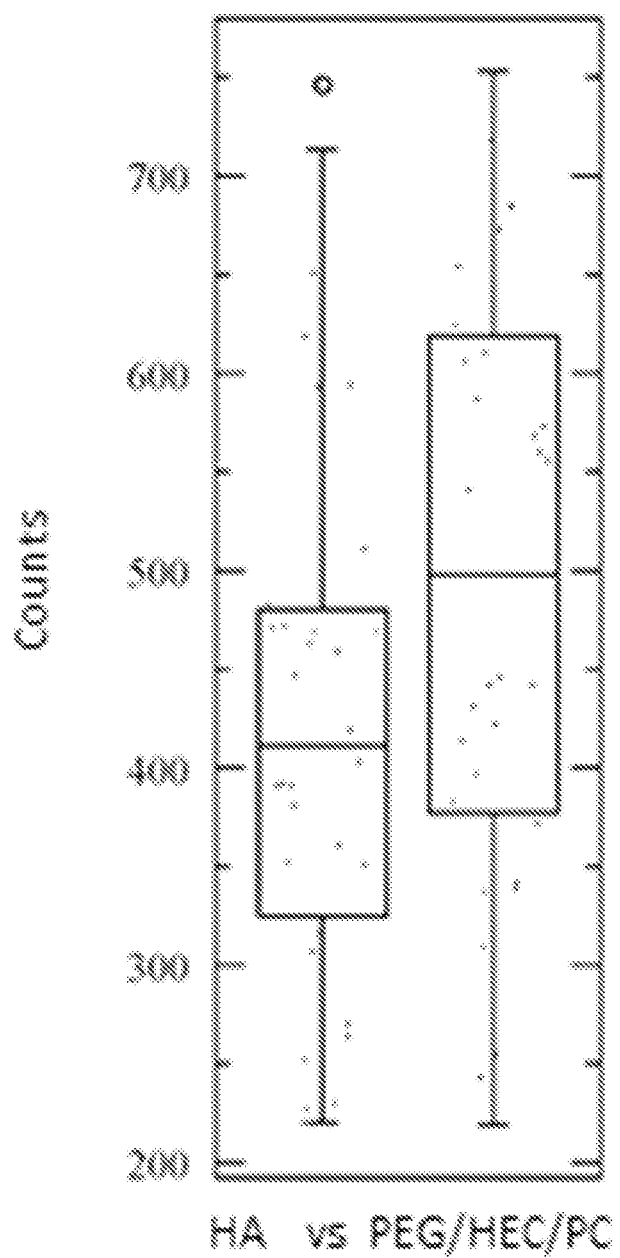
FIG. 6B shows mobility of MIA-treated rats that were treated with HA vs. PEG/HEC/PC. Each box plot shows 50% within the box and 25% in each wing.

The PEG/HEC/PC group showed higher counts when compared to the hyaluronic acid control (P=0.039, FIG. 6B; Table 11) indicating higher spontaneous mobility in the PEG/HEC/PC group. Thus, the animal model showed superior behavior relative to HA in this demonstration. Without being bound by any theory, the superior performance is likely based entirely on superior lubricity of the composition.

TABLE 11

Osteoarthritis model: ORTHOVISC ® vs. PEG 4M in PEG/HEC/PC.

| Agent Tested | No. of Measurements | Average No. of Monitor Counts | Standard Deviation |
|---|---|---|---|
| Orthovisc ® | 32 | 424 | 132 |
| PEG/HEC/PC | 35 | 496 | 148 |

Clearly mixed synthetic and natural polymer formulations are of interest. In addition to the example of composition C in the above rat model, PEG could likely be advantageously mixed with gels based on gelatin/chitosan, gelatin/chondroitin, CMC/chondroitin, CMC/chitosan, CMC/agarose, HEC/gelatin, HEC/chitosan, HEC/PVP, HEC/agarose, HEC/CMC, and others from Table 7. Furthermore, multiple synthetic polymers could be usefully mixed with natural polymers. For example, PEG/chitosan, PEG/xanthan gum, PEG/gelatin, PEG/pullulan, and PEG/agarose would form useful gels with high lubrication ability.

Example 14—Semisynthetic Polymers with Gel Formation

In addition to the examples in Example 13, several semisynthetic polymer pairs were identified with excellent gelation. These polymers are of low toxicity and have low clearance and good retention in the joint due to high molecular weights and limited or no metabolism. As shown in Example 12, CMC (a poly-acid) and polyglucosamine (a poly-base) form a strong gel, presumably based on lattice formation. Strong gel formation was also found with a variety of non-ionizing compositions, including, but not limited to, HEC/PVP, HEC/PERCOLL®, PVP/PERCOLL®, PEG/PVP, PEG/PBS, PEG/PERCOLL®, PEG/PVA, or PEG 2M/HEC 1.3M/PEG 600K/PEG 100K/PVA 195K/PVP 360K and these also constitute useful embodiments. In addition, mixtures where one component is charged and one is non-ionizing can show good gel formation and are also potentially useful. Examples include CMC/PVP, CMC/agarose, HEC/agarose, HEC/heparin, HEC/CMC, HEC/chondroitin, HEC/HA, HEC/phosphatidyl choline, PEG/agarose, PEG/CMC, and PEG/PEG-tyramine (see Example 15).

Based on the observation that HA plus chondroitin formed a strong gel that was free flowing under minimal pressure when injected, it was hypothesized that the rheological behavior of the HA—lubricin system could be mimicked in synthetic and semi-synthetic compositions. Furthermore, it was speculated that this rheological behavior could account for the apparent improved result with the HA/PEG/chondroitin group vs. HA or PEG groups. Note that the HA chondroitin mix had half the HA concentration of the HA alone mix and half the PEG concentration of the PEG alone mix. Thus, many synthetic and semi-synthetic polymers with high lubricity and low toxicity were mixed with various agents to promote gelation. Hydroxyethyl cellulose (HEC) plus PERCOLL® gave a strong gelation effect. Furthermore, the HEC+PERCOLL® had strong rheological properties, in this case showing increased flow under shear force. Finally, HEC-based mixtures in the rat osteoarthritis model were tested to further demonstrate the effects of in situ gelation. This was done by comparing PBS vs. 3% hydroxyethyl cellulose (molecular weight 1.3M) vs. 3% hydroxyethyl cellulose plus 5% (v/v) PERCOLL® (1.15% colloidal silica/PVP final) all given once as 100 µL intraarticular injections.

Figure 7:
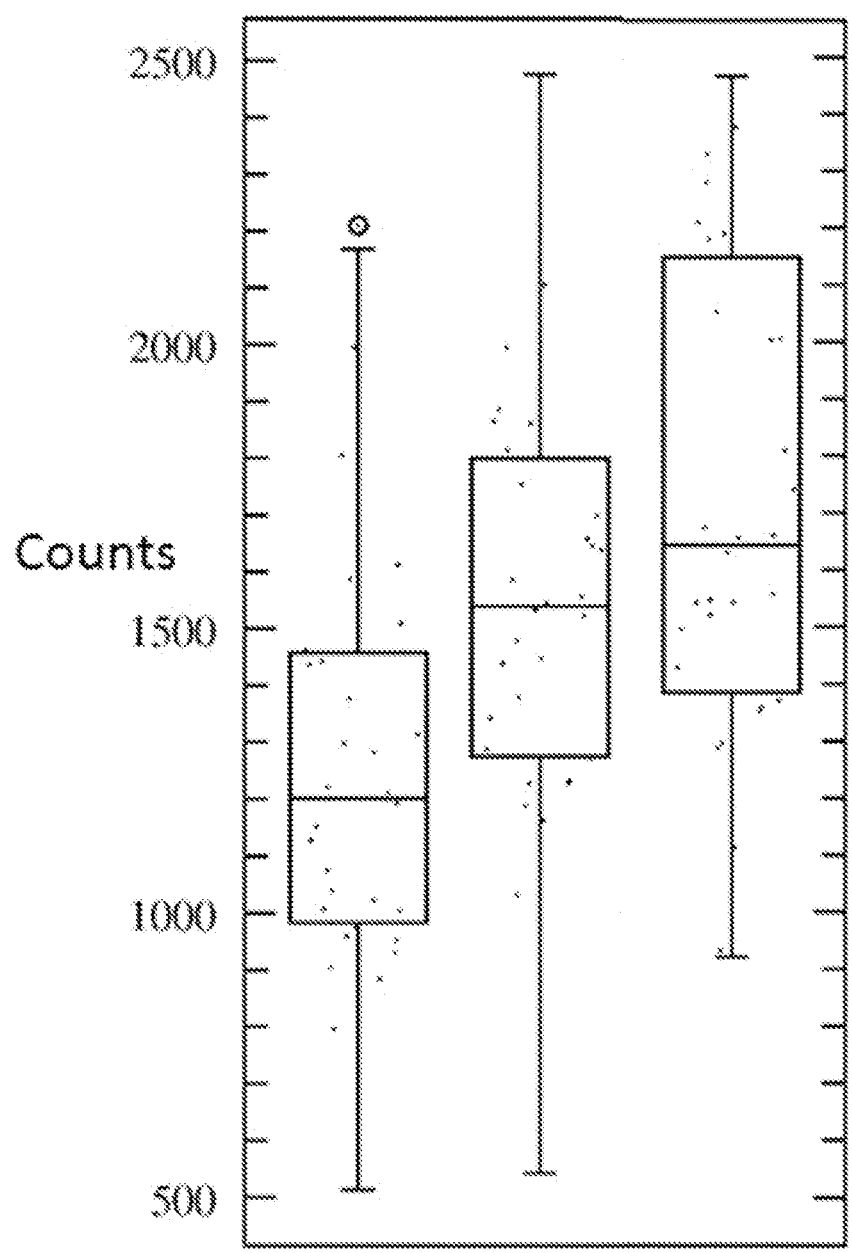
FIG. 7 shows mobility of MIA-treated rats that were treated with PBS, 3% HEC, or 3% HEC+5% PERCOLL®. Each box plot shows 50% within the box and 25% in each wing. Counts are the raw number of counts.

Both the 3% HEC group and the 3% HEC+5% PERCOLL® group showed higher counts when compared to the PBS control (P=0.0014 for PBS vs. 3% HEC; P=0.0001 for PBS vs. 3% HEC+5% PERCOLL®) (FIG. 7; Table 12). The HEC+PERCOLL® formulation showed better results than HEC alone. Attribution of this enhancement to the superior rheological effect of the gel is based on two observations: A) the fact that PERCOLL® contributes no intrinsic lubrication effect (on a molar basis these nanoparticles in a 5% solution are about $2\times10^{-9}$ M in water: silica 2.6 g/mL, PERCOLL® particle 23 nm in diameter) and thus PERCOLL® is not contributing to lubricity and the gel effect can be considered in isolation from lubricity; and B) a nutritional effect of PERCOLL® seems highly unlikely since PERCOLL® is composed only of silica and PVP. Finally all three formulations are buffered as they have been in all of the above animal experiments, by dissolving all components in phosphate buffered saline. It was noted above that the HEC+5% PERCOLL® solution shows a rheological change under shear stress. Therefore, in this simple system, the findings confirm that the gel and/or rheological effects in and of themselves are functionally beneficial in the joint. These rheological gels are rare and HEC/PERCOLL® would be one useful embodiment, more preferably HEC/PVP mixtures, more preferably still PEG/HEC/PVP mixtures. Furthermore, a low amount (0.1% to 1%) of PEG 1-10M, plus 0.1% to 5% HEC (1.3M, for example), with the inclusion of a gelation-inducing agent(s) such as 0.1% to 5% CMC and/or 0.1% to 6% PVP, and/or 0.1% to 1% PVA, and/or 0.1% to 1% agarose, and/or 0.01% to 0.1% heparin sulfate, and/or 0.01% to 0.1% phosphatidylcholine would be advantageous.

TABLE 12

| Osteoarthritis mode: PBS vs. 3% HEC vs. 3% HEC + 5% PERCOLL ® | | | |
|---|---|---|---|
| | PBS | HEC | HEC + PERCOLL ® |
| N | 32 | 32 | 32 |
| Mean | 1244 | 1553 | 1717 |
| Standard Deviation | 357 | 382 | 433 |

Example 15—Specifically Modified Polymers with Improved Properties in Joint Compositions As shown in Example 12, carboxymethyl cellulose (CMC), a poly-acid, and polyglucosamine, a poly-base, can form a strong gel presumably based on ionic lattice formation. Here, PEG has been chemically coupled to tyramine using CNBr chemistry (see Example 11).

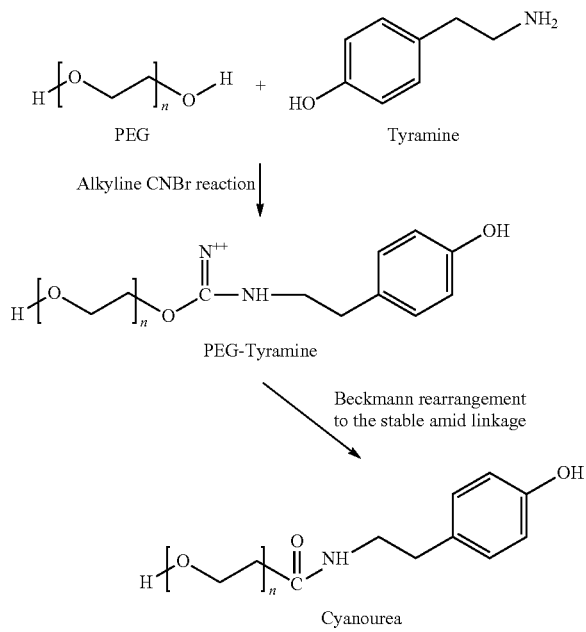

However, direct coupling can be performed using tresyl chloride chemistry to prepare PEG with linkages to -chitosan, -chondroitin, and -HA as examples (Herold et al., 1989; Harris, 1992; Nayak and Jain, 2011). A strong gel forms in 0.75% CMV 700K and 2.5% PEG 600K-tyramine. The gelation occurs at pH 7.0 to pH 8.0 and is thus compatible with normal joint pH. Tyramine has no chiral rigidity and would not be expected to be antigenic or toxic (Joung et al., 2012). Indeed tyramine is formed spontaneously at several points in human metabolism. The amide linkage to PEG would introduce no new atoms to either parent molecule. Both CMC and PEG have good lubricity. Both agents would have long retention in the joint due to their high molecular weight and absence of metabolism, is a precursor of dopamine, and is found at low levels in human serum and brain tissue (Liberles and Buck, 2006). Furthermore, CMC/PEG-tyramine (in the above composition in Table 7) is a strongly buffering complex that buffers around pH 7.4 to pH 7.8, the normal physiologic pH of the joint. This buffering effect is probably important to long term joint health. In addition, PEG-tyramine is more soluble than PEG, facilitating production of formulations containing very high molecular weight PEG. Thus, one useful example composition would be PEG-tyramine using PEG 600K. More preferably PEG-tyramine of very high molecular weight (0.1% to 3% of 1-10M molecular weight) mixed with PEG in the 100-900K molecular weight range and/or PEG-tyramine in the 100-900K molecular weight range and/or HEC and/or CMC would yield a useful composition with improved solubility at room temperature. Note also that tyramine is attached at the site of vicinal alcohols of PEG (the only alcohol group available) giving one per molecule. Thus, the high molecular weight PEG would couple relatively few tyramines, and the lower molecular weight PEG would couple more providing more buffering. By mixing PEG/PEG-tyramine of various molecular weights, optimal control of the buffering capacity of the system can be established. One percent CMC formed a strong gel when mixed with 0.25% PEG-tyramine. Thus, a second useful embodiment would be PEG-tyramine in mixed compositions with high molecular weight CMC. Obviously, various molecular weights of PEG, PEG-tyramine, and/or CMC and/or HEC could be employed to optimize lubricity, solubility, buffering capacity, and buffering pH. PEG-tyramine is emphasized here because of its chemical simplicity (one vicinal alcohol per molecule) but the chemical process above could also be used to couple tyramine to various sugar polymers including HEC, HPC, polyglucomannan (pullulan), carboxy methyl cellulose, etc. In addition, the same chemical process could be used to couple tyramine to PVA or other synthetic polymers with exposed alcohol groups.

Based on the observations above, where the rheological behavior of HEC/PERCOLL® was of clear benefit, a further rat osteoarthritis model study was performed with a rheological gel containing PEG-tyramine. A comparison was made between phosphate buffered saline ("PBS"=commercial PBS without Mg or Ca salts from Gibco, 50 µL delivered by direct intraarticular injection) vs. hyaluronic acid ("HA"=ORTHOVISC® pharmaceutical grade at 15 mg/mL, 50 µL delivered by intraarticular injection) vs. a PEG-tyramine containing composition ("PEG-Tyr"=50 µL of 3.5% HEC 1.7M, 3.5% PVP 360K, 1.4% PEG600K-covalently linked to tyramine manufactured as above in PBS, final PH 7.5). Even when made in water, PEG-tyramine was strongly buffering at pH 7.5, with or without the other components of the mixture. All prior studies used an injection volume of 100 µL. However, 100 µL of ORTHOVISC® delivers about 8 times the recommended human dose to the rat joint on an Orthovisk dose/kg weight basis. (The normal human dose is 2 mL of 15 mg/mL; thus, a 70 kg human vs. 400 g rat is 175 times larger. A 100 µL intraarticular dose would equal a 17 mL dose for a human.) Thus, the 50 µL dosing was chosen for this experiment to more closely model the standard amount of HA delivered to the human joint.

Figure 8:
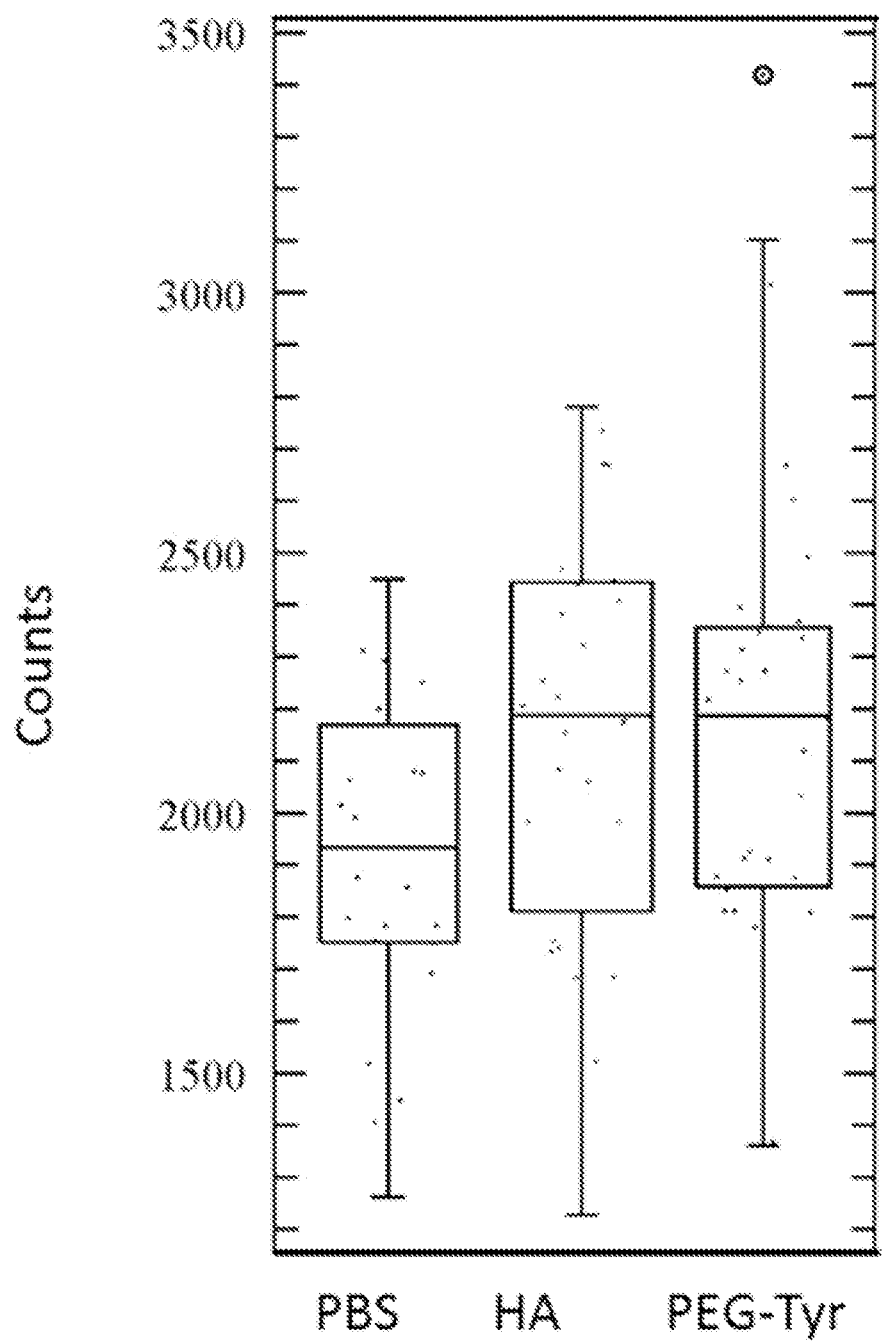
FIG. 8 shows mobility of MIA-treated rats that were treated with PBS, HA, or PEG-tyramine. Each box plot shows 50% within the box and 25% in each wing. Counts are the raw number of counts.

The PEG-tyramine composition, containing 3.5% HEC 1.7M, 3.5% PVP 360K, and 1.4% PEG 600K-tyramine, showed significantly higher mobility vs. the PBS control animals while at the same time HA did not (for PBS vs. HA, P=0.21 [NS]; for PBS vs. PEG-tyramine, P=0.024) (FIG. 8; Table 13). All animal groups were closely matched for weight and baseline activity. Hyaluronic acid was not significantly different from the PBS control, probably due to the short half-life of hyaluronic acid. One unexplained high value was excluded from the PEG-tyramine group as a suspected outlier (>1.5×IQR, John Tukey method).

TABLE 13

Osteoarthritis model: PBS vs. HA vs. PEG-tyramine.

|  | PBS | HA | PEG-tyramine |
| --- | --- | --- | --- |
| N | 24 | 32 | 32 |
| Mean | 1917 | 2066 | 2154 |
| Standard Deviation | 310 | 510 | 422 |

Many of the highly charged, high molecular weight natural polymers (such as chitosan) have very limited solubility at physiologic pH. Further, chitosan (polyglucosamine), like hyaluronic acid, is rapidly metabolized (Lim et al., 2008). Others natural polymers have poor lubricity (Dextran or Ficoll) or have potential immunogenic reactivity (galactosaminoglycans, etc). Moderate weight PEG (e.g., 600K) could be coupled directly to CMC or chondroitin or gelatin or agarose, again using CNBr or tresyl chloride chemistry as above. These could be usefully mixed with PEG-tyramine to form a gel. These molecules could reversibly associate into higher molecular complexes in the joint, thus preserving solubility, gelation effect, buffering conditions optimal for the joint, and potentially desirable rheological behavior mimicking the normal hyaluronic acid—lubricin system. Alternatively, PEG-CMC, PEG-gelatin, or PEG-chondroitin could be constructed and a gel could be achieved when one or more of them are composed in the correct ratio with HEC and the gelling agents demonstrated above, such as PVA, PVP, and PEG-tyramine. This would allow great flexibility in optimizing solubility, molecular weight, buffering, and rheological properties. PEG/HEC would be expected to have superior lubricity and solubility compared with PEG alone per unit of molecular weight. PEG-tyramine could be usefully mixed with HEC to form a gel or PEG coupled to HEC (PEG-HEC) could be made and would preserve the 'hydrophilization' property of HEC and would allow non-ionic gels to be formed with PVP and a gel with one ionic component with PEG-tyramine. Two percent PEG 600K+0.5% chitosan showed no gelation, and 2% PEG 600K+1% HEC showed no gelation, but 2% PEG 600K+0.5% CMC showed strong gelation. Furthermore, 2% PEG 600K+6% PVP 360K and 4.5% PEG 600K+1% PVA 195K also showed strong gelation. Although PEG-tyramine was not produced in large quantities to test the rheological behavior of the present mixtures, when preparing for the latest animal model study it was noted that the HEC/PVP component was only weakly gelled and yet the addition of PEG-tyramine resulted in a very strong gel (almost too strong to inject). A further example would be using tresyl-chloride to activate HEC (at a low molar ratio) and then reacting HEC-tresylate with low molecular weight polyglucosamine to form a molecule with high solubility, high lubricity, and good buffering potential. When combined with CMC this would yield a strong CMC/HEC-polyglucosamine gel. A similar reaction could be carried out using CNBr chemistry to activate CMC or HEC or HPC to achieve molecules with high solubility, high lubricity, and good buffering potential.

PEG-tyramine could be added to these gels to form a buffering and gelling mixture. PEG has good lubricity. The addition of HEC to PEG gives greater solubility and allows a higher fractional composition of PEG to be used. PEG/PVP and HEC/PVP show some gelation alone; therefore, PEG plus HEC plus PVP will also gel to some extent. PEG/HEC/PVP plus PEG-tyramine is reasonably inferred to form a well hydrated gel with buffering potential. Likewise, PEG/CMC/PVA/PEG-tyramine is likely to be useful. Unlike many naturally-occurring molecules, these synthetic compounds are not metabolized. Furthermore, except for PEG-tyramine, they are all GRAS compounds. PEG 1-10M (0.1% to 5%)+HEC 500K-10 M (0.1% to 5%)+PVP 100K-5M (0.1% to 6%)+PEG-tyramine should be useful. More preferably, PEG 1-4 M (0.1% to 4%), plus HEC 1-3M (0.1% to 4%), plus PVP 1-4M (0.1% to 6%), plus PEG 600K-4M-tyramine (0.1% to 4%) would yield a practical, gel forming, buffering embodiment based on the above demonstrations. More preferably still, PEG 2-4M (0.1% to 4%), plus HEC 2-4M (0.1% to 4%), plus PVA 2-4M (0.1% to 1%), plus PEG 2-4M-tyramine (0.1% to 4%) would yield a practical, gel forming, buffering embodiment based on the above demonstrations, and further would have long term retention in the joint space. More preferred still, a composition of PEG 2-4M-tyramine at 1% to 3%+PEG 600K at 1% to 3%+HEC 2-4M at 2% to 3%+PVP 2-4M at 0.6% to 6% in PBS should be highly useful for intraarticular therapy. It would not be toxic, would be gel forming, would be highly buffered at the physiologic pH of the joint, would be non-metabolizable, would be retained in the joint, and would have desirable rheological characteristics.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. Nos. 2,834,748, 3,480,583, 3,600,418, 5,177,167, and 5,971,809
U.S. Patent Publication Nos. 20120251615, 20120277307, 20130005681, and 20130084268
Ackland et al., Low-molecular-weight polyethylene glycol improves survival in experimental sepsis. *Crit. Care Med.,* 38:629-636, 2010.
Al-Saffar et al., Collagenase and Sodium Iodoacetate Induced Experimental Osteoarthritis model in Sprague Dawley Rats. *Asian J. Scientific Research,* 2:167-179, 2009.
American Academy of Orthopedic Surgeons, Total Hip Replacement. On the world wide web at Orthoinfo.AAOS.org/topic.cfm?topic=a00377.

Andersen, Special Report: Reproductive and Developmental Toxicity of Ethylene Glycol and Its Ethers. *International Journal of Toxicology*, 18(3):53-67, 1999.

Barditch-Crovo et al., Quantitation of vaginally administered nonoxynol-9 in premenopausal women. *Contraception*, 55(4):261-263, 1997.

Beringer et al., An overview of economic issues in computer-assisted total joint arthroplasty. *Clinical Orthopedics & Related Research*, 463:26-30, 2007.

Bittner et al., Melatonin enhances the in vitro and in vivo repair of severed rat sciatic axons. *Neuroscience Letters*, 376(2):98-101, 2005.

Borgens et al., Behavioral recovery from spinal cord injury following delayed application of polyethylene glycol. *The Journal of Experimental Biology*, 205:1-12, 2002.

Borgens and Bohnert, Rapid Recovery from Spinal Cord Injury After Subcutaneously Administered Polyethylene Glycol. *Journal of Neuroscience Research*, 66:1179-1186, 2001.

Borgens and Shi, Acute repair of crushed guinea pig spinal cord by polyethylene glycol. *J. Neurophysiology*, 81:2406-2414, 1999.

Borgens and Shi, Immediate recovery from spinal cord injury through molecular repair of nerve membranes with polyethylene glycol. *FASEB J.*, 14:27-35, 2000.

Bove et al., Weight bearing as a measure of disease progression and efficacy of anti-inflammatory compounds in a model of monosodium iodoacetate-induced osteoarthritis. *Osteoarthritis and Cartilage*, 11:821-830, 2003.

Britt et al., Polyethylene Glycol Rapidly Restores Axonal Integrity and Improves the Rate of Motor Behavior Recovery after Sciatic Nerve Crush Injury. *J. Neurophysiol.*, 104:695-703, 2010.

Christensson et al., Infections in patients with implants and prostheses—an epidemiologic and clinical review. *Lakartidningen*, 101(11):982-984, 987-988, 2004.

Clarke et al., Gait Analysis in a Rat Model of Osteoarthrosis. *Physiology & Behavior*, 62:951-954, 1997.

Clayton and Clayton (eds.), Patty's Industrial Hygiene and Toxicology, Volumes 2A, 2B, 2C, 2D, 2E, 2F: Toxicology. 4th ed. New York, N.Y.: John Wiley & Sons Inc., 1993-1994, p. 3848.

Cledes et al., Validation of a chemical osteoarthritis model in rabbit temporomandibular joint: a compliment to biomechanical models. *International Journal of Oral & Maxillofacial Surgery*, 35(11): 1026-1033, 2006.

Conforti et al., Anti-inflammatory activity of monomethoxypolyethylene glycol superoxide dismutase on adjuvant arthritis in rats. *Pharmacological Research*, 23:51-56, 1991.

Cross et al., Antimicrobial Susceptibility Testing of *Chlamydia trachomatis* using a Reverse Transcriptase PCR-Based Method. *Antimicrob. Agents Chemother.*, 43(9): 2311-2313, 1999.

Das et al., Effects of individual control of pH and hypoxia in chondrocyte culture. *J. Orthop. Res.*, 28(4):537-545, 2010.

Delgado, Analytical Partitioning of polyethylene glycol modified proteins. *J. Chromatography B: Biomedical Sci. and Applications*, 692:263-272, 1997.

Fee and Van Alstine, PEG-Proteins: Reaction Engineering and Separation Issues. *Biomol. Engineering*, 61:924-939, 2006.

Final report on the safety assessment of hydroxyethylcellulose, *International Journal of Toxicology*, 1986 5(3):1-59, 1986.

Gale, Biotribological assessment for artificial synovial joints: the role of boundary lubrication. Institute of Health and Biomedical Innovation, Queensland University of Technology, Brisbane, 2007.

Genitrix HY50 Vet datasheet, Legend® package insert (hyaluronate sodium) Injectable Solution, Bayer HealthCare LEC, Animal Health Division, Shawnee Mission, Kans.

GRAS food ingredients. Cellulose and derivatives. For the FDA, National Technical Information Service (NTIS) PB No. 221-228.

Grass et al., Silver Ion Mediated Shape Control of Platinum Nanoparticles: Removal of Silver by Selective Etching Leads to Increased Catalytic Activity. *J. Phys. Chem.*, 112:4797-4804, 2008.

Guingamp et al., Mono-iodoacetate induced experimental osteoarthritis. *Arthritis & Rheumatism*, 40:1670-1679, 1997.

Harris (ed.), Polyethylene Glycol Chemistry, Biotechnical and Biomedical Applications. Plenum Press, New York and London, p. 7, 1992.

Herold et al., *Biochem. Pharmacol.*, 38:73, 1989.

Hsu et al., Template-directed instrumentation in total knee arthroplasty: cost savings analysis. *Orthopedics*, 35(11): e1596-1600, 2012.

Joung et al., In situ forming, metal-adhesive heparin hydrogel surfaces for blood-compatible coating. *Colloids and Surfaces B: Biointerfaces*, 99:102-107, 2012.

Koob et al., Intravenous polyethylene glycol inhibits the loss of cerebral cells after brain injury. *J. Neurotrauma*, 22:1092-1111, 2005.

Krause and Bittner Rapid morphological fusion of severed myelinated axons by polyethylene glycol. *Proc. Natl. Acad. Sci. USA*, 87(4):1471-1475, 1990.

Kremers et al., Determinants of direct medical costs in primary and revision total knee arthroplasty. *Clinical Orthopedics & Related Research*, 471(1):206-214, 2013.

Lalani et al., Clinical outcomes and costs among patients with *Staphylococcus aureus* bacteremia and orthopedic device infections. *Scandinavian Journal of Infectious Diseases*, 40(11-12):973-977, 2008.

Langenskiold et al., Osteoarthritis of the knee in the rabbit produced by immobilization. *Acta Orthop. Scand.*, 50:1-14, 1979.

Liberles and Buck, A second class of chemosensory receptor in the olfactory epithelium. *Nature*, 443:645-650, 2006.

Lim et al. In vitro and in vivo degradation behavior of acetylated chitosan porous beads. *J. Bioveter Sci Polym Ed.* 19(4):543-66. 2008.

Lockard et al., Efficacy and toxicity of the solvent polyethylene glycol 400 in monkey model. *Epilepsia*, 20(1):77-84, 1979.

Losina et al., Cost-effectiveness of Total Knee Arthroplasty in the United States. *Arch. Intern. Med.*, 169(12):1113-1122, 2009.

Luo et al., Polyethylene glycol improves function and reduces oxidative stress in synaptosomal preparations following spinal cord injury. *J. Neurotrauma*, 21:994-1007, 2004.

McCarty, Enhanced synovial production of hyaluronic acid may explain rapid clinical response to high-dose glucosamine in osteoarthritis. *Medical Hypotheses*, 50:500-510, 1998.

McClatchey, Clinical laboratory medicine. Lippincott Williams & Wilkins. p. 512, 2002.

McDonald and Spitzer, Polyvinylpyrrolidone: The electromigration characteristics of the blood plasma expander. *Circulation*, 1:396-404, 1953.

McPherson et al., Determination of the spermicide nonoxynol-9 in vaginal lavage by high-performance liquid chromatography. *Journal of Chromatography B: Biomedical Applications,* 677(1):204-208, 1996.

Minnesota Community Measurement, Total Knee Replacement—Impact and Recommendation Document. June 2010.

Moreland, Intra-articular hyaluronan (hyaluronic acid) and hylans for the treatment of osteoarthritis: mechanisms of action. *Arthritis Research & Therapy,* 5(2):54-67, 2003.

National Institutes of Health, Specialized Information Services, Household products database, on the world wide web at householdproducts.nlm.nih.gov/cgi-bin/household/brands?tbl=chem&id=51.

Nayak and Jain, In vitro and In vivo Study of Poly(ethylene glycol) Conjugated Ibuprofen to Extend the Duration of Action. *Sci. Pharm.,* 79:359-373, 2011.

Necas et al., Hyaluronic acid (hyaluronan): a review. *Veterinarni Medicina,* 53:397-411, 2008.

Neugebauer et al., Techniques for assessing knee joint pain in arthritis. *Molecular Pain,* 3:1-13, 2007.

NIH Consensus Development Conference on Total Knee Replacement, NIH Consensus Development Conference Statement. Dec. 8-12, 2003.

Oster, Spectral studies of polyvinylpyrrolidone. *J. Polymer Sc.,* 9:553, 1952.

Panush et al., Serum and synovial fluid IgG, IgA and IgM antigammaglobulins in rheumatoid arthritis. *Arthritis & Rheumatism,* 14(6):737-747, 1971.

Pape and Madry, The preclinical sheep model of high tibial osteotomy relating basic science to the clinics: standards, techniques and pitfalls. *Knee Surgery, Sports Traumatology, Arthroscopy,* 21(1):228-236, 2013.

Pasut and Veronese, Pegylation for improving the effectiveness of therapeutic biomolecules. *Drugs of Today,* 45:687-695, 2009.

Peng et al., Hyaluronic acid inhibits nitric oxide-induced apoptosis and dedifferentiation of articular chondrocytes in vitro. *Inflamm. Res.,* 59:519-530, 2010.

Rihl et al., Persistent infection of *Chlamydia* in reactive arthritis. *Ann. Rheum. Dis.,* 65:281-284, 2006.

Rosenthale and Capetola, Adjuvant arthritis; immunopathological and hyperalgesic features. *Federation Proceedings,* 41:2577-2582, 1982.

Savage, Water structure, p. 3-39. In: Water and Biological Macromolecules. Westhof. (ed.), CRC Press, Boca Raton, Fla., 1993.

Schrimsher and Reier, Forelimb Motor Performance Following Dorsal Column, Dorsolateral Funicular, or Ventrolateral Funicular Lesions of the Cervical Spinal Cord in the Rat. *Experimental Neurology,* 120(2):264-276, 1993.

Scott et al., A simple in situ cyanogen bromide cleavage method to obtain internal amino acid sequence of proteins electroblotted to polyvinyldifluoride membranes. *Biochem. Biophys. Res. Commun.,* 155(3):1353-1359, 1988.

Scott et al., Clonal characterization of the human IgG antibody repertoire to *Haemophilus influenzae* type b polysaccharide. II. IgG antibodies contain VH genes from a single VH family and VL genes from at least four VL families. *J. Immunol.,* 143(1):293-298, 1989.

Shi et al., Functional reconnection of severed mammalian spinal cord axons with polyethylene glycol. *J. Neurotrauma,* 16:727-738, 1999.

Shi and Borgens, Acute repair of crushed guinea pig spinal cord by polyethylene glycol. *J. Neurophysiol.,* 81:2406-2414, 1999.

Stern, Hyaluronan catabolism: a new metabolic pathway. *Eur. J. Cell Biol.,* 83:31-325, 2004.

Stiehm et al., Serum levels of IgM, IgG, and IgA. *Pediatrics,* 37:715, 1966.

Tang et al., Modulation of collagen-induced arthritis by adenovirus-mediated intra-articular expression of modified collagen type II. *Arthritis Research & Therapy,* 12:R136, 2010.

Tarrand et al., Clonal characterization of the human IgG antibody repertoire to *Haemophilus influenzae* type B polysaccharide. Demonstration of three types of V regions and their association with H and L chain isotypes. *J. Immunol.,* 142(7):2519-2526, 1989.

Trimpin et al., Recalcitrance of poly(vinylpyrrolidone): evidence through matrix-assisted laser desorption-ionization time-of-flight mass spectrometry. *J. Chromatogr. A.,* 938(1-2):67-77, 2001.

Turner, Effect of sodium monoiodoacetate on metabolism. *New Phytologist,* 37(4), 289-311, 1938.

Uebelhart et al., Protective effects of exogenous chondroitin 4,6-sulfate in the acute degradation of articular cartilage in the rabbit. *Osteoarthritis and Cartilage,* 6:(Suppl. A):6-13, 1998.

van Wijck et al., Polyethylene glycol versus dual sugar assay for gastrointestinal permeability analysis: is it time to choose? *Clin. Exp. Gastroenterol.,* 5:139-150, 2012.

Walter et al., Disposition of C14-Nonoxynol-9 after intravenous or vaginal administration to Female Sprague Dauley Rats. *Tox. Ap. Pharm.,* 96:258-268, 1988.

Witter et al., Duration of vaginal retention and potential duration of antiviral activity for five nonoxynol-9 containing intravaginal contraceptives. *Int. J. Gynaecology & Obstetrics,* 65(2):165-170, 1999.

Wu et al., Effect of extracellular pH on matrix synthesis by chondrocytes in 3D agarose gel. *Biotechnol. Prog.,* 23(2): 430-434, 2007.

Xiao et al., Investigation on three-dimensional temperature field of human knee considering anatomical structure. *International J. of Heat and Mass Transfer,* 54:1851-1860, 2011.

van de Sande et al., Characteristics of synovial inflammation in early arthritis analyzed by pixel-by-pixel time-intensity curve shape analysis. *Rheumatology,* 51:1240-1245, 2012.

van Wijck et al., Polyethylene glycol versus dual sugar assay for gastrointestinal permeability analysis: is it time to choose? *Clin. Exp. Gastroenterol.,* 5:139-150, 2012.

What is claimed is:

1. A method for lubricating a joint of a mammal comprising administered into a cavity of the joint an effective amount of a composition comprising between 0.01% and 6% (weight/volume) polyethylene glycol (PEG) 600K-10M, between 0.1% and 5% (weight/volume) PEG 100K-600K, and 0.1% to 10% (weight/volume) PEG 260-100K, wherein the composition comprises at least 1.6% (weight/volume) polyethylene glycol (PEG), wherein the composition is a liquid at the temperature of the joint and the oncotic pressure of the composition is not greater than the serum oncotic pressure of the mammal.

2. The method of claim 1, wherein at least a portion of the PEG is conjugated to an antimicrobial agent, antifungal agent, and/or antiviral agent.

3. The method of claim 1, wherein at least a portion of the PEG is comprised in a block polymer.

4. The method of claim 1, wherein administering comprises warming the composition to the temperature of the joint prior to administration.

5. The method of claim 1, wherein the mammal has joint dysfunction.

6. The method of claim 5, wherein the joint dysfunction is caused by a degenerative bone disease, osteoarthritis, rheumatoid arthritis, an infectious disease, an immune disease, an autoimmune disease, or sepsis.

7. The method of claim 1, wherein the composition further comprises polytetrafluoroethylene.

8. The method of claim 1, wherein the composition comprises at least 2% (weight/volume) PEG.

9. The method of claim 1, wherein administering comprises injecting the composition into an intra-articular cavity of the joint.

10. The method of claim 1, wherein the composition further comprises polyvinyl pyrrolidone (PVP) or polyvinyl alcohol (PVA).

11. The method of claim 10, wherein the composition comprises up to about 12% (weight/volume) PVP.

12. The method of claim 1, wherein the composition further comprises hydroxyethyl cellulose (HEC), methylcellulose, hydroxypropyl cellulose (HPC), or a combination thereof.

13. The method of claim 12, wherein the composition comprises up to about 12% (weight/volume) HEC.

14. The method of claim 1, wherein the composition further comprises chondroitin, dextran, polyglucosamine (chitosan), agarose, xanthan gum, alginate, carrageenan, guar gum, locust bean gum, or a combination thereof.

15. The method of claim 1, wherein the composition further comprises DMSO, mineral oil, paraffin jelly, silicone oil, or a combination thereof.

16. The method of claim 1, wherein the composition further comprises ethanol, steryl alcohol, phosphatidylcholine, oleic acid, oleyl alcohol, hydroxyl stearate, cetyl alcohol, myristyl lactate, isopropyl myristate, or a combination thereof.

17. The method of claim 1, wherein the composition comprises PEG-tyramine.

* * * * *